United States Patent
Wang et al.

(10) Patent No.: US 11,464,780 B2
(45) Date of Patent: Oct. 11, 2022

(54) PYRAZOLOPYRIMIDINE DERIVATIVE AND USE THEREOF

(71) Applicant: Simcere Pharmaceutical Co. Ltd., Jiangsu (CN)

(72) Inventors: Jianfei Wang, Shanghai (CN); Jikui Sun, Shanghai (CN); Wenyuan Zhu, Shanghai (CN); Yang Zhang, Shanghai (CN); Jie Li, Shanghai (CN); Jian Li, Shanghai (CN); Shuhui Chen, Shanghai (CN)

(73) Assignee: Simcere Pharmaceutical Co. Ltd., Nanjing (CN)

( * ) Notice: Subject to any disclaimer, the term of this patent is extended or adjusted under 35 U.S.C. 154(b) by 180 days.

(21) Appl. No.: 16/975,824

(22) PCT Filed: Feb. 27, 2019

(86) PCT No.: PCT/CN2019/076251
§ 371 (c)(1),
(2) Date: Aug. 26, 2020

(87) PCT Pub. No.: WO2019/165967
PCT Pub. Date: Sep. 6, 2019

(65) Prior Publication Data
US 2020/0405725 A1  Dec. 31, 2020

(30) Foreign Application Priority Data

| Feb. 28, 2018 | (CN) | 201810167756.3 |
| Sep. 19, 2018 | (CN) | 201811095822.7 |
| Jan. 7, 2019 | (CN) | 201910015376.2 |

(51) Int. Cl.
| *A61K 31/529* | (2006.01) |
| *A61P 35/00* | (2006.01) |
| *C07D 498/08* | (2006.01) |
| *C07D 498/20* | (2006.01) |
| *C07D 498/22* | (2006.01) |

(52) U.S. Cl.
CPC ............ *A61K 31/529* (2013.01); *A61P 35/00* (2018.01); *C07D 498/22* (2013.01)

(58) Field of Classification Search
CPC .. C07D 498/08; C07D 498/20; C07D 498/22; A61K 35/00; A61K 31/529; A61P 31/529; A61P 35/00
See application file for complete search history.

(56) References Cited

FOREIGN PATENT DOCUMENTS

| CN | 101679429 A | 3/2010 |
| CN | 102971322 A | 3/2013 |
| CN | 107207514 A | 9/2017 |
| WO | WO-2011146336 A1 | 11/2011 |
| WO | WO-2015050989 A2 | 4/2015 |

OTHER PUBLICATIONS

International Search Report regarding International Application No. PCT/CN2019/076251, dated May 30, 2019.
Written Opinion of the International Searching Authority regarding International Application No. PCT/CN2019/076251, dated May 30, 2019.
Mar. 26, 2021 Extended European Search Report issued in Europe Patent Application EP19761117.

*Primary Examiner* — Brenda L Coleman
(74) *Attorney, Agent, or Firm* — Harness, Dickey & Pierce, P.L.C.

(57) ABSTRACT

A compound of formula (II), a tautomer thereof or a pharmaceutically acceptable salt thereof, and use thereof in the preparation of medicaments for treating solid tumor-related diseases.

19 Claims, 1 Drawing Sheet

PYRAZOLOPYRIMIDINE DERIVATIVE AND USE THEREOF

CROSS-REFERENCE TO RELATED APPLICATIONS

This application is a U.S. National Phase Application under 35 U.S.C. 371 of International Application No. PCT/CN2019/076251, filed Feb. 27, 2019, which claims the benefit of Chinese Patent Application No. CN 201810167756.3, filed Feb. 28, 2018, Chinese Patent Application No. CN 201811095822.7, filed Sep. 19, 2018, and Chinese Patent Application No. CN 201910015376.2, filed Jan. 7, 2019. The entire disclosures of the above applications are incorporated herein by reference.

TECHNICAL FIELD

The present disclosure relates to a variety of carcinogenic fusion kinase inhibitors, their uses and synthesis methods, and specifically relates to a use of a compound represented by formula (II), a tautomer or a pharmaceutically acceptable salt in the preparation of a medicament for treating solid tumor-related diseases.

BACKGROUND ART

Protein kinases are closely related to cell proliferation, differentiation, metabolism and apoptosis. The oncogenic forms of protein kinases are abundantly expressed in many different types of human tumors and are highly responsive to specific kinase inhibitors. Among them, anaplastic lymphoma kinase (ALK) is a receptor tyrosine kinase (RTK) belonging to the insulin receptor superfamily. It is mainly expressed in the central and peripheral nervous system, plays a role in the normal development and function of the nervous system, and has been widely studied in a large number of preclinical and clinical studies. ALK was first discovered as a persistently activated carcinogenic form caused by chromosomal translocation in anaplastic large cell lymphoma (ALCL), which is NPM-ALK fusion protein formed by fusion between the N-terminal of normally expressed nucleophosmin (NPM) and ALK kinase domain. Currently, a variety of ALK fusion proteins have been identified and are considered to be powerful oncogenic driving factors of some tumors (such as inflammatory myofibroblastoma). Therefore, ALK fusion proteins have also become important targets for cancer treatment and intervention. Multiple ALK inhibitors have entered clinical trials and have been approved for marketing. Among them, crizotinib was approved in 2011 for the treatment of ALK-positive non-small cell lung cancer (NSCLC) patients. In 2014, ceritinib was approved for the treatment of ALK-positive metastatic NSCLC patients. Although ALK inhibitors have been proven effective in the initial clinical trials, relapses have always been observed in treated patients, and ALK acquired resistance mutations appeare. Among them, the emergence of brain metastases is an obvious cause of disease relapses in patients treated with crizotinib.

Tropomyosin-related kinase (Trk) is a type of nerve growth factor receptor (NGF) highly expressed in nerve cells. The Trk family consists of highly homologous tropomyosin-related kinase A (TrkA), tropomyosin-related kinase B (TrkB), and tropomyosin-related kinase C (TrkC), which code NTRK1, NTRK2 and NTRK3 respectively, and involves 4 ligands including NGF, BDNF, NT-4 and NT-3. They are widely involved in important physiological activities such as cell proliferation, differentiation, survival, and neuron growth by regulating the signaling pathways of PI3K-AKT, RAS-RAF-ERK, PLCγ-PKC and the like. The persistently activated oncogenic form of Trk was first discovered as an oncogenic fusion gene (TPM3-NTRK1) from colorectal cancer. Oncogenic Trk gene fusions are capable of promoting cancer cell proliferation and affect cancer-related downstream signaling pathways, such as ERK, AKT, without ligand induced activation. Drugs targeting TRK gene fusions, such as entrectinib (RXDX-101) and larotrectinib (LOXO-101), have also been proven effective in the initial clinical trials. However, under sustained action, acquired resistance mutations also appeare in the treated patients. New drugs targeting TRK gene fusions such as TPX-0005 and LOXO-195 partially solved the problem of resistance mutations.

Ros1 kinase is a type of receptor tyrosine kinase, which has an important influence on normal physiological functions. The persistently activated oncogenic Ros1 fusion proteins have also been found in a variety of human cancers, including glioblastoma, non-small cell lung cancer, colorectal cancer and the like. Many drugs targeting Ros1 fusion proteins, such as crizotinib, have been proven effective clinically, but acquired resistance mutations have also been found in patients after persistent administration.

Therefore, the compounds capable of inhibiting multiple oncogenic fusion kinases and their mutations are urgently need as regards the clinical treatment of some cancers.

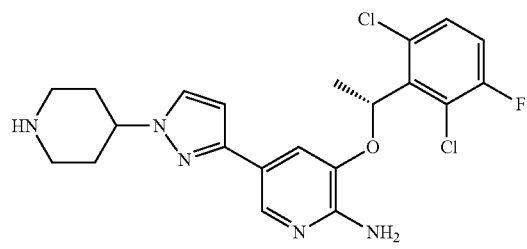

Crizotinib

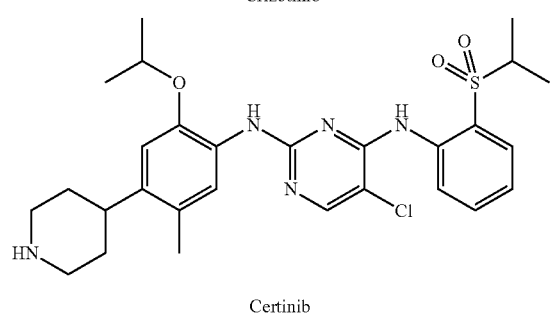

Certinib

-continued (RXDX-101)

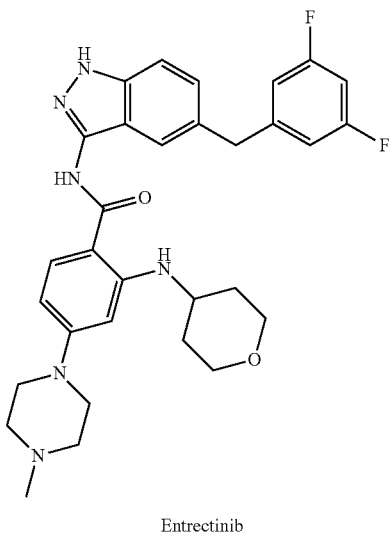

Entrectinib (LOXO-101)

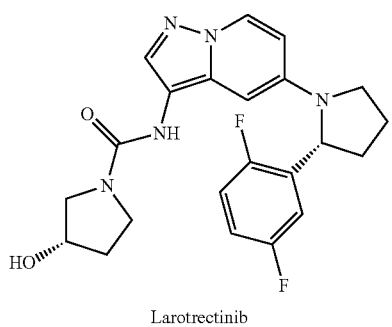

Larotrectinib

LOXO-195

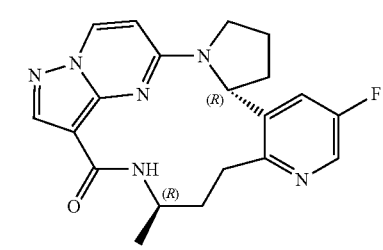

TPX-0005

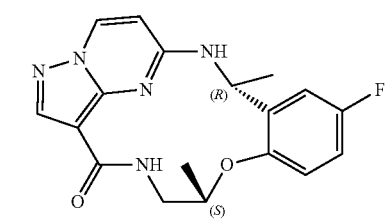

CONTENT OF THE INVENTION

The present disclosure provides a compound represented by formula (II), an isomer thereof or a pharmaceutically acceptable salt thereof,

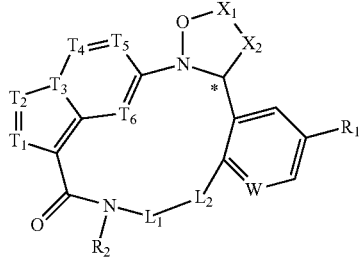

wherein, $T_1$, $T_2$, $T_3$, $T_4$, $T_5$ and $T_6$ are each independently selected from the group consisting of $CR_3$ and N;

W is selected from the group consisting of $CR_4$ and N;

$X_1$ and $X_2$ are each independently $CR_5R_6$;

$R_1$ is selected from the group consisting of H, F, Cl, Br, I, OH, $NH_2$, CN and $C_{1-6}$ alkyl, wherein the $C_{1-6}$ alkyl is optionally substituted by 1, 2 or 3 $R_a$;

$R_2$ is selected from the group consisting of H and $C_{1-6}$ alkyl, wherein the $C_{1-6}$ alkyl is optionally substituted by 1, 2 or 3 $R_b$;

$R_3$ and $R_4$ are each independently selected from the group consisting of H, F, Cl, Br, I, OH and $NH_2$;

$R_5$ and $R_6$ are each independently selected from the group consisting of H, F, Cl, Br, I, OH, $NH_2$ and $C_{1-6}$ alkyl;

$L_1$ is selected from the group consisting of —$C_{1-3}$ alkyl-, —$C_{3-6}$ cycloalkyl- and -4- to 6-membered heterocycloalkyl-, wherein the —$C_{1-3}$ alkyl-, —$C_{3-6}$ cycloalkyl- and -4- to 6-membered heterocycloalkyl- are optionally substituted by 1, 2 or 3 $R_c$;

$L_2$ is selected from the group consisting of —$C_{1-3}$ alkyl-, —$C_{1-3}$ alkyl-O—, —N($R_d$)—, —$C_{1-3}$ alkyl-N($R_d$)— and —O—;

$R_a$ is independently selected from the group consisting of H, F, Cl, Br, I, OH and $NH_2$;

$R_b$ is selected from the group consisting of H, F, Cl, Br, I, OH and $NH_2$;

$R_c$ is selected from the group consisting of H, F, Cl, Br, I, OH, $NH_2$, CN, $C_{1-3}$ alkyl and $C_{1-3}$ alkyl-C=O—, wherein the $C_{1-3}$ alkyl and $C_{1-3}$ alkyl-C=O— are optionally substituted by 1, 2 or 3 R;

$R_d$ is selected from the group consisting of H and $C_{1-3}$ alkyl;

R is independently selected from the group consisting of F, Cl, Br, I, OH and $NH_2$;

the carbon atom marked with "*" is a chiral carbon atom present in a single enantiomer form of (R) or (S) or in a form enriched in one enantiomer;

the 4- to 6-membered heterocycloalkyl independently comprises 1, 2, 3 or 4 heteroatoms or heteroatomic groups independently selected from the group consisting of —NH—, —O—, —S— and N.

In some embodiments of the present disclosure, $R_1$ is independently selected from the group consisting of H, F, Cl, Br, I, OH, $NH_2$, CN and $CH_3$, and other variables are as defined in the present disclosure.

In some embodiments of the present disclosure, $R_2$ is selected from the group consisting of H and $CH_3$, and other variables are as defined in the present disclosure.

In some embodiments of the present disclosure, $R_5$ and $R_6$ are each independently selected from the group consisting of H, F, Cl, Br, I, OH, $NH_2$ and $CH_3$, and other variables are as defined in the present disclosure.

In some embodiments of the present disclosure, $R_c$ is selected from the group consisting of H, F, Cl, Br, I, OH, $NH_2$, CN, $CH_3$, $CH_3CH_2$ and $CH_3C(=O)$, wherein the $CH_3$, $CH_3CH_2$ and $CH_3C(=O)$ are optionally substituted by 1, 2 or 3 R, and other variables are as defined in the present disclosure.

In some embodiments of the present disclosure, $R_c$ is selected from the group consisting of H, F, Cl, Br, I, OH, $NH_2$, CN, $CH_3$, $CH_2F$, $CHF_2$, $CF_3$, $CH_3CH_2$ and $CH_3C(=O)$, and other variables are as defined in the present disclosure.

In some embodiments of the present disclosure, $L_1$ is selected from the group consisting of —$CH_2$—, —$CH_2CH_2$—, -cyclopropyl-, -cyclobutyl-, -cyclopentyl-, -oxetanyl-, -tetrahydrofuranyl-, -tetrahydropyranyl-, -pyrrolidinyl- and -piperidinyl-, wherein the —$CH_2$—, —$CH_2CH_2$—, -cyclopropyl-, -cyclobutyl-, -cyclopentyl-, -oxetanyl-, -tetrahydrofuranyl-, -tetrahydropyranyl-, -pyrrolidinyl- and -piperidinyl- are optionally substituted by 1, 2 or 3 $R_c$, and other variables are as defined in the present disclosure.

In some embodiments of the present disclosure, $L_1$ is selected from the group consisting of —$CH_2$—, —$CH(CH_3)$—, —$C(CH_3)_2$—, —$CH_2CH_2$—,

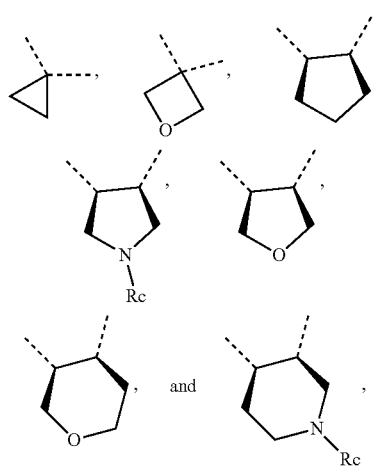

and other variables are as defined in the present disclosure.

In some embodiments of the present disclosure, $L_1$ is selected from the group consisting of —$CH_2$—, —$CH_2CH_2$—, —$C(CH_3)_2$—, —$CH(CH_3)$—,

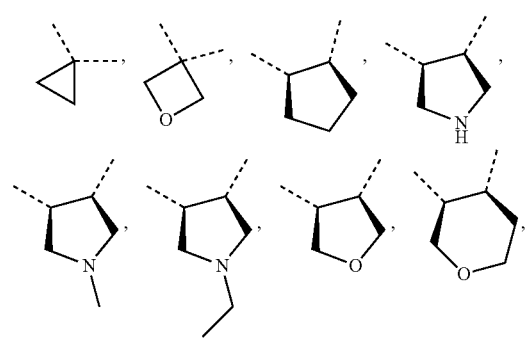

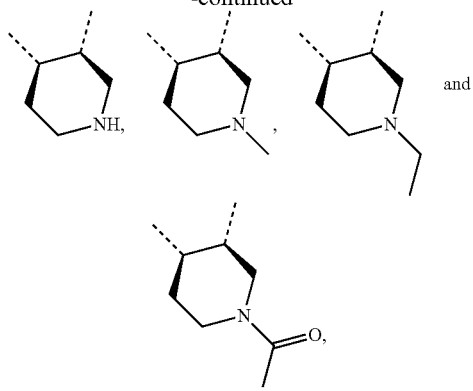

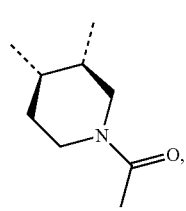

and other variables are as defined in the present disclosure.

In some embodiments of the present disclosure, $L_1$ is selected from the group consisting of —$CH_2$—, —$CH_2CH_2$—, —$CH(CH_3)$—,

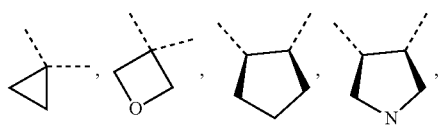

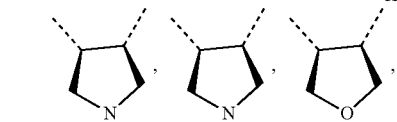

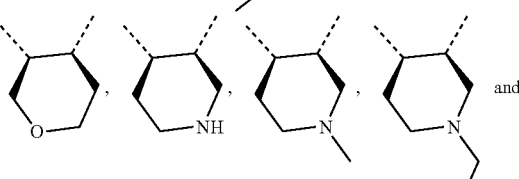

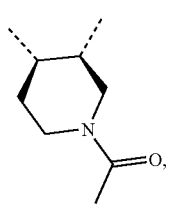

and other variables are as defined in the present disclosure.

In some embodiments of the present disclosure, $L_2$ is selected from the group consisting of —$CH_2$—, —$CH_2CH_2$—, —$CH_2CH_2O$—, —$CH(CH_3)O$—, —O—, —NH—, —$CH_2NH$— and —$CH_2O$—, and other variables are as defined in the present disclosure.

In some embodiments of the present disclosure, the moiety

is selected from the group consisting of

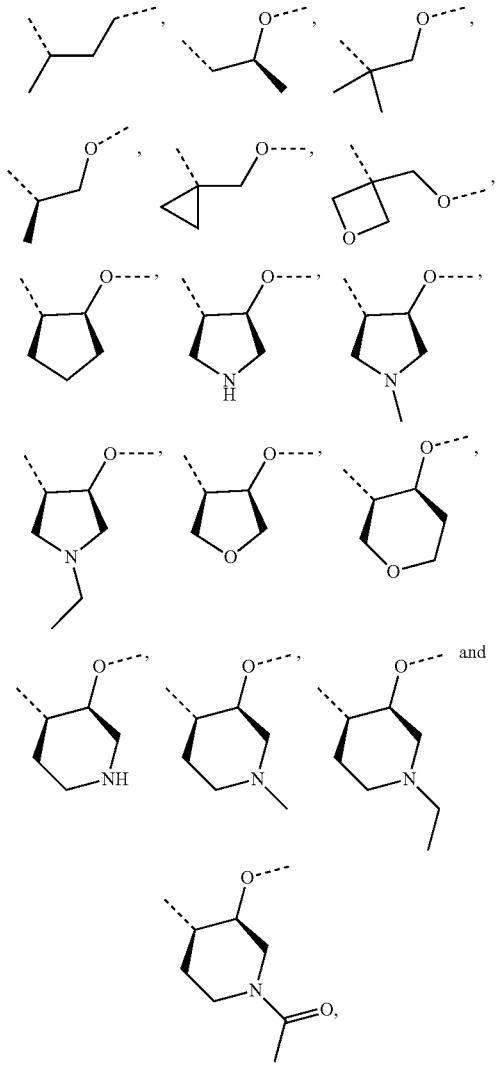

and other variables are as defined in the present disclosure.

In some embodiments of the present disclosure, the moiety

is selected from the group consisting of

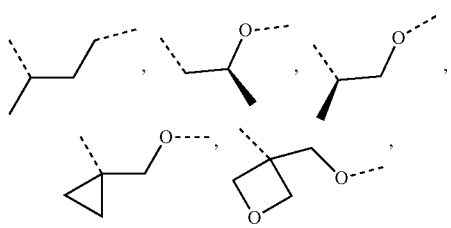

and other variables are as defined in the present disclosure.

In some embodiments of the present disclosure, the moiety

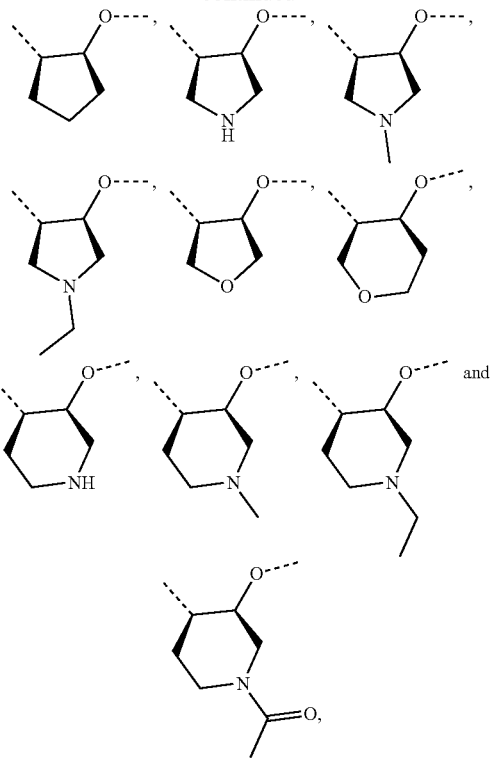

is

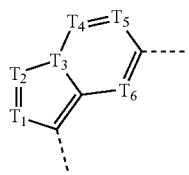

and other variables are as defined in the present disclosure.

In some embodiments of the present disclosure, the moiety

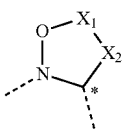

is

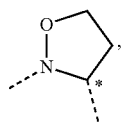

and other variables are as defined in the present disclosure.

The present disclosure also provides a compound represented by formula (I), an isomer thereof or a pharmaceutically acceptable salt thereof,

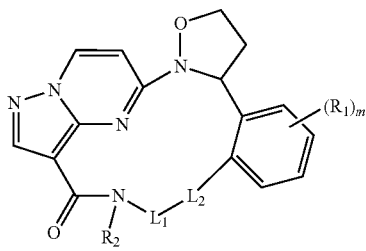

(I)

wherein,

T is selected from the group consisting of CH and N;

$R_1$ is independently selected from the group consisting of H, F, Cl, Br, I, OH, $NH_2$, CN and $C_{1-6}$ alkyl, wherein the $C_{1-6}$ alkyl is optionally substituted by 1, 2 or 3 $R_a$;

$R_2$ is selected from the group consisting of H and $C_{1-6}$ alkyl, wherein the $C_{1-6}$ alkyl is optionally substituted by 1, 2 or 3 $R_b$;

$L_1$ is —C($R_c$)($R_d$)—;

$L_2$ is selected from the group consisting of —(CH$_2$)$_n$— and —(CH$_2$)$_n$—O—;

m is selected from the group consisting of 1, 2 and 3;

n is independently selected from the group consisting of 1, 2 and 3;

$R_a$ is independently selected from the group consisting of H, F, Cl, Br, I, OH and $NH_2$;

$R_b$ is selected from the group consisting of H, F, Cl, Br, I, OH and $NH_2$;

$R_c$ and $R_d$ are each independently selected from the group consisting of H, F, Cl, Br, I, OH, $NH_2$, CN and $C_{1-3}$ alkyl, wherein the $C_{1-3}$ alkyl is optionally substituted by 1, 2 or 3 R; alternatively, $R_c$ and $R_d$ are linked together to form a $C_{3-6}$ cycloalkyl optionally substituted by 1, 2 or 3 R;

R is independently selected from the group consisting of H, F, Cl, Br, I, OH and $NH_2$.

In some embodiments of the present disclosure, $R_1$ is independently selected from the group consisting of H, F, Cl, Br, I, OH, $NH_2$, CN and $CH_3$, and other variables are as defined in the present disclosure.

In some embodiments of the present disclosure, $R_2$ is selected from the group consisting of H and $CH_3$, and other variables are as defined in the present disclosure.

In some embodiments of the present disclosure, $R_c$ and $R_d$ are independently selected from the group consisting of H, F, Cl, Br, I, OH, $NH_2$, CN, $CH_3$ and $CH_2CH_3$, wherein the $CH_3$ and $CH_2CH_3$ are optionally substituted by 1, 2 or 3 R, and other variables are as defined in the present disclosure.

In some embodiments of the present disclosure, $R_c$ and $R_d$ are independently selected from the group consisting of H, F, Cl, Br, I, OH, $NH_2$, CN, $CH_3$, $CH_2F$, $CHF_2$, $CF_3$ and $CH_2CH_3$, and other variables are as defined in the present disclosure.

In some embodiments of the present disclosure, $R_c$ and $R_d$ are linked together to form cyclopropyl optionally substituted by 1, 2 or 3 R, and other variables are as defined in the present disclosure.

In some embodiments of the present disclosure, $L_1$ is selected from the group consisting of —CH$_2$—,

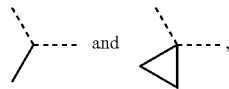

and other variables are as defined in the present disclosure.

In some embodiments of the present disclosure, $L_2$ is selected from the group consisting of —CH$_2$—, —CH$_2$CH$_2$—, —CH$_2$CH$_2$—O— and —CH$_2$—O—, and other variables are as defined in the present disclosure.

The present disclosure also provides some embodiments derived from any combination of the above variables.

In some embodiments of the present disclosure, the compound, isomer thereof, or pharmaceutically acceptable salt thereof is selected from:

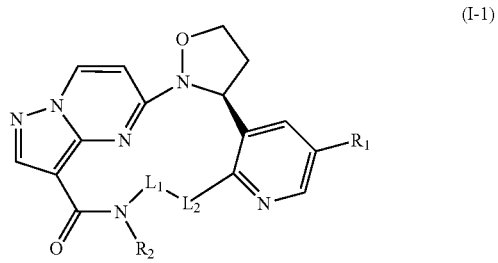

(I-1)

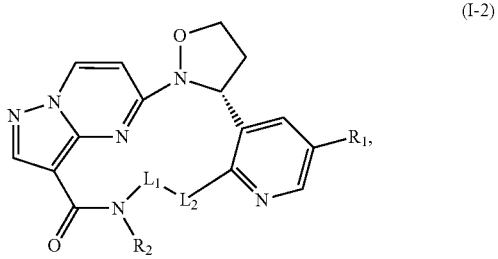

(I-2)

wherein $R_1$, $R_2$, $L_1$ and $L_2$ are as defined in the present disclosure.

In some embodiments of the present disclosure, the compound, isomer thereof, or pharmaceutically acceptable salt thereof is selected from:

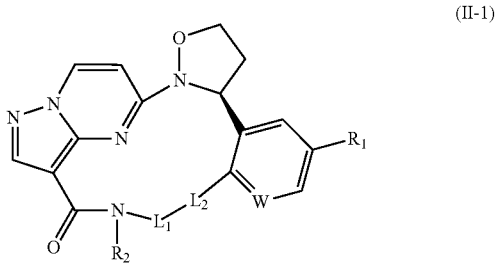

(II-1)

(II-2)

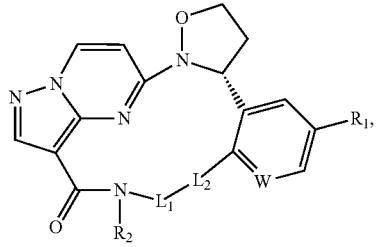

wherein,

R₁, R₂, W, L₁ and L₂ are as defined in the present disclosure.

In some embodiments of the present disclosure, the compound, isomer thereof, or pharmaceutically acceptable salt thereof is selected from:

(II-3)

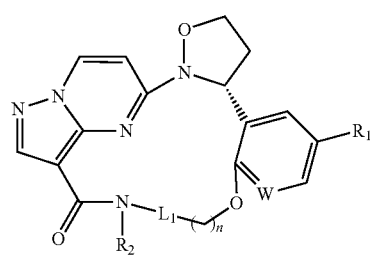

(II-4)

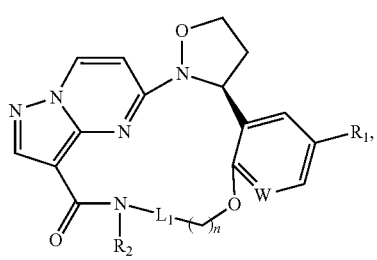

wherein, n is selected from the group consisting of 0 and 1;

W, R₁, R₂, L₁ and L₂ are as defined in the present disclosure.

The present disclosure also provides a compound represented by formula as shown below, an isomer thereof or a pharmaceutically acceptable salt thereof, which is selected from:

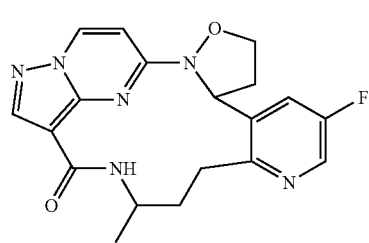

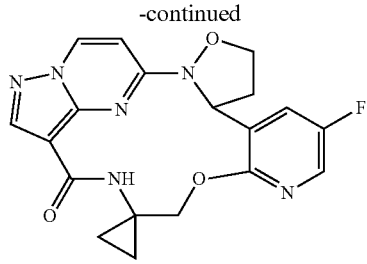

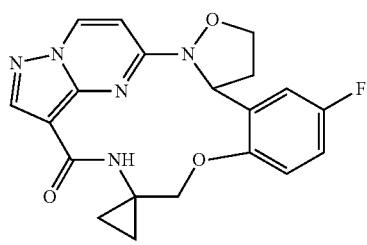

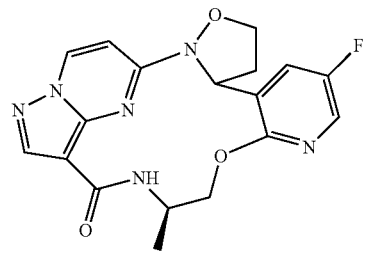

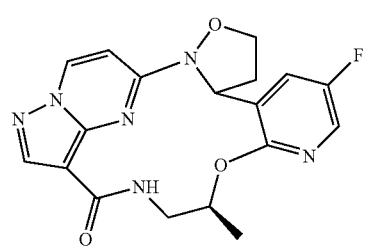

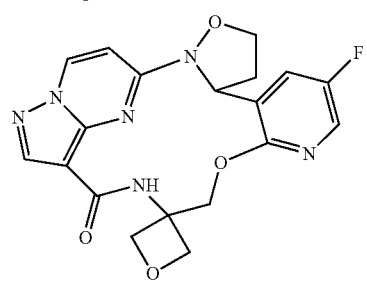

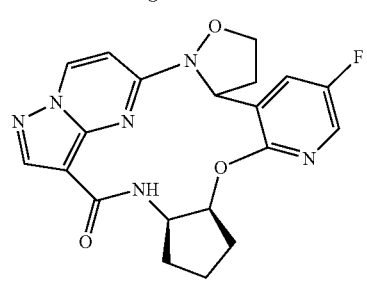

-continued
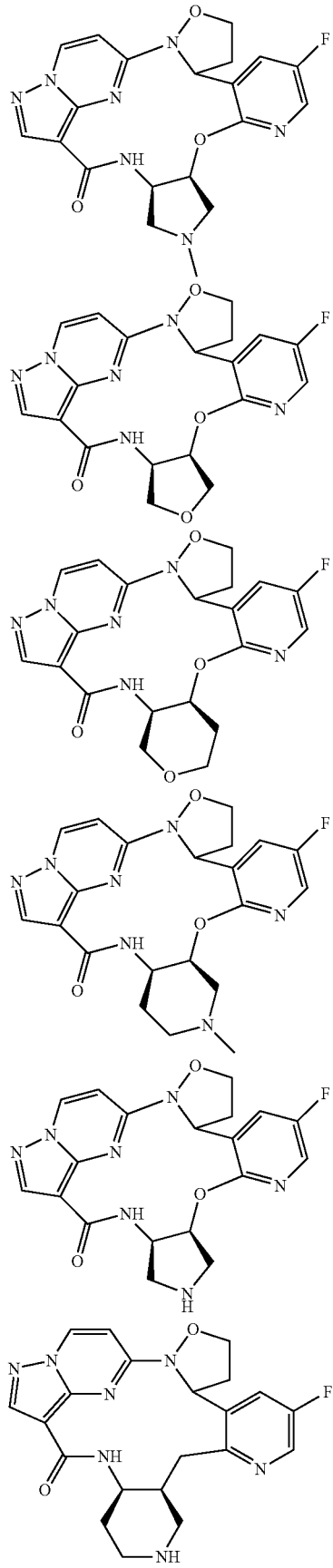
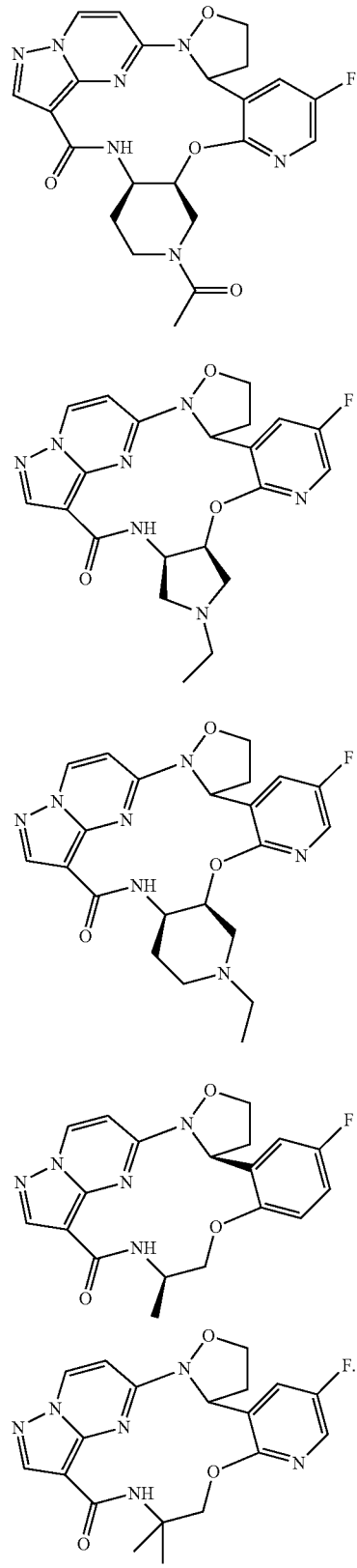
In some embodiments of the present disclosure, the compound, isomer thereof or pharmaceutically acceptable salt thereof is selected from

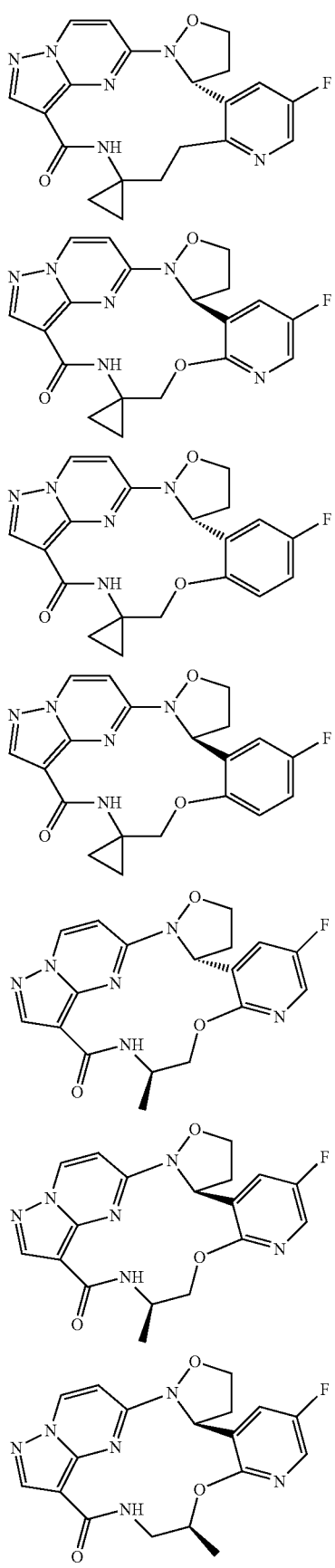
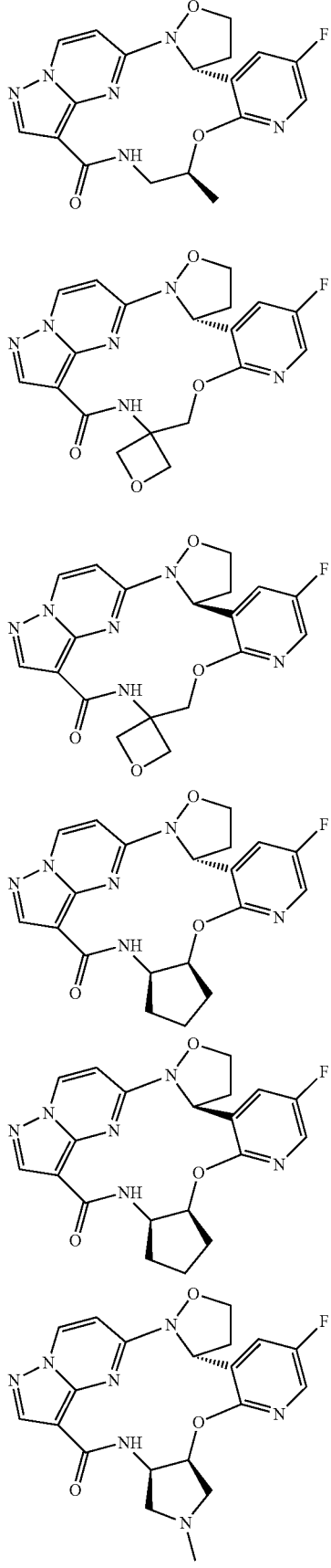

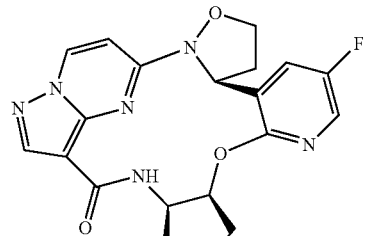
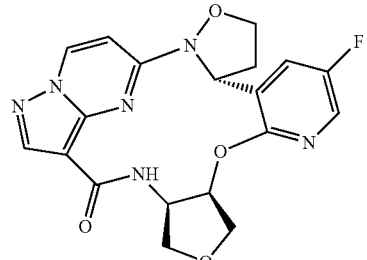
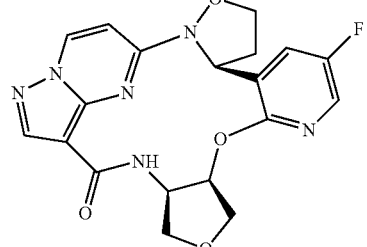
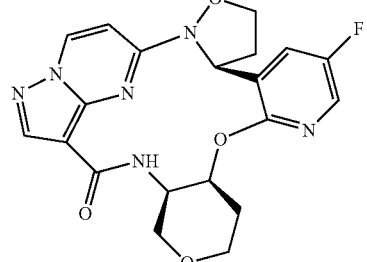
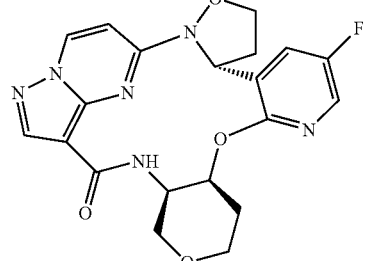
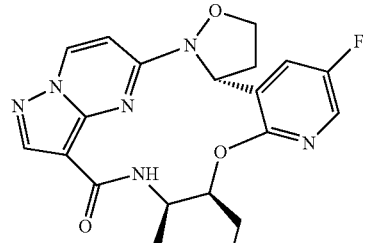
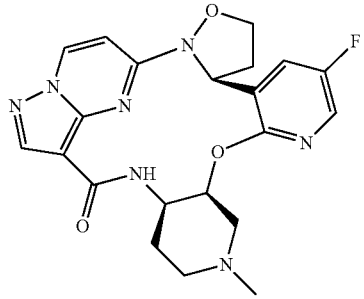
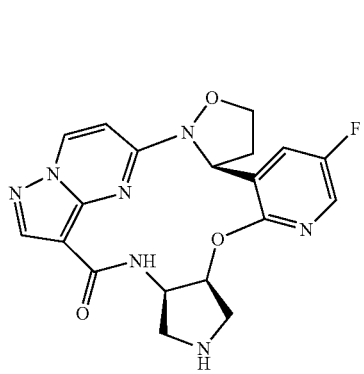
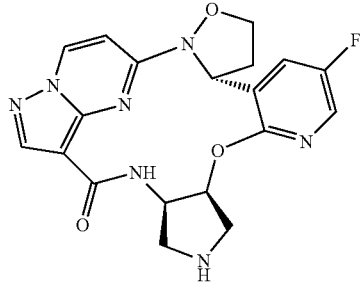
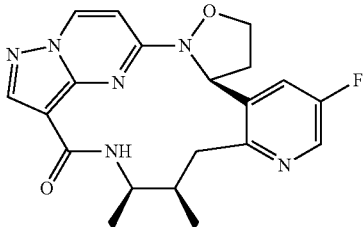
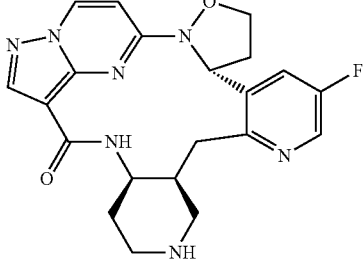

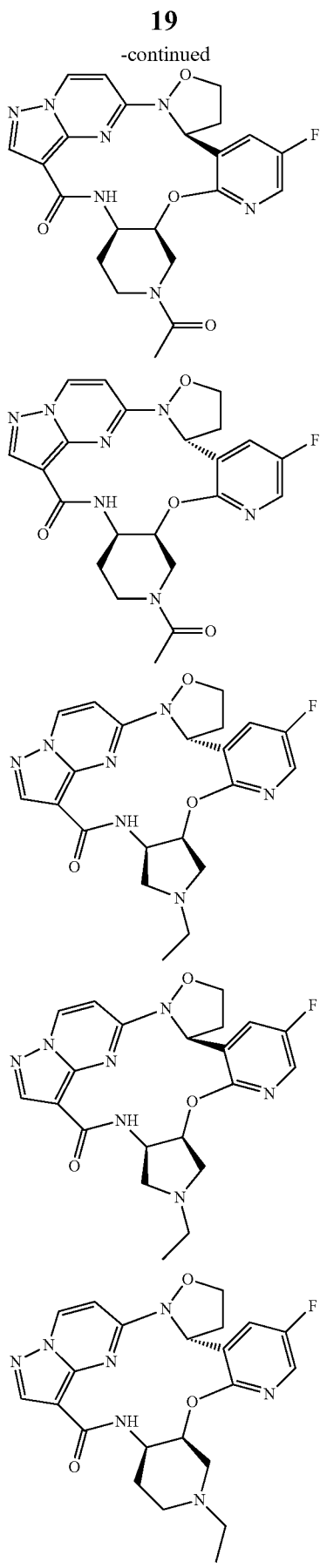

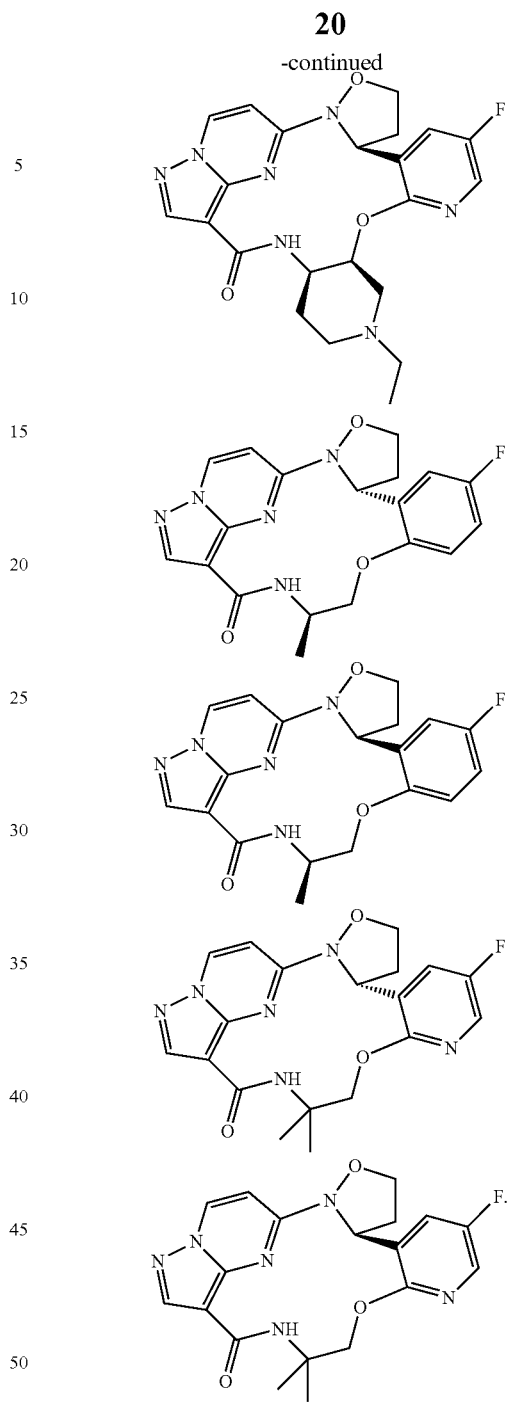

The present disclosure also provides a pharmaceutical composition comprising a therapeutically effective amount of the compound or pharmaceutically acceptable salt thereof as active ingredient and a pharmaceutically acceptable carrier.

The present disclosure also provides a use of the compound or pharmaceutically acceptable salt thereof or the composition in the preparation of a medicament for treating a disease related to Trk, ALK and Ros1 kinase.

In some embodiments of the present disclosure, the medicament is a medicament for treating a solid tumor.

Technical effects: The compound of the present disclosure has shown a significant effect of inhibiting cell proliferation in enzymatic and cellular level, and has shown a significant effect of inhibiting tumors in corresponding in vivo pharmacodynamic experiments of animals.

Definition and Description

Unless otherwise indicated, the following terms used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compound of the present disclosure may have a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present disclosure. The substituent such as alkyl may have an additional asymmetric carbon atom. All these isomers and mixtures thereof are encompassed within the scope of the present disclosure.

Unless otherwise indicated, the terms "enantiomers" or "optical isomers" refer to stereoisomers which are mirror images of each other.

Unless otherwise indicated, the terms "cis/trans-isomer" or "geometric isomer" are caused by the inability of a double bond or a single bond of a ring-forming carbon atom to rotate freely.

Unless otherwise indicated, the term "diastereomer" refers to a stereoisomer in which a molecule has two or more chiral centers, and there is non-mirror image relationship between molecules.

Unless otherwise indicated, "(D)" or "(+)" means dextrorotation, "(L)" or "(−)" means levorotation, and "(DL)" or "(±)" means racemization.

Unless otherwise indicated, a wedged solid bond ($\nearrow$) and a wedged dashed bond ($\nearrow$) represent the absolute configuration of a stereocenter, a straight solid bond ($\nearrow$) and a straight dashed bond ($\nearrow$) represent the relative configuration of a stereocenter, a wave line ($\sim$) represents a wedged solid bond ($\nearrow$) or a wedged dashed bond ($\nearrow$), or a wave line ($\sim$) represents a straight solid bond ($\nearrow$) or a straight dashed bond ($\nearrow$).

The compounds of the disclosure may be specific. Unless otherwise indicated, the term "tautomer" or "tautomeric form" means that at room temperature, the isomers of different functional groups are in dynamic equilibrium and can be quickly converted to each other. If tautomer is possible (e.g., in solution), the chemical equilibrium of the tautomer can be reached. For example, proton tautomer (also known as prototropic tautomer) include interconversions via proton migration, such as keto-enol isomerization and imine-enamine isomerization. Valence tautomer includes interconversion formed by recombination of some bonding electrons. A specific example of the keto-enol tautomerization is the interconversion between two tautomers of pentane-2,4-dione and 4-hydroxypent-3-en-2-one.

Unless otherwise indicated, the term "enriched in one isomer", "isomer enriched", "enriched in one enantiomer" or "enantiomer enriched" refers to that the content of the isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise indicated, the terms "isomer excess" or "enantiomer excess" refer to the difference between the relative percentages of two isomers or two enantiomers. For example, if the content of one isomer or enantiomer is 90%, and the content of the other isomer or enantiomer is 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compounds of the present disclosure may contain atomic isotopes in unnatural proportions on one or more of the atoms constituting the compound. For example, the compound can be radiolabeled with a radioactive isotope, such as tritium ($^3$H), iodine-125 ($^{125}$I) or C-14 ($^{14}$C). As another example, deuterated drugs can be obtained by replacing hydrogen by deuterium. The bond between deuterium and carbon is stronger than the bond between ordinary hydrogen and carbon. Compared with non-deuterated drugs, deuterated drugs have the advantages of reduced toxic and side effects, increased drug stability, enhanced efficacy, prolonged biological half-life of drugs, and the like. Transformations of all isotopic compositions of the compounds of the present disclosure, whether radioactive or not, are included within the scope of the disclosure.

"Optional" or "optionally" means that the subsequent event or condition may occur but not requisite, that the term includes the instance in which the event or condition occurs and the instance in which the event or condition does not occur.

The term "substituted" means any one or more hydrogen atoms on a specific atom are substituted by a substituent, including deuterium and hydrogen variants, as long as the valence of the specific atom is normal and the substituted compound is stable. When the substituent is oxygen (i.e. =O), it means two hydrogen atoms are substituted. Oxygen substitution does not occur on aromatic groups. The term "optionally substituted" means an atom can be substituted by a substituent or not, unless otherwise indicated, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative substituent does not indicate which atom is connected to the substituted group, the substituent can be bonded via any atom thereof. For example, a pyridyl, as a substituent, may be connected to the substituted group via any carbon atom on the pyridine ring. When the enumerative linking group does not indicate the direction for linking, the direction for linking is arbitrary, for example, the linking group L contained in

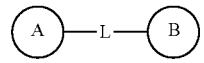

is -M-W—, then -M-W— can link ring A and ring B to form

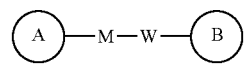

in the direction same as left-to-right reading order, and form

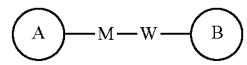

in the direction contrary to left-to-right reading order. Combinations of the linking groups, substituents and/or variants thereof are permissible only if such combinations result in stable compounds.

Unless otherwise indicated, the number of the atom on the ring is usually defined as the member number of the ring, for example, a "5-7 membered ring" means that 5 to 7 atoms are arranged on a ring.

Unless otherwise specified, the term "$C_{1-6}$ alkyl" is used to indicate a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, and the like; it can be monovalent (such as methyl), divalent (such as methylene) or multivalent (such as methine). Examples of $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it may be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl), and the like.

Unless otherwise specified, "$C_{3-6}$ cycloalkyl" refers to a saturated cyclic hydrocarbyl consisting of 3 to 6 carbon atoms, which is a monocyclic and bicyclic system, and the $C_{3-6}$ cycloalkyl includes $C_{3-5}$, $C_{4-5}$ and $C_{5-6}$ cycloalkyl, etc.; it can be monovalent, divalent or polyvalent. Examples of $C_{3-6}$ cycloalkyl include, but are not limited to, cyclopropyl, cyclobutyl, cyclopentyl, cyclohexyl, and the like.

Unless otherwise specified, the term "4- to 6-membered heterocycloalkyl" by itself or in combination with other terms, refers to a saturated cyclic group consisting of 4 to 6 ring atoms, respectively, of which 1, 2, 3 or 4 ring atoms are independently selected from 0, S and N heteroatoms, the rest are carbon atoms, wherein the nitrogen atom is optionally quaternized, and the nitrogen and sulfur heteroatoms are optionally oxidized (i.e. NO and S(O)$_p$, p is 1 or 2). It includes both monocyclic and bicyclic systems, wherein the bicyclic system includes a spiro ring, a fused ring, and a bridge ring. In addition, for the "4- to 6-membered heterocycloalkyl", a heteroatom may occupy connection position of the heterocycloalkyl to the rest of the molecule. The 4- to 6-membered heterocycloalkyl includes 5- to 6-membered, 4-membered, 5-membered and 6-membered heterocycloalkyl, and the like. Examples of 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1.2-oxazinyl, 1,2-thiazinyl, hexahydropyridazinyl, homopiperazinyl or homopiperidinyl and the like.

Unless otherwise specified, $C_{n-n+m}$ or $C_n-C_{n+m}$ includes any specific case of n to n+m carbons, for example, $C_{1-12}$ includes $C_1, C_2, C_3, C_4, C_5, C_6, C_7, C_8, C_9, C_{10}, C_{11}$ and $C_{12}$, also includes any range from n to n+m, for example, $C_{1-12}$ includes $C_{1-3}, C_{1-6}, C_{1-9}, C_{3-6}, C_{3-9}, C_{3-12}, C_{6-9}, C_{6-12}$ and $C_{9-12}$, etc.; in the same way, n to n+m means that the number of atoms in the ring is n to n+m, for example, 3- to 12-membered rings include 3 member ring, 4-membered ring, 5-membered ring, 6-membered ring, 7-membered ring, 8-membered ring, 9-membered ring, 10-membered ring, 11-membered ring and 12-membered ring, also includes any range from n to n+m, for example, 3- to 12-membered rings include 3- to 6-membered ring, 3- to 9-membered ring, 5- to 6-membered ring, 5- to 7-membered ring, 6- to 7-membered ring, 6- to 8-membered ring, and 6- to 10-membered ring, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present disclosure can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present disclosure.

All of the solvents used in the present disclosure are commercially available. This present disclosure adopts the abbreviating words as follows: aq refers to aqueous; HATU refers to O-(7-azabenzotriazol-1-yl)-N,N,N',N'-tetramethyluronium hexafluorophosphate; EDC refers to N-(3-dimethylaminopropyl)-N'-ethylcarbodiimide hydrochloride; m-CPBA refers to 3-chloroperoxybenzoic acid; eq refers to equivalent; CDI refers to carbonyldiimidazole; DCM refers to dichloromethane; PE refers to petroleum ether; DIAD refers to diisopropyl azodiformate; DMF refers to N,N-dimethylformamide; DMSO refers to dimethyl sulfoxide; EtOAc refers to ethyl acetate; EtOH refers to ethanol; MeOH refers to methanol; CBz refers to benzyloxycarbonyl, which is a protecting group for amine; BOC refers to t-butyloxycarbonyl, which is a protecting group for amine; HOAc refers to acetic acid; $NaCNBH_3$ refers to sodium cyanoborohydride; r.t. refers to room temperature; O/N refers to overnight; THF refers to tetrahydrofuran; $Boc_2O$ refers to di-tert-butyl dicarbonate; TFA refers to trifluoroacetic acid; DIPEA refers to ethyldiisopropylamine; $SOCl_2$ refers to thionyl chloride; $CS_2$ refers to carbon disulfide; TsOH refers to p-toluenesulfonic acid; NFSI refers to N-fluoro-N-(benzenesulfonyl)benzenesulfonamide; NCS refers to 1-chloropyrrolidine-2,5-dione; n-$Bu_4NF$ refers to tetrabutylammonium fluoride; iPrOH refers to 2-propanol; mp refers to melting point; LDA refers to lithium diisopropylamide; PPA refers to polyphosphoric acid; $PPh_3$ refers to triphenylphosphine; $Pd(PPh_3)_4$ refers to tetrakis(triphenylphosphine) palladium.

Compounds are named manually or by ChemDraw® software, the commercially available compounds use their vendor directory names.

Figure 1:
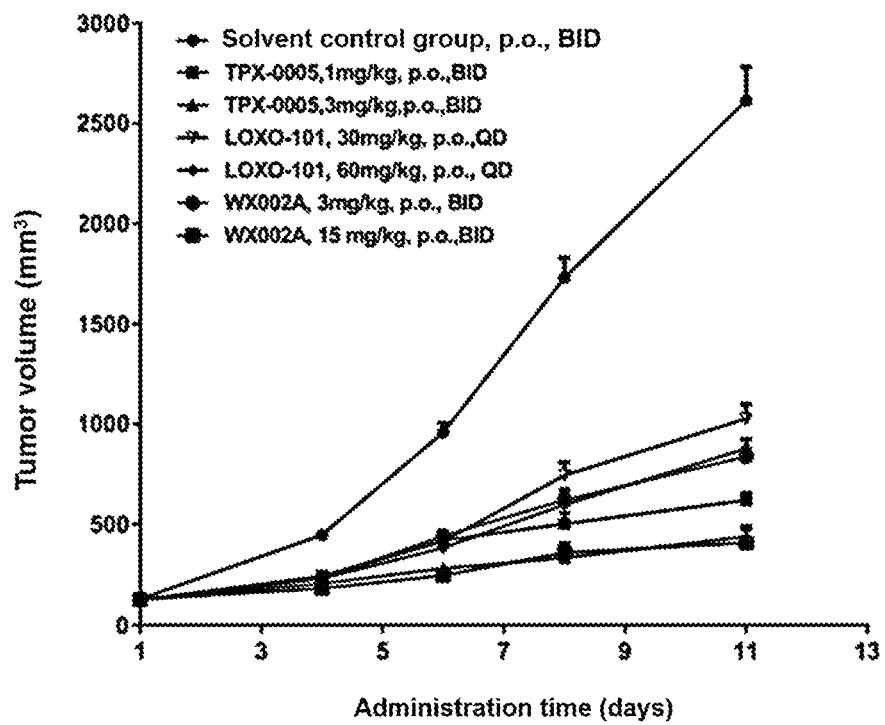
FIG. 1: transplanted tumor model of human colon cancer KM12 in nude mice.

PO stands for oral administration; QD stands for once a day; BID stands for twice a day.

DETAILED DESCRIPTION OF THE EMBODIMENT

The following examples further illustrate the present disclosure, but the present disclosure is not limited thereto. The present disclosure has been described in detail in the text, and its specific embodiments have also been disclosed, for one skilled in the art, it is obvious to modify and improve the embodiments of the present disclosure within the spirit and scope of the present disclosure.

Example 1: Synthesis of WX001

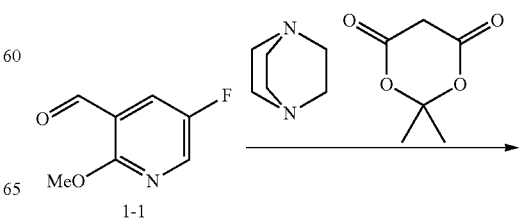

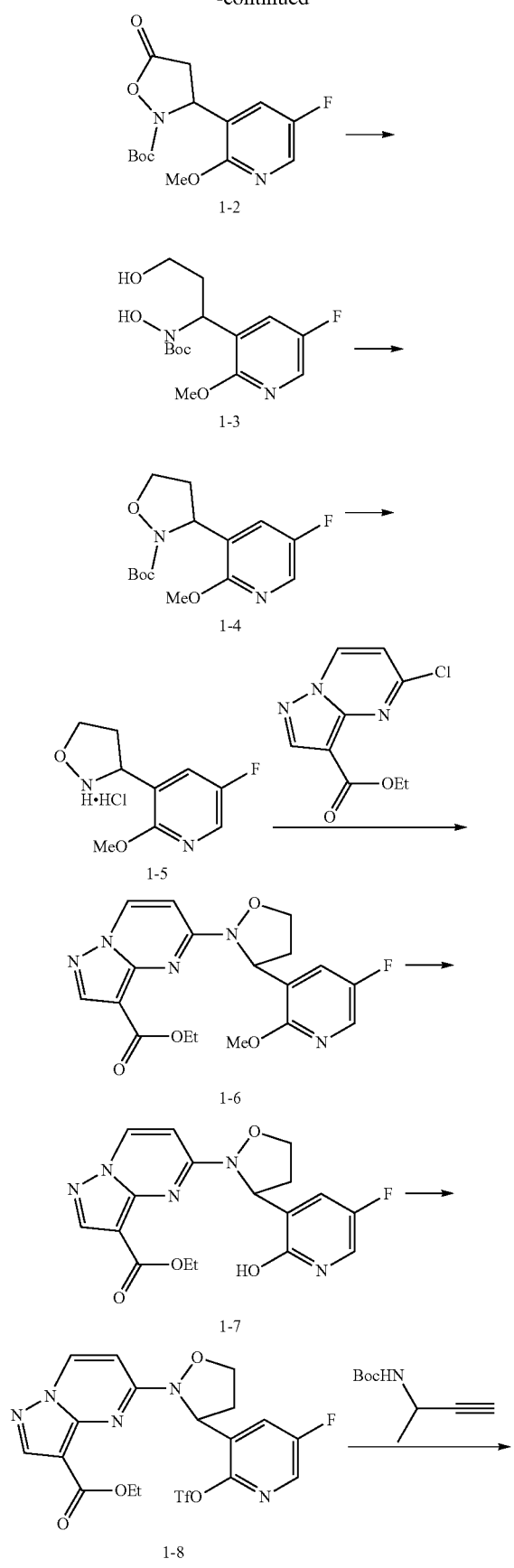
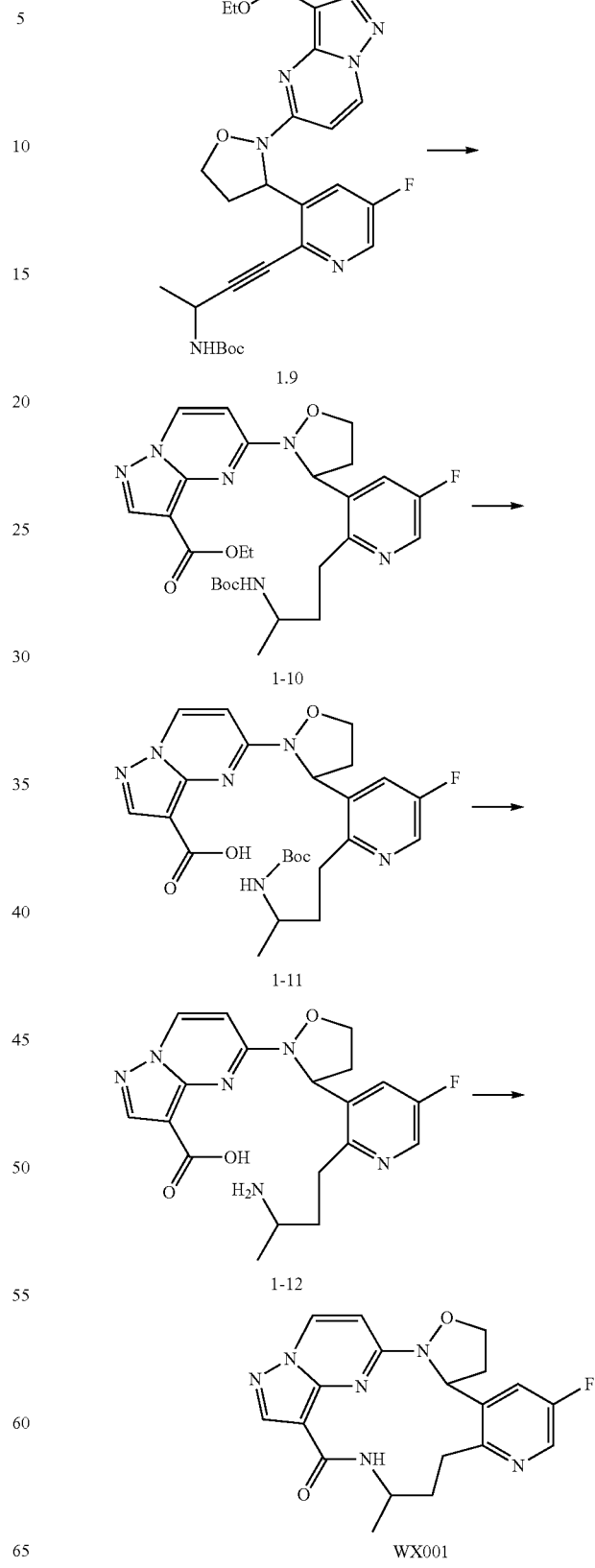

Step 1: Synthesis of Compound 1-2

Compound 1-1 (15 g, 96.70 mmol, 1 eq) was dissolved in ethyl acetate (300 mL), followed by addition of isopropylidene malonate (13.94 g, 96.70 mmol, 1 eq), triethylene diamine (1.08 g, 9.67 mmol, 1.06 mL, 0.1 eq) and tert-butyl N-hydroxycarbamate (12.87 g, 96.70 mmol, 1 eq). The obtained reaction mixture was stirred at 25° C. for 16 hours. The reaction mixture was washed twice with water (200 mL each time), and then washed once with 100 mL saturated brine. The organic phase was dried over anhydrous sodium sulfate, the desiccant was removed by filtration, and the solvent was removed from the filtrate under reduced pressure to obtain a crude product. The crude product was purified by column chromatography (petroleum ether:ethyl acetate=3:1) to obtain compound 1-2. $^1$H NMR (400 MHz, CDCl$_3$) δ: 7.98 (d, J=2.8 Hz, 1H), 7.52-7.48 (m, 1H), 5.65 (dd, J=3.6, 10.0 Hz, 1H), 3.95 (s, 3H), 3.33 (dd, J=9.6, 18.0 Hz, 1H), 2.74 (dd, J=3.6, 16.0 Hz, 1H), 1.50 (s, 9H). LCMS m/z=313.3 [M+H]$^+$.

Step 2: Synthesis of Compound 1-3

Compound 1-2 (21.40 g, 68.53 mmol, 1 eq) was dissolved in tetrahydrofuran (300 mL), and lithium borohydride (4.48 g, 205.58 mmol, 3 eq) was slowly added, and stirred at 25° C. for 0.1 hour. 200 mL of water was added to the reaction mixture, and then extracted twice with ethyl acetate (50 mL each time). The organic phases were combined and washed with 100 mL of saturated brine, then dried over anhydrous sodium sulfate, filtered to remove the desiccant, and the filtrate was concentrated to dryness by rotary evaporation to obtain the crude compound 1-3. $^1$H NMR (400 MHz, CDCl$_3$) δ: 7.88 (d, J=3.2 Hz, 1H), 7.67-7.64 (dd, J=2.8, 8.8 Hz, 1H), 5.46-5.42 (m, 1H), 3.91 (s, 3H), 3.86-3.71 (m, 2H), 2.24-2.14 (m, 1H), 2.08-2.00 (m, 1H), 1.41 (s, 9H). LCMS m/z=317.3[M+H]$^+$.

Step 3: Synthesis of Compound 1-4

Compound 1-3 (14.52 g, 45.90 mmol, 1 eq) and triphenylphosphine (30.10 g, 114.76 mmol, 2.5 eq) were dissolved in tetrahydrofuran (150 mL), and the obtained reaction mixture was cooled to 5° C. in an ice-water bath, followed by dropwise addition of diisopropyl azodicarboxylate (27.85 g, 137.71 mmol, 26.77 mL, 3 eq). After the dropwise addition, the ice-water bath was removed, and the mixture was stirred at 25° C. for 0.1 hour. The reaction mixture was concentrated to dryness by rotary evaporation, and the residue was purified by column chromatography (petroleum ether:ethyl acetate=50:1 to 30:1 to 10:1 to 5:1) to obtain compound 1-4. $^1$H NMR (400 MHz, CDCl$_3$) δ: 7.88 (d, J=3.2 Hz, 1H), 7.52-7.50 (m, 1H), 5.38-5.35 (m, 1H), 4.13-4.03 (m, 1H), 3.94 (s, 3H), 3.89-3.82 (m, 1H), 2.84-2.76 (m, 1H), 2.12-2.03 (m, 1H), 1.50 (s, 9H). LCMS m/z=299.3[M+H]$^+$.

Step 4: Synthesis of Compound 1-5

Compound 1-4 (3.00 g, 10.06 mmol, 1 eq) was dissolved in a solution of hydrogen chloride in methanol (4 M, 12.57 mL, 5 eq) and stirred at 25° C. for 3 hours. The reaction mixture was concentrated to dryness by rotary evaporation and compound 1-5 was obtained. $^1$H NMR (400 MHz, CD$_3$OD) δ: 8.17 (d, J=2.8 Hz, 1H), 7.81-7.79 (m, 1H), 5.21 (t, J=8.0 Hz, 1H), 4.60-4.54 (m, 1H), 4.40-4.32 (m, 1H), 4.04 (s, 3H), 2.96-2.80 (m, 2H). LCMS m/z=199.3 [M+H]$^+$.

Step 5: Synthesis of Compound 1-6

Ethyl 5-chloropyrazolo[1,5-a]pyrimidine-3-carboxylate (1.92 g, 8.52 mmol, 1 eq), compound 1-5 (2.20 g, 9.38 mmol, 1.1 eq) and n-butanol (5 mL) were added into a reaction flask, and then N,N-diisopropylethylamine (6.61 g, 51.14 mmol, 8.91 mL, 6 eq) was added, and the obtained reaction mixture was stirred at 90° C. for 3.5 hours. The reaction mixture was concentrated, 30 mL of water was added, and then extracted with 30 mL of ethyl acetate. The organic phase was separated, washed once with 20 mL of saturated brine, then dried over anhydrous sodium sulfate, and filtered to remove the desiccant. The solvent was removed from the filtrate under reduced pressure to obtain a crude product, which was purified by column chromatography (petroleum ether:ethyl acetate=100:0 to 10:1 to 5:1 to 2:3) to obtain compound 1-6. $^1$H NMR (400 MHz, CDCl$_3$) δ: 8.48 (d, J=7.6 Hz, 1H), 8.39 (s, 1H), 7.92 (d, J=3.2 Hz, 1H), 7.58-7.55 (m, 1H), 7.03 (d, J=7.6 Hz, 1H), 6.06 (dd, J 5.2, 8.8 Hz, 1H), 4.33-4.24 (m, 2H), 4.22-4.18 (m, 1H), 4.01 (s, 3H), 3.93-3.87 (m, 1H), 2.94-2.90 (m, 1H), 2.36-2.30 (m, 1H), 1.27 (t, J=6.8 Hz, 3H). LCMS m/z=388.3 [M+H]$^+$.

Step 6: Synthesis of Compounds 1-7

Compound 1-6 (3.9 g, 10.07 mmol, 1 eq) was dissolved in acetonitrile (100 mL), sodium iodide (4.53 g, 30.20 mmol, 3 eq) was added, and trimethylchlorosilane (3.28 g, 30.20 mmol, 3.83 mL, 3 eq) was added dropwise under stirring. After the dropwise addition, the obtained reaction mixture was stirred and refluxed at 75° C. for 0.5 hour under nitrogen atmosphere. 50 mL of water was added to the reaction mixture and then a solid precipitated. The mixture was filtered, and the filter cake was dried under vacuum at 40° C. to obtain compound 1-7. $^1$H NMR (400 MHz, CD$_3$OD) δ: 8.69 (d, J=7.6 Hz, 1H), 8.30 (s, 1H), 7.63-7.60 (m, 1H), 7.38 (t, J=3.2 Hz, 1H), 7.10 (d, J 5.6, 1H), 5.79-5.75 (m, 1H), 4.26-4.19 (m, 2H), 2.98-2.90 (m, 1H), 2.35-2.29 (m, 1H), 1.25 (t, J=7.2 Hz, 3H). LCMS m/z=374.3 [M+H]$^+$.

Step 7: Synthesis of Compounds 1-8

Compound 1-7 (0.6 g, 1.61 mmol, 1 eq) and triethylamine (442.34 mg, 4.37 mmol, 608.45 μL, 2.72 eq) were dissolved in anhydrous dichloromethane (20 mL), and cooled to 5° C. in an ice-water bath, followed by dropwise addition of trifluoromethanesulfonic anhydride (1.22 g, 4.31 mmol, 710.64 μL, 2.68 eq). After the dropwise addition, the obtained reaction mixture was naturally warmed to 25° C. and stirred for 2 hours under nitrogen atmosphere. The reaction mixture was washed with 20 mL of water and 15 mL of saturated brine, then dried over anhydrous sodium sulfate, and filtered to remove the desiccant. The filtrate was concentrated to dryness by rotary evaporation to obtain compound 1-8. $^1$H NMR (400 MHz, CDCl$_3$) δ: 8.53 (d, J=7.6 Hz, 1H), 8.43 (s, 1H), 8.14 (d, J=2.8 Hz, 1H), 7.87 (dd, J=2.8, 7.6 Hz, 1H), 7.05 (d, J=7.2 Hz, 1H), 6.10 (dd, J=5.6, 8.8 Hz, 1H), 4.37-4.24 (m, 3H), 3.95-3.88 (m, 1H), 3.12-3.04 (m, 1H), 2.50-2.41 (m, 1H), 1.28 (t, J=7.2 Hz, 3H). LCMS m/z=506.3 [M+H]$^+$.

Step 8: Synthesis of Compounds 1-9

Compound 1-8 (3.00 g, 5.94 mmol, 1 eq) was dissolved in a mixture of water (60 mL) and toluene (120 mL), diisopropylamine (1.50 g, 14.84 mmol, 2.10 mL, 2.5 eq), bis(triphenylphosphine)palladium dichloride (833.28 mg, 1.19 mmol, 0.2 eq) and cuprous iodide (226.10 mg, 1.19 mmol, 0.2 eq) were added, and (R)—N-Boc-3-amino-1-butyne (4.02 g, 23.74 mmol, 4 eq) was added at last. The obtained reaction mixture was allowed to react at 100° C. for 16 hours under nitrogen atmosphere. The reaction mixture was filtered, and the filter cake was washed with 20 mL of ethyl acetate. The filtrate was separated to obtain an organic phase, which was dried over anhydrous sodium sulfate and then filtered to remove the desiccant. The filtrate was concentrated to dryness by rotary evaporation to obtain a crude product, which was purified by column chromatography (petroleum ether:ethyl acetate=10:1 to 5:1 to 1:1) to obtain compound 1-9. $^1$H NMR (400 MHz, CDCl$_3$) δ: 8.52 (d J=7.6 Hz, 1H), 8.38 (d, J=3.6 Hz 1H), 8.36-8.33 (m, 1H), 7.65-7.62 (m, 1H), 7.05 (t, J=7.6 Hz, 1H), 6.44-6.38 (m, 1H), 5.76-5.54 (brs, 1H), 4.91-4.76 (m, 1H), 4.36-4.24 (m, 2H), 3.93-3.83 (m, 1H), 3.08-3.04 (m, 1H), 2.41-2.29 (m, 1H), 1.60-1.54 (m, 3H), 1.43 (s, 9H), 1.32-1.29 (m 3H). LCMS m/z=525.5[M+H]$^+$.

Step 9: Synthesis of Compound 1-10

Compound 1-9 (1.1 g, 2.10 mmol, 1 eq) was dissolved in ethanol (20 mL), and palladium/carbon (2.10 mmol, 10% purity, 1 eq) and sodium carbonate (444 mg, 4.19 mmol, 2 eq) were added. The reaction mixture was purged with hydrogen, and then stirred at 25° C. for 1.5 hours under hydrogen atmosphere at a pressure of 15 psi. The reaction mixture was filtered, and the filtrate was concentrated to dryness by rotary evaporation to obtain 712 mg of crude product. The crude product was purified by preparative plate (petroleum ether:ethyl acetate=1:1.5) to obtain compound 1-10, which was directly used in the reaction of next step. LCMS m/z=529.5 [M+H]$^+$.

Step 10: Synthesis of Compound 1-11

Compound 1-10 (10 mg, 18.92 µmol, 1 eq) was dissolved in methanol (1 mL), and then a prepared sodium hydroxide solution (3 M, 37.84 µL, 6 eq) and water (0.04 mL) were added. The resulting reaction mixture was stirred at 60° C. for 1.5 hours. The above reaction was conducted in octuplicate, and the 8 batches of reaction mixture were combined together, neutralized with 1 mol/L dilute hydrochloric acid until the pH value was 7, and then concentrated to dryness by rotary evaporation to obtain a crude product. The crude product was purified by high performance preparative chromatography to obtain compound 1-11. LCMS m/z=501.2 [M+H]$^+$, 401.4[M−100+H]$^+$.

Step 11: Synthesis of Compound 1-12

Compound 1-11 (8.6 mg, 17.18 µmol, 1 eq) was dissolved in a solution of hydrogen chloride in ethyl acetate (3 M, 0.6 mL, 104.76 eq), and stirred at 20° C. for 1 hour. The reaction was conducted in duplicate, and the 2 batches of reaction mixture were combined, and concentrated to dryness by rotary evaporation to obtain a crude product of compound 1-12, which was directly used in the reaction of next step. LCMS m/z=401.3 [M+H]$^+$.

Step 12: Synthesis of Compound WX001

Compound 1-12 (13.8 mg, 34.47 µmol, 1 eq) was dissolved in N,N-dimethylformamide (5 mL), followed by addition of pentafluorophenyl diphenylphosphate (19.86 mg, 51.70 µmol, 1.5 eq) and then N,N-diisopropylethylamine (11.14 mg, 86.16 µmol, 15.01 µL, 2.5 eq). The reaction mixture was stirred at 25° C. for 1 hour. 30 mL of dichloromethane was added to the reaction mixture, and then washed with water (10 mL×3). The organic phase was concentrated to dryness by rotary evaporation and the residue was dissolved in 130 mL of methyl tert-butyl ether, and then washed with water (10 mL×3). The organic phase was concentrated to obtain a crude product. The crude product was separated by HPLC (hydrochloric acid system) to obtain a hydrochloride of compound WX001. $^1$H NMR (400 MHz, CD$_3$OD) δ: 8.83 (s, 1H), 8.79 (d, J=7.2 Hz, 1H), 8.29 (s, 1H), 7.05 (d, J=7.2 Hz, 1H), 6.24-6.21 (m, 1H), 4.63 (t, J=7.2 Hz, 1H), 4.30-4.25 (m, 1H), 3.96-4.03 (m, 1H), 3.84-3.78 (m, 1H), 3.35-3.30 (m, 2H), 3.20-3.13 (m, 1H), 2.50-2.69 (m, 2H), 2.04-1.99 (m, 1H), 1.44 (d, J=6.4 Hz, 3H). LCMS m/z=385.2 [M+H]$^+$.

The hydrochloride of compound 001 was dissolved in methanol, and a basic resin (model: Amberlite IRA-400) was added under stirring. After 0.5 hour, the mixture was basic determined by pH test, and was filtered to remove the resin and directly concentrated to dryness to obtain compound WX001.

Example 2-4: Synthesis of WX002, WX002A and WX002B

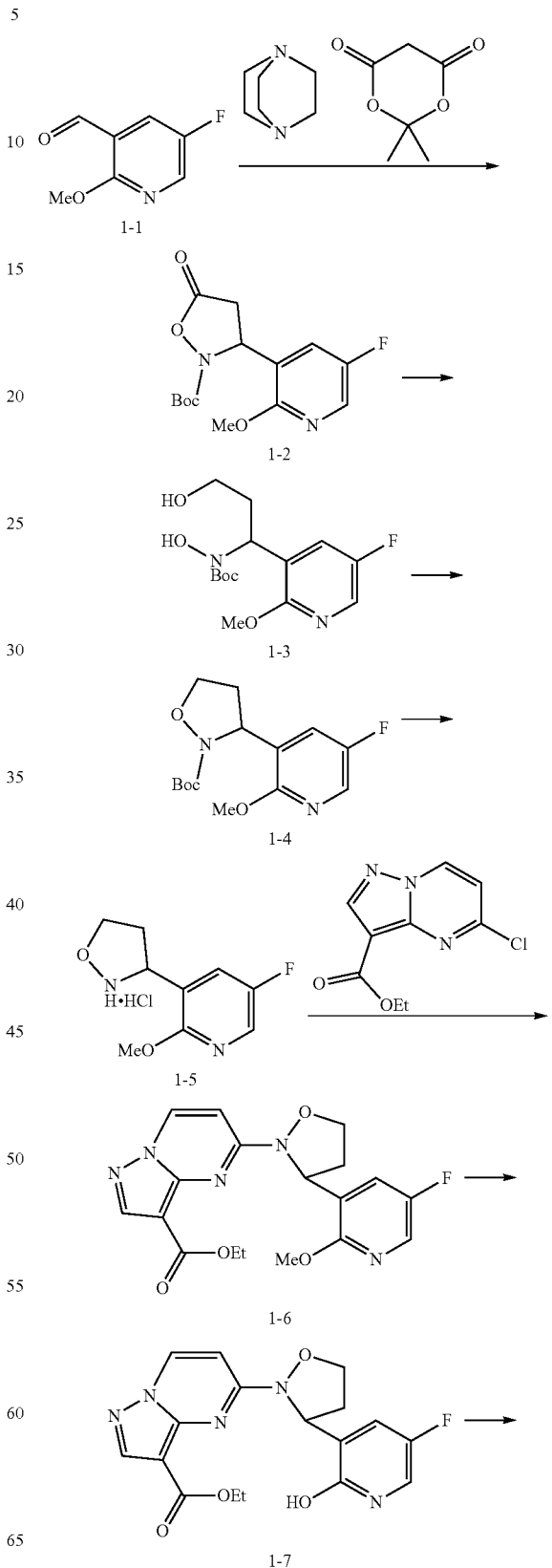

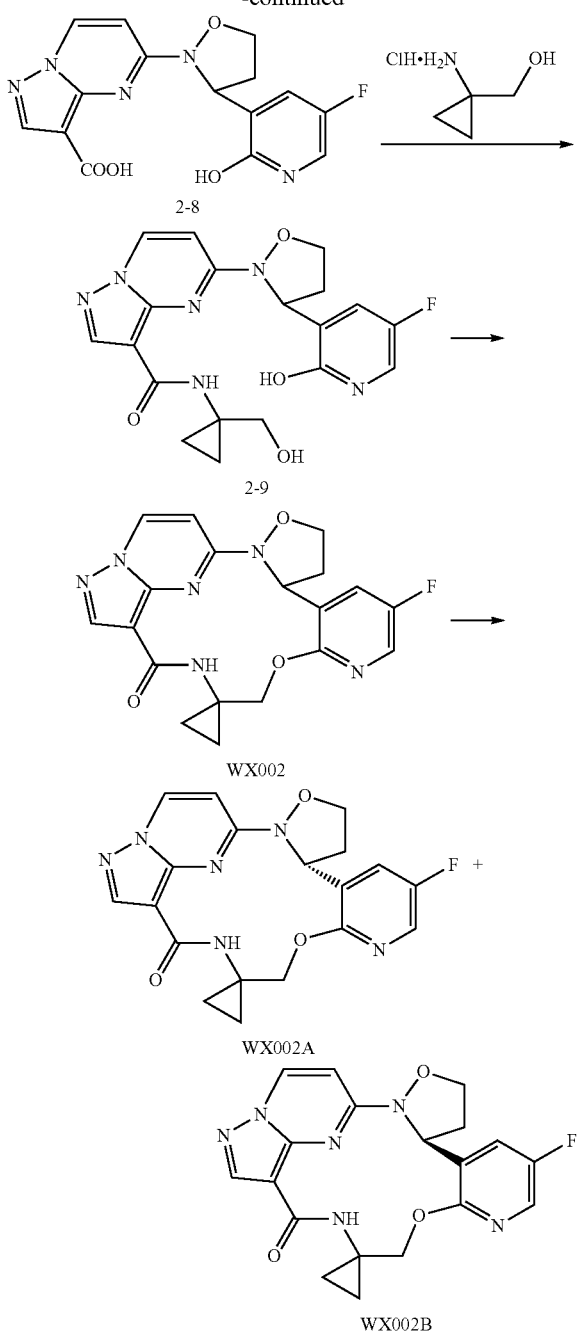

Steps 1-6: Compounds 1-2 to 1-7 were Synthesized by Steps Similar to the Step 1 to Step 6 in Example 1

Step 7: Synthesis of Compound 2-8

Compound 1-7 was dissolved in methanol (30 mL), and a prepared solution of sodium hydroxide (385.68 mg, 9.64 mmol, 4 eq) in water (3 mL) was added. The resulting reaction mixture was stirred at 60° C. under nitrogen atmosphere for 16 hours. The reaction mixture was cooled to room temperature, and the pH value was adjusted to about 7 with 2M hydrochloric acid solution. The mixture was directly concentrated to dryness by rotary evaporation to obtain compound 2-8, which was directly used in the next step. LCMS m/z=346.2 [M+H]$^+$.

Step 8: Synthesis of Compound 2-9

Compound 2-8 was dissolved in N,N-dimethylformamide (8 mL), then N,N-diisopropylethylamine (449.36 mg, 3.48 mmol, 605.60 μL, 3.5 eq) and O-(7-azabenzotriazol-1-yl)-N,N,N',N'-tetramethyluronium hexafluorophosphate (453.26 mg, 1.19 mmol, 1.2 eq) were added and stirred for 0.5 hour, and then (1-(hydroxymethyl)cyclopropylamino hydrochloride (159.59 mg, 1.29 mmol, 1.3 eq, HCl) was added. The resulting reaction mixture was allowed to react at 25° C. for 3 hours. The reaction mixture was poured into 80 mL of saturated aqueous solution of ammonium chloride, then extracted with dichloromethane (60 mL×3). The organic phases were combined and washed with saturated brine (60 mL×3), dried over anhydrous sodium sulfate in an appropriate amount, filtered to remove the desiccant, and the filtrate was concentrated to obtain a crude product. 2 mL of water was added to the crude product, and then freeze-dried to obtain compound 2-9, which was directly used in the reaction of next step. LCMS m/z=415.3 [M+H]$^+$.

Step 9: Synthesis of Compounds WX002A and WX002B

Compound 2-9 (200 mg, 482.64 μmol, 1 eq) was dissolved in tetrahydrofuran (2 mL), then tri-n-butylphosphine (195.29 mg, 965.28 μmol, 238.16 μL, 2 eq) was added, the resulting reaction mixture was cooled to 0° C. 1,1'-(azodicarbonyl)dipiperidine (243.55 mg, 965.28 μmol, 2 eq) was added, and the resulting reaction mixture was allowed to react at 25° C. for 4 hours. The above reaction was conducted in duplicate, and the 2 batches of reaction mixture were combined and then directly concentrated to dryness. The residue was purified by flash silica gel column chromatography (petroleum ether/ethyl acetate=0 to 90%) and preparative plate (ethyl acetate:methanol=10:1) to obtain compound WX002. The compound WX002 was resolved by SFC (column: DAICEL CHIRALCEL OD-H (250 mm*30 mm, 5 μm); mobile phase: A (CO$_2$) and B (methanol, containing 0.1% ammonium hydroxide); gradient: B %=32%-32%, 7.5 min, to obtain WX002A and WX002B.

WX002A: $^1$H NMR (400 MHz, CDCl$_3$) δ: 9.27 (s, 1H), 8.42 (d, J=7.6 Hz, 1H), 8.30 (s, 1H), 7.97 (d, J=2.8 Hz, 1H), 7.59-7.57 (m, 1H), 6.79 (d, J=8.0 Hz, 1H), 6.11 (t, J=8.4 Hz, 1H), 4.88 (d, J=10.8 Hz, 1H), 4.53 (t, J=8.0 Hz, 1H), 0.3.97-3.90 (m, 1H), 3.84 (d, J=10.8 Hz, 1H), 3.08-3.01 (m, 1H), 2.60-2.46 (m, 1H), 2.39-2.33 (m, 1H), 1.48-1.42 (m, 1H), 0.95-0.90 (m, 1H), 0.87-0.81 (m, 1H). LCMS m/z=397.3 [M+H]$^+$.

SFC (column: Chiralcel OD-3, 3 μm, 0.46 cm id×10 cm L; mobile phase: A (CO$_2$) and B (MeOH, containing 0.05% isopropylamine); gradient: B %=5 to 40%, 5 min; flow rate: 4.0 mL/min; wavelength: 220 nm; pressure: 100 bar, Rt=2.14 min, 100% excess of chiral isomer.

WX002B: $^1$H NMR (400 MHz, CDCl$_3$) δ: 9.27 (s, 1H), 8.41 (d, J=7.6 Hz, 1H), 8.30 (s, 1H), 7.97 (d, J=2.8 Hz, 1H), 7.59-7.56 (m, 1H), 6.79 (d, J=7.6 Hz, 1H), 6.13-6.09 (m, 1H), 4.88 (dd, J=10.8, 1.6 Hz, 1H), 4.53 (t, J=8.0 Hz, 1H), 3.97-3.90 (m, 1H), 3.84 (d, J=10.8 Hz, 1H), 3.08-3.01 (m, 1H), 2.60-2.49 (m, 1H), 2.39-2.33 (m, 1H), 1.48-1.42 (m, 1H), 0.96-0.90 (m, 1H), 0.87-0.81 (m, 1H). LCMS m/z=397.3 [M+H]$^+$.

SFC (column: Chiralcel OD-3, 3 μm, 0.46 cm id×10 cm L; mobile phase: A (CO$_2$) and B (MeOH, containing 0.05% isopropylamine); gradient: B %=5 to 40%, 5 min; flow rate: 4.0 mL/min; wavelength: 220 nm; pressure: 100 bar, Rt=2.49 min, 100% excess of chiral isomer.

Examples 5 to 6: Synthesis of Compounds WX003A and WX003B
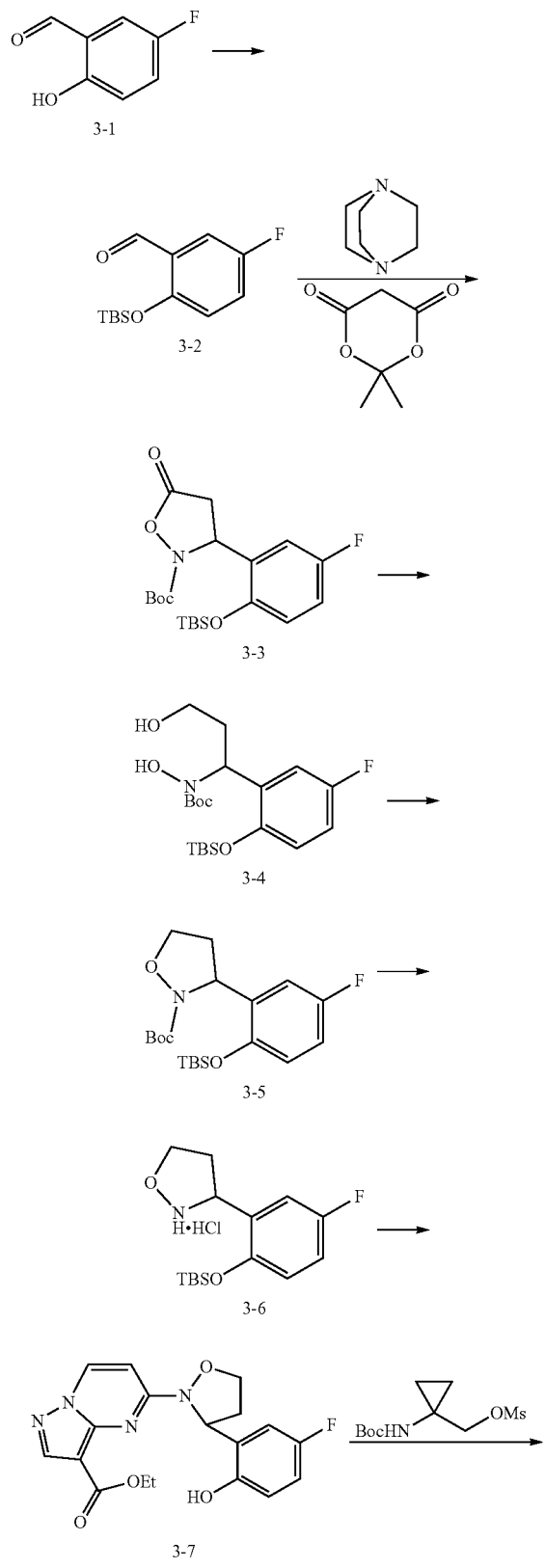
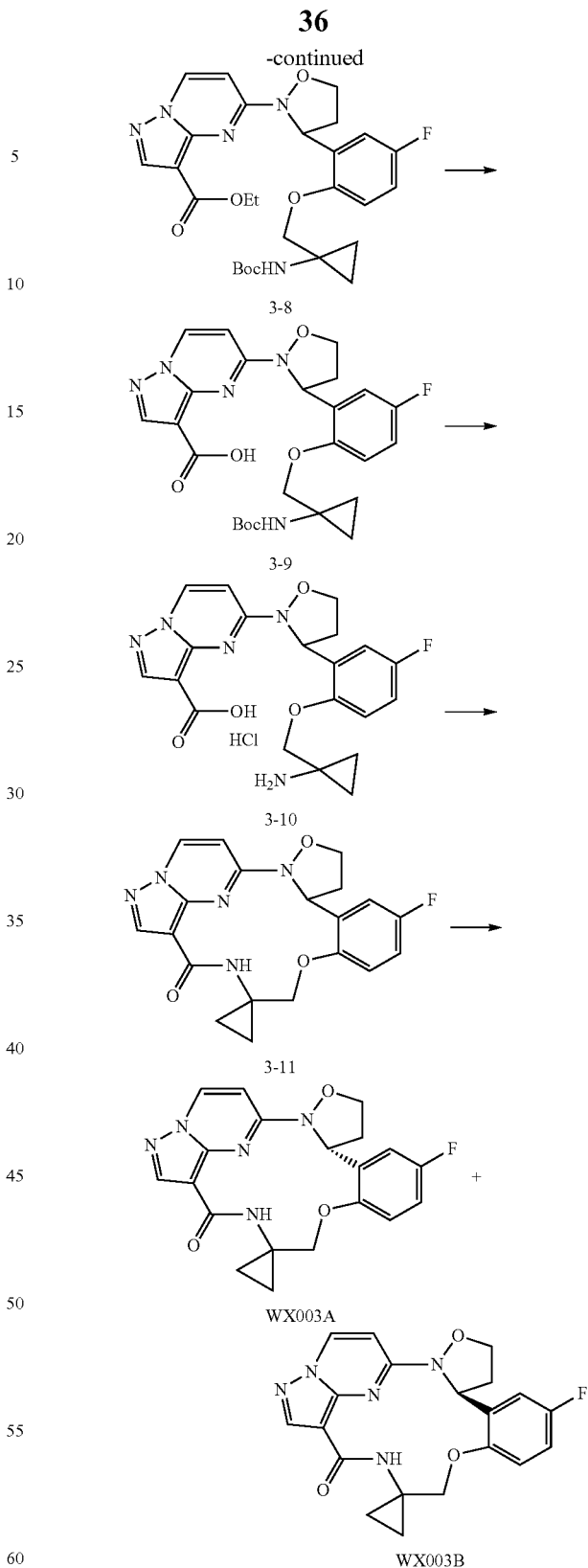
Step 1: Synthesis of Compound 3-2
Compound 3-1 (20 g, 142.74 mmol, 1 eq) and imidazole (19.44 g, 285.49 mmol, 2 eq) were dissolved in dichloromethane (250 mL), and then a solution of tert-butyl dimethylchlorosilane (25.82 g, 171.29 mmol, 20.99 mL, 1.2 eq) in dichloromethane (30 mL) was slowly added dropwise at 0° C. After the dropwise addition, the reaction mixture was naturally warmed to 25° C. and the reaction was allowed to run for 15 hours. Additional imidazole (9.72 g, 142.74 mmol, 1 eq) and tert-butyl dimethylchlorosilane (10.76 g, 71.37 mmol, 8.75 mL, 0.5 eq) were added, and the reaction mixture was stirred at 25° C. for 12 hours. After completion of the reaction, the reaction mixture was poured into 300 mL of saturated aqueous solution of sodium bicarbonate, and then extracted with dichloromethane (300 mL each time). The organic phases were combined and washed with saturated brine (200 mL×3). The organic phase was dried over an appropriate amount of anhydrous sodium sulfate, filtered to remove the desiccant, and concentrated to dryness to obtain a crude product. The crude product was purified by column chromatography to obtain compound 3-2. $^1$H NMR: (400 MHz, CDCl$_3$) δ: 10.39-10.37 (m, 1H), 7.46 (dd, J=3.2, 8.0 Hz, 1H), 7.20-7.11 (m, 1H), 6.87-6.85 (m, H), 1.01 (s, 9H), 0.26 (dd, J=2.4, 3.6 Hz, 6H).

Step 2: Synthesis of Compound 3-3

Compound 3-2 was dissolved in ethyl acetate (450 mL), and then 2,2-dimethyl-1,3-dioxane-4,6-dione (13.48 g, 93.56 mmol, 1 eq), tert-butyl N-hydroxycarbamate (12.46 g, 93.56 mmol, 1 eq) and 1,4-diazabicyclo[2.2.2]octane (1.05 g, 9.36 mmol, 1.03 mL, 0.1 eq) were added. The resulting reaction mixture was stirred at 25° C. for 18 hours under nitrogen atmosphere. After completion of the reaction, the reaction mixture was washed with water (50 mL) and saturated brine (50 mL×2). The organic phase was dried over an appropriate amount of anhydrous sodium sulfate. The desiccant was removed by filtration, and the filtrate was concentrated to dryness to obtain a crude yellow oily product. The crude product was purified by column chromatography to obtain compound 3-3.

$^1$H NMR: (400 MHz, CDCl$_3$) δ: 7.16 (dd, J=3.2, 9.2 Hz, 1H), 6.92-6.87 (m, 1H), 6.77 (dd, J=4.8, 8.8 Hz, 1H), 5.75 (dd, J=3.2, 9.6 Hz, 1H), 3.31-3.25 (m, 1H), 2.71 (dd, J=3.2, 17.6 Hz, 1H), 1.51 (s, 9H), 1.01 (s, 9H), 0.27 (d, J=12.4 Hz, 6H). LCMS m/z=434 [M+23]$^+$, 311.9 [M−100+H]$^+$.

Step 3: Synthesis of Compound 3-4

Compound 3-3 (2.01 g, 4.88 mmol, 1 eq) was dissolved in tetrahydrofuran (20 mL), then lithium borohydride (319.18 mg, 14.65 mmol, 3 eq) was added, and the resulting reaction mixture was stirred at 12° C. for 0.5 hour. After completion of the reaction, 10 mL of saturated solution of ammonium chloride was slowly added to the reaction mixture to quench the reaction. The mixture was stirred for 20 minutes, and then extracted with ethyl acetate (50 mL×3). The organic phases were combined, dried over an appropriate amount of anhydrous sodium sulfate, filtered to remove the desiccant, and the filtrate was concentrated to dryness to obtain compound 3-4. $^1$H NMR (400 MHz, CDCl$_3$) δ: 7.50 (br s, 1H), 7.42-7.32 (m, 1H), 6.87-6.77 (m, 1H), 6.76-6.63 (m, 1H), 5.53-5.42 (m, 1H), 3.90-3.71 (m, 2H), 3.25 (br s, 1H), 2.32-2.16 (m, 1H), 2.10-2.01 (m, 1H), 1.44-1.36 (m, 9H), 1.07-0.98 (m, 9H), 0.27 (d, J=1.2 Hz, 6H). LCMS m/z=438.1 [M+23]$^+$, 316 [M−100+H]$^+$.

Step 4: Synthesis of Compound 3-5

Compound 3-4 (23 g, 55.35 mmol, 1 eq) and triphenylphosphine (36.29 g, 138.36 mmol, 2.5 eq) were dissolved in anhydrous tetrahydrofuran (300 mL), and the resulting solution was cooled to 0-5° C., followed by dropwise addition of diisopropyl azodicarboxylate (33.57 g, 166.04 mmol, 32.28 mL, 3 eq). After the dropwise addition, the ice bath was removed, and the reaction was allowed to run at 25° C. for 4 hours. After completion of the reaction, the reaction mixture was filtered and the filtrate was concentrated to dryness to obtain a yellow oily liquid. 120 mL of a mixed solvent (ethyl acetate/petroleum ether=1:8) was added thereto, and the obtained mixture was stirred evenly, allowed to stand, and then filtered, the filter cake was rinsed with 50 mL of a mixed solvent (ethyl acetate/petroleum ether=8:1). The filtrate was collected and concentrated to dryness to obtain a crude product. The crude product was purified by column chromatography to obtain compound 3-5. $^1$H NMR (400 MHz, CDCl$_3$) δ: 7.17 (dd, J=3.2, 9.6 Hz, 1H), 6.87-6.75 (m, 1H), 6.74-6.66 (m, 1H), 5.43 (dd, J=4.4, 8.4 Hz, 1H), 4.08-4.02 (m, 1H), 3.92 (q, J=8.0 Hz, 1H), 2.83-2.68 (m, 1H), 2.19-2.08 (m, 1H), 1.47 (s, 9H), 1.03 (s, 9H), 0.26 (d, J=10.8 Hz, 6H). LCMS m/z=420.0 [M+23]$^+$, 297.9 [M−100+H]$^+$.

Step 5: Synthesis of Compound 3-6

Compound 3-5 (2.03 g, 5.11 mmol, 1 eq) was dissolved in ethyl acetate (20 mL), a solution of hydrogen chloride in ethyl acetate (4 M, 7.66 mL, 6 eq) was added, and the resulting reaction mixture was stirred at 14° C. for 5 hours. After completion of the reaction, the reaction mixture was concentrated to dryness to obtain a crude product. The crude product was fully dispersed in a mixed solution (10 mL) of ethyl acetate/petroleum ether (10:1), the solid was collected by filtration, and dried under vacuum at 40° C. to obtain compound 3-6. $^1$H NMR: (400 MHz, DMSO-d$_6$) δ: 7.32-7.26 (m, 1H), 7.18-7.05 (m, 1H), 7.00-6.88 (m, 1H), 5.03-4.93 (m, 1H), 4.36-4.26 (m, 1H), 4.15-4.05 (m, 1H), 2.84-2.71 (m, 1H), 2.42-2.29 (m, 1H), 1.00 (s, 9H), 0.27 (d, J=3.2 Hz, 6H). LCMS m/z=297.9 [M+H]$^+$.

Step 6: Synthesis of Compound 3-7

Compound 3-6 (1.43 g, 4.28 mmol, 1 eq) and ethyl 5-chloropyrazolo[1,5-a]pyrimidine-3-carboxylate (1.06 g, 4.71 mmol, 1.1 eq) were added into dimethyl sulfoxide (15 mL), followed by addition of triethylamine (1.30 g, 12.85 mmol, 1.79 mL, 3 eq). The resulting reaction mixture was allowed to react at 75° C. for 18 hours under nitrogen atmosphere. After completion of the reaction, the reaction mixture was concentrated to dryness. The residue was dissolved in 200 mL of ethyl acetate, and then washed with water (30 mL×3) and saturated brine (30 mL). The organic phase was dried over an appropriate amount of anhydrous sodium sulfate, filtered to remove the desiccant, and the filtrate was concentrated to dryness to obtain a crude product as yellow solid. To the crude product was added 10 mL of ethyl acetate and 10 mL of petroleum ether, and the obtained mixture was slurried, and filtered to obtain the solid. The solid was dried under vacuum at 40° C. to obtain compound 3-7. $^1$H NMR: (400 MHz, CDCl$_3$) δ: 8.55 (s, 1H), 8.39 (d, J=8.0 Hz, 1H), 8.33 (s, 1H), 7.10-7.01 (m, 2H), 6.95-6.91 (m, 1H), 6.85 (d, J=7.6 Hz, 1H), 5.97 (t, J=7.2 Hz, 1H), 4.58-4.38 (m, 3H), 4.04-3.93 (m, 1H), 2.97-2.71 (m, 2H), 1.41 (t, J=7.2 Hz, 3H). LCMS m/z=373.0 [M+H]$^+$.

Step 7: Synthesis of Compound 3-8

Compound 3-7 (300 mg, 805.69 μmol, 1 eq), (1-tert-butoxycarbonylamino)cyclopropyl methyl methanesulfonate (277.90 mg, 1.05 mmol, 1.3 eq) and cesium carbonate (525.02 mg, 1.61 mmol, 2 eq) were added into N,N-dimethylformamide (2 mL), and the resulting reaction mixture was stirred at 80° C. for 5 hours. After completion of the reaction, the reaction mixture was cooled to room temperature, diluted with ethyl acetate (200 mL), and filtered through diatomite. The filtrate was washed with water (20 mL×3). The organic phase was dried over an appropriate amount of anhydrous sodium sulfate, and filtered to remove the desiccant, and the filtrate was concentrated to dryness to obtain a crude product. The crude product was purified by column chromatography to obtain compound 3-8. $^1$H NMR (400 MHz, CDCl$_3$) δ: 8.45 (d, J=7.6 Hz, 1H), 8.34 (s, 1H), 7.21 (dd, J=2.9, 9.2 Hz, 1H), 7.02 (d, J=7.6 Hz, 1H), 6.94-6.87 (m, 1H), 6.84-6.78 (m, 1H), 6.30-6.22 (m, 1H), 5.91 (br s, 1H), 4.38-4.25 (m, 2H), 4.19-4.01 (m, 2H), 3.97-3.80 (m, 1H), 2.95-2.82 (m, 1H), 2.48-2.37 (m, 1H), 1.70-1.57 (m, 14H), 1.07-0.78 (m, 4H). LCMS m/z=542.3 [M+H]$^+$.

Step 8: Synthesis of Compound 3-9

Compound 3-8 (150 mg, 276.97 μmol, 1 eq) was dissolved in methanol (3 mL), then sodium hydroxide solution (2 M, 830.92 μL, 6 eq) was added, and the resulting reaction mixture was stirred at 60° C. for 18 hours. After completion of the reaction, the reaction mixture was concentrated to dryness, and the residue was added with water (5 mL) and stirred until completely dissolved. The pH value of the obtained solution was adjusted to 4-5 with 1 M hydrochloric acid, and then the mixture was extracted with ethyl acetate (20 mL×3). The organic phases were combined, dried over an appropriate amount of anhydrous sodium sulfate, and filtered to remove the desiccant. The filtrate was concentrated to dryness to obtain a crude product of compound 3-9. LCMS m/z=514.1 [M+H]$^+$.

Step 9: Synthesis of Compound 3-10

Compound 3-9 (143 mg, 278.47 μmol, 1 eq) was dissolved in ethyl acetate (3 mL), and then a solution of hydrogen chloride in ethyl acetate (4 M, 69.62 μL, 1 eq) was added. The resulting reaction mixture stirred at 13° C. for 18 hours. After completion of the reaction, the reaction mixture was concentrated to dryness to obtain product 3-10. LCMS m/z=414.1 [M+H]$^+$.

Step 10: Synthesis of Compound 3-11

Compound 3-10 (128 mg, 309.63 μmol, 1 eq) and N,N-diisopropylethylamine (200.09 mg, 1.55 mmol, 269.66 μL, 5 eq) were added into a mixed solvent of dichloromethane (20 mL) and N,N-dimethylformamide (4 mL), followed by addition of pentafluorophenyl diphenylphosphinate (154.66 mg, 402.51 μmol, 1.3 eq). The resulting reaction mixture was stirred at 25° C. for 4 hours. After completion of the reaction, 3M aqueous solution of sodium carbonate (3 mL) was added to the reaction mixture and stirred for 5 minutes, and then extracted and ethyl acetate (100 mL). The aqueous layer was discarded, the organic phase was washed with saturated brine (15 mL×3), then dried over an appropriate amount of anhydrous sodium sulfate, filtered to remove the desiccant, and the filtrate was concentrated to dryness to obtain a brown oily liquid. The crude product was purified by column chromatography (ethyl acetate/petroleum ether=0 to 45%) to obtain compound 3-11. LCMS m/z=396.1 [M+H]$^+$.

Step 11: Synthesis of Compounds WX003A and WX003B

Compound 3-11 (180 mg, 455.25 μmol, 1 eq) was resolved by supercritical fluid chromatography (SFC) (column: Phenomenex-Amylose-1 (250 mm*30 mm, 5 μm); mobile phase: A (CO$_2$) and B (ethanol, containing 0.1% ammonium hydroxide); gradient: B %=40%-40%, 10 min) to obtain compounds WX003A and WX003B.

WX003A: $^1$H NMR (400 MHz, CDCl$_3$) δ: 9.51 (s, 1H), 8.40 (d, J=7.2 Hz, 1H), 8.30 (s, 1H), 7.21 (dd, J=3.2, 9.2 Hz, 1H), 6.99-6.93 (m, 1H), 6.83-6.75 (m, 2H), 6.37-6.30 (m, 1H), 4.53 (t, J=7.6 Hz, 1H), 4.41 (dd, J=2.0, 9.2 Hz, 1H), 3.93-3.85 (m, 1H), 3.73 (d, J=9.2 Hz, 1H), 3.08-2.97 (m, 1H), 2.65-2.53 (m, 2H), 1.32-1.28 (m, 1H), 0.93-0.82 (m, 2H). LCMS m/z=396.2 [M+H]$^+$. SFC (Column: Chiralpak AD-3 150×4.6 mm I.D., 3 μm; Mobile phase: A (CO$_2$) and B (ethanol, containing 0.05% diethylamine); gradient: B %=40%, 6 min; flow rate: 2.5 mL/min; column temperature: 35° C.), Rt=3.689 min, 100% isomer excess.

WX003B: $^1$H NMR (400 MHz, CDCl$_3$) δ: 9.51 (s, 1H), 8.40 (d, J=7.2 Hz, 1H), 8.30 (s, 1H), 7.21 (dd, J=3.2, 9.2 Hz, 1H), 6.99-6.93 (m, 1H), 6.83-6.75 (m, 2H), 6.37-6.30 (m, 1H), 4.53 (t, J=7.6 Hz, 1H), 4.41 (dd, J=2.0, 9.2 Hz, 1H), 3.93-3.85 (m, 1H), 3.73 (d, J=9.2 Hz, 1H), 3.08-2.97 (m, 1H), 2.65-2.53 (m, 2H), 1.32-1.28 (m, 1H), 0.93-0.82 (m, 2H). LCMS m/z=396.2 [M+H]$^+$. SFC (Column: Chiralpak AD-3 150×4.6 mm I.D., 3 μm; Mobile phase: A (CO$_2$) and B (ethanol, containing 0.05% diethylamine); gradient: B %=40%, 6 min; flow rate: 2.5 mL/min; column temperature: 35° C.), Rt=4.561 min, 99.74% isomer excess.

By methods similar to the synthesis methods of steps 1-9 in Example 2, the examples in the following table were synthesized. The SFC conditions of each example in the following table are the resolution conditions of chiral carbon in isoxazolyl, and the remaining chiral carbons in the structural formulas are directly introduced from the corresponding raw materials in the synthetic process.

| Example | Compound | Structure | NMR and SFC | MS m/z: [M + H]$^+$ |
|---|---|---|---|---|
| 7 | WX004A | 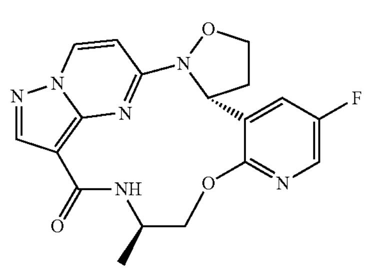 [SMILES: C[C@@H]1COc2ncc(F)cc2[C@H]2CCON2c2ccn3ncc(c3n2)C(=O)N1] | $^1$H NMR (400 MHz, CD$_3$OD) δ: 8.66 (d, J = 7.6 Hz, 1 H), 8.25 (s, 1 H), 8.01 (d, J = 2.8 Hz, 1 H), 7.77-7.74 (m, 1H), 6.91 (d, J = 8.0 Hz, 1 H), 6.08-6.03 (m, 1 H), 4.66-4.55 (m, 2 H), 4.39-4.33 (m, 2 H), 3.98-3.92 (m, 1 H), 3.09-3.03 (m, 1 H), 2.66-2.56 (m, 1 H), 1.50 (d, J = 6.4 Hz, 3 H) | 385.1 |

| Example | Compound | Structure | NMR and SFC | MS m/z: [M + H]+ |
|---|---|---|---|---|
| 8 | WX004B | 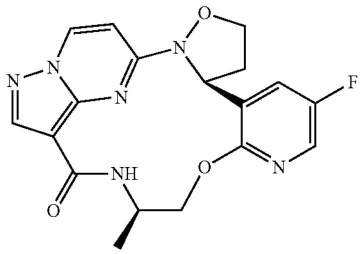 [SMILES: C[C@@H]1COc2ncc(F)cc2[C@@H]2CCON2c2ccn3ncc(c3n2)C(=O)N1] | ¹H NMR (400 MHz, CDCl₃) δ: 9.31 (s, 1 H), 8.45 (s, 1H), 8.00 (d, J = 2.4 Hz, 1 H), 7.61-7.59 (m, 1 H), 6.86 (d, J = 7.6 Hz, 1 H), 6.06 (s, 1H), 4.71-4.66 (m, 1H), 4.52 (t, J = 7.6, 14.8 Hz, 1 H), 4.36-4.26 (m, 2H), 3.83 (s, 1H), 3.43 (s, 1H), 2.99 (s, 1H), 2.53 (s, 1H), 1.61 (s, 3H). | 385.1 |
| 9 | WX005A | 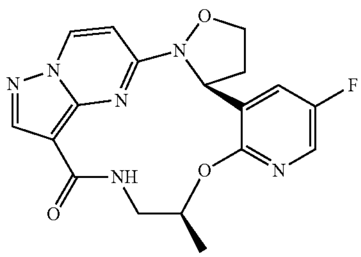 [SMILES: C[C@H]1CNC(=O)c2cnn3ccc(nc23)N2OCC[C@H]2c2cc(F)cnc2O1] | ¹H NMR (400 MHz, CDCl₃) δ: 9.20 (s, 1 H), 8.44 (d, J = 7.6 Hz, 1 H), 8.37 (s, 1 H), 7.95 (d, J = 3.2 Hz, 1 H), 7.54 (dd, J = 2.8, 8.0 Hz, 1 H), 6.81 (d, J = 12.4 Hz, 1 H), 5.98-5.94 (m, 1 H), 4.99-4.92 (m, 1 H), 4.54-4.50 (m, 1 H), 4.05-3.96 (m, 2 H), 3.94-3.78 (m, 1 H), 2.58-2.50 (m, 1H), 1.60 (d, J = 6.4 Hz, 3 H). SFC (column: Chiralpak AD-H, 5 μm, 3 cm id × 25 cm L; mobile phase: A (CO₂) and B (EtOH, containing 0.1% ammonium hydroxide); gradient: B% = 50%, flow rate: 70 g/min; wavelength: 220 nm; pressure: 100 bar., column temperature: 40° C., Rt = 4.3 min. | 385.1 |
| 10 | WX005B | 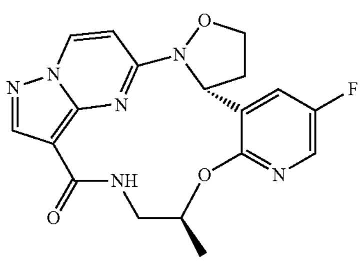 [SMILES: C[C@H]1CNC(=O)c2cnn3ccc(nc23)N2OCC[C@@H]2c2cc(F)cnc2O1] | ¹H NMR (400 MHz, CD₃OD) δ: 8.65 (d, J = 8.0 Hz, 1 H), 8.23 (s, 1 H), 8.00 (d, J = 3.2 Hz, 1 H), 7.73 (dd, J = 3.2, 8.8 Hz, 1 H), 6.89 (d, J = 7.6 Hz, 1 H), 5.94-5.90 (m, 1 H), 5.34-5.26 (m, 1 H), 4.58 (t, J = 6.8, 14.4 Hz, 1 H), 4.07-3.97 (m, 2 H), 3.40 (dd, J = 8.4, 13.6 Hz, 1 H), 3.07-3.01 (m, 1H), 2.62-2.52 (m, 1 H), 1.55 (d, J = 6.4 Hz, 3 H). SFC (column: Chiralpak AD-H, 5 μm, 3 cm id × 25 cm L; mobile phase: A (CO₂) and B (EtOH, containing 0.1% ammonium hydroxide); gradient: B% = 50%, flow rate: 70 g/min; wavelength: 220 nm; pressure: 100 bar., column temperature: 40° C., Rt = 4.97 min. | 385.1 |
| 11 | WX006A | 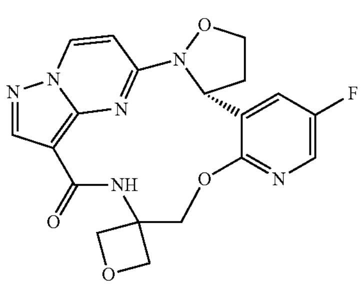 [SMILES: O=C1NC2(COC2)COc2ncc(F)cc2[C@H]2CCON2c2ccn3ncc1c3n2] | ¹H NMR (400 MHz, CDCl₃) δ: 9.17 (s, 1H), 8.45-8.41 (m, 2 H), 8.00 (d, J = 2.4 Hz, 1 H), 7.60-7.57 (m, 1 H), 6.82 (d, J = 7.6 Hz, 1 H), 5.97-5.93 (m, 2 H), 5.52 (d, J = 5.4 Hz, 1 H), 4.99 (d, J = 11.2 Hz, 1 H), 4.76 (d, J = 11.2 Hz, 1 H), 4.63 (d, J = 5.4 Hz, 2 H), 4.53 (t, J = 7.6 Hz, 1 H), 3.92-3.85 (m, 1 H), 3.04-2.98 (m, 1 H), 2.60-2.52 (m, 1 H). SFC (column: Chiralcel OD-3, 3 μm, 0.46 cm id × 10 cm L; mobile phase: A (CO₂) and B (EtOH, containing 0.05% isopropylamine); gradient: B% = 5 to 40%, 5 min; flow rate: 4.0 mL/min; wavelength: 220 nm; pressure: 100 bar, Rt = 2.7 min, chiral isomer excess 100%. | 413.1 |

| Example | Compound | Structure | NMR and SFC | MS m/z: [M + H]+ |
|---|---|---|---|---|
| 12 | WX006B | 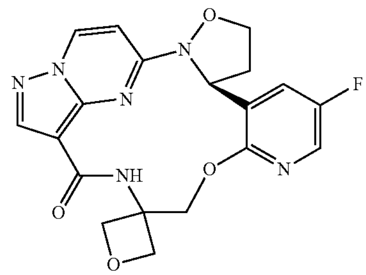 [SMILES: O=C1NC2(COC2)COc2ncc(F)cc2[C@@H]2CCON2c2ccn3ncc1c3n2] | ¹H NMR (400 MHz, CDCl₃) δ: 9.17 (s, 1H), 8.45-8.41 (m, 2 H), 8.00 (d, J = 2.4 Hz, 1 H), 7.60-7.57 (m, 1 H), 6.82 (d, J = 7.6 Hz, 1 H), 5.97-5.93 (m, 2 H), 5.52 (d, J = 5.4 Hz, 1 H), 4.99 (d, J = 11.2 Hz, 1 H), 4.76 (d, J = 11.2 Hz, 1 H), 4.63 (d, J = 5.4 Hz, 2 H), 4.53 (t, J = 7.6 Hz, 1 H), 3.92-3.85 (m, 1 H), 3.04-2.98 (m, 1 H), 2.60-2.52 (m, 1 H). SFC (column: Chiralcel OD-3, 3 μm, 0.46 cm id × 10 cm L; mobile phase: A (CO₂) and B (EtOH, containing 0.05% isopropylamine); gradient: B% = 5 to 40%, 5 min; flow rate: 4.0 mL/min; wavelength: 220 nm; pressure: 100 bar, Rt = 3.41 min, chiral isomer excess 100%. | 413.1 |
| 13 | WX007A | 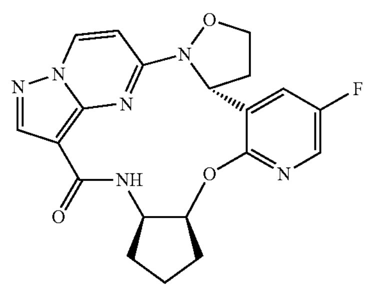 [SMILES: O=C1N[C@@H]2CCC[C@@H]2Oc2ncc(F)cc2[C@H]2CCON2c2ccn3ncc1c3n2] | ¹H NMR (400 MHz, CDCl₃) δ: 9.57 (d, J = 6.8 Hz, 1 H), 8.41 (d, J = 7.8 Hz, 1 H), 8.36 (s, 1H), 7.94 (d, J = 3.2 Hz, 1 H), 7.54 (dd, J = 8.4, 3.2 Hz, 1 H), 6.77 (d, J = 7.8 Hz, 1 H), 5.98-5.93 (m, 1 H), 5.64-5.60 (m, 1 H), 4.55-4.51 (m, 1 H), 4.45-4.40 (m, 1 H), 3.99-3.94 (m, 1 H), 3.06-3.01 (m, 1 H), 2.58-2.50 (m, 1 H), 2.37-2.23 (m, 2 H), 2.02-1.81 (m, 3 H), 1.71-1.68 (m, 1 H). SFC (column: Chiralpak AS-3, 3 μm, 0.46 cm id × 5 cm L; mobile phase: A (CO₂) and B (MeOH, containing 0.05% isopropylamine); gradient: B% = 10 to 40%, 3 min; flow rate: 4.0 mL/min; wavelength: 220 nm; pressure: 100 bar, Rt = 1.48 min, chiral isomer excess 100%. | 411.1 |
| 14 | WX007B | 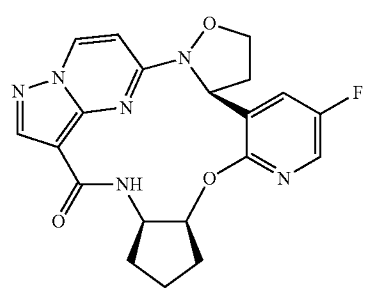 [SMILES: O=C1N[C@@H]2CCC[C@@H]2Oc2ncc(F)cc2[C@@H]2CCON2c2ccn3ncc1c3n2] | ¹H NMR (400 MHz, CDCl₃) δ: 9.67 (d, J = 6.8 Hz, 1 H), 8.50 (d, J = 7.8 Hz, 1 H), 8.44 (s, 1H), 8.00 (d, J = 3.2 Hz, 1 H), 7.58 (dd, J = 8.4, 3.2 Hz, 1 H), 6.90 (d, J = 7.8 Hz, 1 H), 6.27-6.23 (m, 1 H), 5.19-5.14 (m, 1 H), 4.51 (t, J = 8.4 Hz, 1 H), 4.35 (s, 1 H), 3.75-3.69 (m, 1 H), 3.04-2.99 (m, 1 H), 2.95-2.88 (m, 1 H), 2.72-2.51 (m, 2 H), 1.90-1.62 (m, 3 H), 1.54-1.46 (m, 1 H). SFC (column: Chiralpak AS-3, 3 μm, 0.46 cm id × 5 cm L; mobile phase: A (CO₂) and B (MeOH, containing 0.05% isopropylamine); gradient: B% = 10 to 40%, 3 min; flow rate: 4.0 mL/min; wavelength: 220 nm; pressure: 100 bar, Rt = 1.73 min, chiral isomer excess 100%. | 411.1 |

| Example | Compound | Structure | NMR and SFC | MS m/z: [M + H]+ |
|---|---|---|---|---|
| 15 | WX008A | 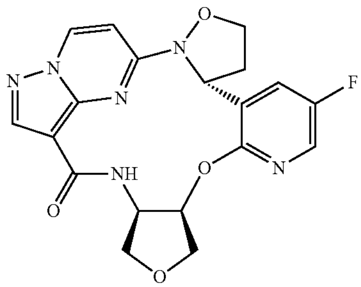 [SMILES: O=C1N[C@@H]2COC[C@@H]2Oc2ncc(F)cc2[C@H]2CCON2c2ccn3ncc1c3n2] | ¹H NMR (400 MHz, CDCl₃) δ: 9.60 (d, J = 6.4 Hz, 1H), 8.43 (d, J = 7.6 Hz, 1H), 8.37 (s, 1H), 7.94 (d, J = 2.8 Hz, 1H), 7.57 (dd, J = 8.0, 2.8 Hz, 1H), 6.79 (d, J = 7.2 Hz, 1H), 5.99-5.94 (m, 2H), 4.77-4.70 (m, 2H), 4.34-4.24 (m, 2H), 4.11-4.07 (m, 1H), 4.03-3.96 (m, 1H), 3.89 (dd, J = 7.2, 1.6 Hz, 1H), 3.09-3.02 (m, 1H), 2.60-2.50 (m, 1H). SFC (column: Chiralcel OD-3, 3 μm, 0.46 cm id × 5 cm L; mobile phase: A (CO₂) and B (MeOH, containing 0.05% isopropylamine); gradient: B% = 10 to 40%, 3 min; flow rate: 4.0 mL/min; wavelength: 220 nm; pressure: 100 bar, Rt = 1.67 min, chiral isomer excess 100%. | 413.1 |
| 16 | WX008B | 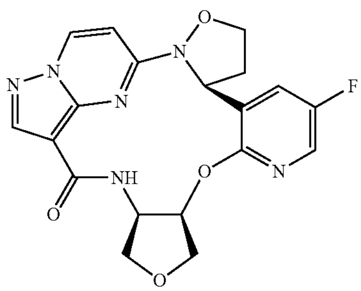 [SMILES: O=C1N[C@@H]2COC[C@@H]2Oc2ncc(F)cc2[C@@H]2CCON2c2ccn3ncc1c3n2] | ¹H NMR (400 MHz, CDCl₃) δ: 10.01 (s, 1H), 8.52 (d, J = 7.6 Hz, 1H), 8.43 (s, 1H), 7.97 (d, J = 2.8 Hz, 1H), 7.62 (dd, J = 8.0, 2.8 Hz, 1H), 6.92 (d, J = 7.6 Hz, 1H), 6.25-6.21 (m, 1H), 5.34-5.39 (m, 1H), 4.75-4.67 (m, 2H), 4.54-4.50 (m, 2H), 4.02 (dd, J = 10.0, 3.6 Hz, 1H), 3.77-3.67 (m, 2H), 2.96-2.88 (m, 1H), 2.63-2.53 (m, 1H) SFC (column: Chiralcel OD-3, 3 μm, 0.46 cm id × 5 cm L; mobile phase: A (CO₂) and B (MeOH, containing 0.05% isopropylamine); gradient: B% = 10 to 40%, 3 min; flow rate: 4.0 mL/min; wavelength: 220 nm; pressure: 100 bar, Rt = 1.94 min, chiral isomer excess 98.72%. | 413.1 |
| 17 | WX009A | 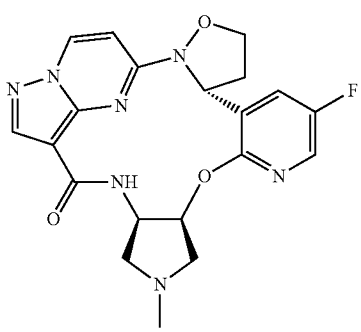 [SMILES: CN1C[C@@H]2Oc3ncc(F)cc3[C@H]3CCON3c3ccn4ncc(c4n3)C(=O)N[C@@H]2C1] | ¹H NMR (400 MHz, CD₃OD) δ: 8.68-8.66 (m, 1H), 8.24 (s, 1H), 8.03 (d, J = 2.8 Hz, 1H), 7.84-7.82 (m, 1H), 6.94-6.89 (m, 1H), 6.25-6.23 (m, 1H), 6.06-6.02 (m, 1H), 5.07-5.03 (m, 1H), 4.63-4.60 (m, 1H), 4.17-3.92 (m, 3H), 3.73-3.65 (m, 2H), 3.12-3.05 (m, 4H), 2.69-2.59 (m, 1H). SFC (column: Chiralpak AS-3, 3 μm, 0.46 cm id × 10 cm L; mobile phase: A (CO₂) and B (MeOH, containing 0.05% isopropylamine); gradient: B% = 10 to 40%, 5 min; flow rate: 4.0 mL/min; wavelength: 220 nm; pressure: 100 bar, Rt = 2.36 min, chiral isomer excess 100%. | 426.1 |

| Example | Compound | Structure | NMR and SFC | MS m/z: [M + H]+ |
|---|---|---|---|---|
| 18 | WX009B | 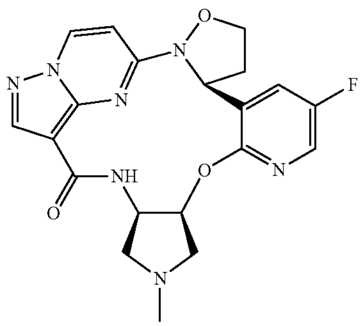 [SMILES: CN1C[C@@H]2Oc3ncc(F)cc3[C@@H]3CCON3c3ccn4ncc(c4n3)C(=O)N[C@@H]2C1] | ¹H NMR (400 MHz, CD₃OD) δ: 8.76 (d, J = 7.6 Hz, 1H), 8.32 (s, 1H), 8.08 (d, J = 3.2 Hz, 1H), 7.94-7.91 (m, 1H), 7.01 (d, J = 7.6 Hz, 1H), 6.03 (t, J = 7.6 Hz, 1H), 5.69-5.64 (m, 1H), 4.92-4.90 (m, 1H), 4.59-4.56 (m, 1H), 4.51-4.48 (m, 1H), 4.06-3.90 (m, 3H), 3.59-3.55 (m, 1H), 3.04 (s, 3H), 2.980-2.95 (m, 1H), 2.70-2.67 (m, 1H). SFC (column: Chiralpak AS-3, 3 μm, 0.46 cm id × 10 cm L; mobile phase: A (CO₂) and B (MeOH, containing 0.05% isopropylamine); gradient: B% = 10 to 40%, 5 min; flow rate: 4.0 mL/min; wavelength: 220 nm; pressure: 100 bar, Rt = 2.72 min, chiral isomer excess 100%. | 426.1 |
| 19 | WX010A | 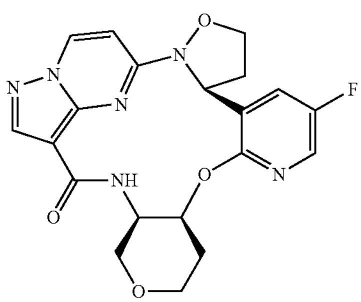 [SMILES: O=C1N[C@@H]2COCC[C@@H]2Oc2ncc(F)cc2[C@@H]2CCON2c2ccn3ncc1c3n2] | ¹H NMR (400 MHz, CDCl₃) δ: 9.64 (s, 1H), 8.52 (d, J = 7.6 Hz, 1H), 8.44 (s, 1H), 8.00 (d, J = 2.8 Hz, 1H), 7.60 (dd, J = 8.4, 2.8 Hz, 1H), 6.91 (d, J = 7.6 Hz, 1H), 6.31-6.28 (m, 1H), 5.58 (d, J = 12.0 Hz, 1H), 5.17-5.12 (m, 1H), 4.53-4.49 (m, 1H), 4.08 (s, 1H), 3.98-3 94 (m, 1H), 3.75-3.69 (m, 1H), 3.58-3.53 (m, 2H), 2.94-2.87 (m, 1H), 2.62-2.54(m, 1H), 2.52-2.42 (m, 1H), 1.81-1.77 (m, 1H). SFC (column: Chiralpak AD-3, 3 μm, 0.46 cm id × 5 cm L; mobile phase: A (CO₂) and B (EtOH, containing 0.05% isopropylamine); gradient: B% = 5 to 40%, 4 min; flow rate: 4.0 mL/min; wavelength: 220 nm; pressure: 100 bar, Rt = 1.93 min, chiral isomer excess 100.00%. | 427.1 |
| 20 | WX010B | 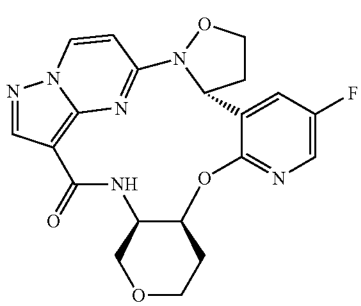 [SMILES: O=C1N[C@@H]2COCC[C@@H]2Oc2ncc(F)cc2[C@H]2CCON2c2ccn3ncc1c3n2] | ¹H NMR (400 MHz, CDCl₃) δ: 9.63 (d, J = 8.8 Hz, 1H), 8.43 (d, J = 7.6 Hz, 1H), 8.36 (s, 1H), 7.97 (d, J = 2.8 Hz 1H), 7.59-7.57 (m, 1H), 6.78 (d, J = 7.6 Hz, 1H), 5.97-5.93 (m, 1H), 5.34 (d, J = 2.8 Hz, 1H), 4.58-4.54 (m, 1H), 4.41-4.34 (m, 1H), 4.12 (dd, J = 10.8, 5.2 Hz, 1H), 4.00-3.94 (m, 1H), 3.91-3.87 (m, 1H), 3.74-3.69 (m, 1H), 3.57 (t, J = 10.8 Hz, 1H), 3.11-3.05 (m, 1H), 2.61-2.44 (m, 2H), 2.18-2.11 (m, 1H). SFC (column: Chiralpak AD-3, 3 μm, 0.46 cm id × 5 cm L; mobile phase: A (CO₂) and B (EtOH, containing 0.05% isopropylamine); gradient: B% = 5 to 40%, 4 min; flow rate: 4.0 mL/min; wavelength: 220 nm; pressure: 100 bar, Rt = 2.31 min, chiral isomer excess 96.53%. | 427.1 |

| Example | Compound | Structure | NMR and SFC | MS m/z: [M + H]+ |
|---|---|---|---|---|
| 21 | WX011A | 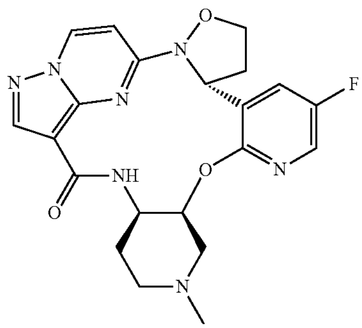 [SMILES: CN1CC[C@H]2NC(=O)c3cnn4ccc(nc34)N3OCC[C@@H]3c3cc(F)cnc3O[C@H]2C1] | ¹H NMR (400 MHz, CDCl₃) δ: 9.76 (d, J = 8.8 Hz, 1 H), 8.41 (d, J = 7.6 Hz, 1 H), 8.37 (s, 1 H), J = 7.95 (d, J = 3.2 Hz, 1 H), 7.57-7.54 (m, 1 H), 8 = 6.76 (d, J = 7.6 Hz, 1 H), 5.97-5.93 (m, 1 H), 5.11 (s, 1 H), 4.52 (t, J = 6.8 Hz, 1 H), 4 16-4.13 (m, 1 H), 3.96-3.92 (m, 1 H), 3.92-3.71 (m, 1 H), 3.19-3.14 (m, 1 H), 2.98-2.95 (m, 1 H), 2.56-2.46 (m, 1 H), 2.43-2.37 (m, 1 H), 2.35 (s, 3 H), 2.24-2.04 (m, 3 H). SFC (column: Chiralpak AS-3, 3 μm, 0.46 cm id × 5 cm L; mobile phase: A (CO₂) and B (iPrOH, containing 0.05% isopropylamine); gradient: B% = 5 to 40%, 4 min; flow rate: 4.0 mL/min; wavelength: 220 nm; pressure: 100 bar, Rt = 1.78 min, chiral isomer excess 100%. | 440.1 |
| 22 | WX011B | 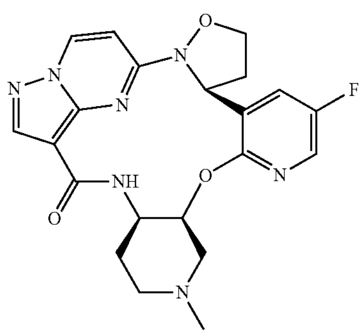 [SMILES: CN1CC[C@H]2NC(=O)c3cnn4ccc(nc34)N3OCC[C@H]3c3cc(F)cnc3O[C@H]2C1] | ¹H NMR (400 MHz, CDCl₃) δ: 9.63 (s, J = 8.8 Hz, 1 H), 8.52 (d, J = 7.6 Hz, 1 H), 8.44 (s, 1 H), J = 8.01 (d, J = 2.8 Hz, 1 H), 7.57 (dd, J = 8.4, 3.2 Hz, 1 H), J = 6.91 (d, J = 7.6 Hz, 1 H), 6.31-6.27 (m, 1 H), 5.17-5.12 (m, 1 H), 4.51 (t, J = 6.8 Hz, 1 H), 4.27-4.25 (m, 1 H), 3.75-3.68 (m, 1 H), 3.47-3.44 (m, 1 H), 2.91-2.86 (m, 1 H), 2.70-2.67 (m, 1 H), 2.63-2.53 (m, 1 H), 2.29-2.26 (m, 1 H), 2.23 (s, 3 H), 2.01-1.96 (m, 1 H), 1.93-1.80 (m, 2 H). SFC (column: Chiralpak AS-3, 3 μm, 0.46 cm id × 5 cm L; mobile phase: A (CO₂) and B (iPrOH, containing 0.05% isopropylamine); gradient: B% = 5 to 40%, 4 min; flow rate: 4.0 mL/min; wavelength: 220 nm; pressure: 100 bar, Rt = 2.07 min, chiral isomer excess 98.53%. | 440.1 |
| 23 | WX012A | 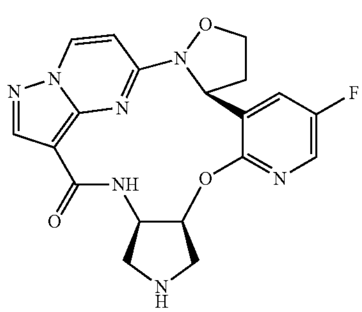 [SMILES: O=C1N[C@@H]2CNC[C@@H]2Oc2ncc(F)cc2[C@@H]2CCON2c2ccn3ncc1c3n2] | ¹HNMR (400 MHz, CDCl₃) δ: 8.66-8.64 (m, 1H), 8.22 (s, 1H), 8.04-8.03 (m, 1H), 7.84-7.81 (m, 1H), 6.90-6.88 (m, 1H), 6.05-5.96 (m, 2H), 4.95 (s, 1H), 4.60 (t, J = 7.6 Hz, 1H), 4.05-3.99 (m, 1H), 3.91-3.78 (m, 3H), 3.59-3.55 (m, 1H), 3.08 (s, 1H), 2.67-2.58 (m, 1H). SFC (column: Chiralpak AS-3, 3 μm, 0.46 cm id × 5 cm L; mobile phase: A (CO₂) and B (MeOH, containing 0.05% isopropylamine); gradient: B% = 5 to 40%, 4 min; flow rate: 4.0 mL/min; wavelength: 220 nm; pressure: 100 bar, Rt = 1.99 min, chiral isomer excess 100%. | 412.1 |

| Example | Compound | Structure | NMR and SFC | MS m/z: [M + H]+ |
|---|---|---|---|---|
| 24 | WX012B | 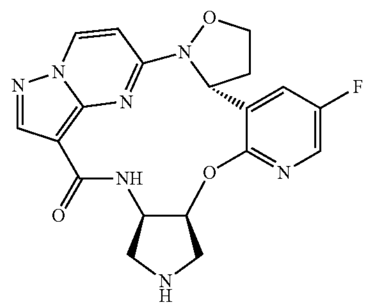 [SMILES: O=C1N[C@@H]2CNC[C@@H]2Oc2ncc(F)cc2[C@H]2CCON2c2ccn3ncc1c3n2] | ¹H NMR (400 MHz, CD₃OD) δ: 8.67-8.64 (m, 1H), 8.23-8.22 (m, 1H), 8.04 (d, J = 2.8 Hz, 1H), 7.83 (dd, J = 8.4, 2.8 Hz, 1H), 6.91-6.89 (m, 1H), 6.06-5.97 (m, 2H), 4.95-4.93 (m, 1H), 4.62-4.58 (m, 1H), 4.05-3.99 (m, 1H), 3.91-3.78 (m, 3H), 3.59-3.48 (m, 1H), 3.11-3.04 (m, 1H), 2.67-2.58 (m, 1H). SFC (column: Chiralpak AS-3, 3 μm, 0.46 cm id × 5 cm L; mobile phase: A (CO₂) and B (MeOH, containing 0.05% isopropylamine); gradient: B% = 5 to 40%, 4 min; flow rate: 4.0 mL/min; wavelength: 220 nm; pressure: 100 bar, Rt = 1.62 min, chiral isomer excess 98.59%. | 412.1 |
| 25 | WX013A | 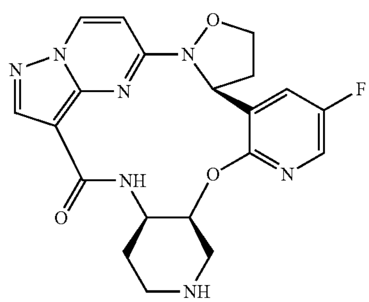 [SMILES: O=C1N[C@@H]2CCNC[C@@H]2Oc2ncc(F)cc2[C@@H]2CCON2c2ccn3ncc1c3n2] | ¹H NMR (400 MHz, CD₃OD) δ: 8.68 (d, J = 7.6 Hz, 1 H), 8.24 (s, 1 H), 8.05 (d, J = 3.2 Hz, 1 H), 7.84-7.81 (m, 1 H), 6.91 (d, J = 8 Hz, 1 H), 6.02-5.98 (m, 1 H), 5.36-5.35 (m, 1 H), 4.62-4.58 (m, 1 H), 4.44-4.39 (m, 1 H), 4.21-4.17 (m, 1 H), 4.03-3.97 (m, 1 H), 3.63-3.50 (m, 2 H), 3.28-3.23 (m, 1 H), 3.14-3.08 (m, 1 H), 2.67-2.57 (m, 1 H), 2.33-2.18 (m, 2 H). SFC (column: Chiralcel OD-3, 3 μm, 0.46 cm id × 5 cm L; mobile phase: A (CO₂) and B (MeOH, containing 0.05% isopropylamine); gradient: B% = 5 to 40%, 4 min; flow rate: 4.0 mL/min; wavelength: 220 nm; pressure: 100 bar, Rt = 2.06 min, chiral isomer excess 100%. | 426.1 |
| 26 | WX013B | 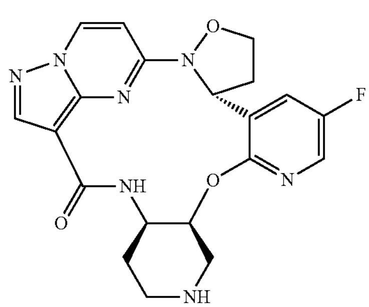 [SMILES: O=C1N[C@@H]2CCNC[C@@H]2Oc2ncc(F)cc2[C@H]2CCON2c2ccn3ncc1c3n2] | ¹H NMR (400 MHz, CD₃OD) δ: 8.72 (d, J = 7.6 Hz, 1 H), 8.29 (s, 1 H), 8.14 (d, J = 4.0 Hz, 1 H), 7.97-7.94 (m, 1 H), 6.99-6.97 (m, 1 H), 5.94-5.90 (m, 1 H), 5.24-5.20 (m, 1 H), 4.61-4.57 (m, 1 H), 4.50-4.45 (m, 1 H), 4.06-4.00 (m, 1 H), 3.92-3.83 (m, 2 H), 3.62-3.59 (m, 1 H), 3.30-3.28 (m, 1 H), 3.03-2.96 (m, 1 H), 2.61-2.55 (m, 1 H), 2.36-2.30 (m, 2 H). SFC (column: Chiralcel OD-3, 3 μm, 0.46 cm id × 5 cm L; mobile phase: A (CO₂) and B (MeOH, containing 0.05% isopropylamine); gradient: B% = 5 to 40%, 4 min; flow rate: 4.0 mL/min; wavelength: 220 nm; pressure: 100 bar, Rt = 1.78 min, chiral isomer excess 96.27%. | 426.1 |

| Example | Compound | Structure | NMR and SFC | MS m/z: [M + H]+ |
|---|---|---|---|---|
| 27 | WX014A | 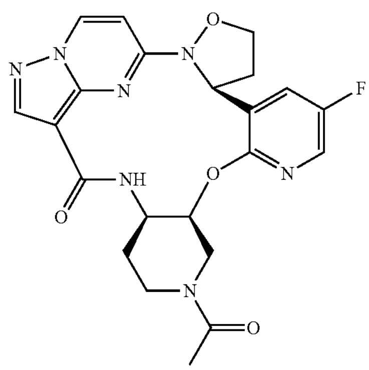 [SMILES: CC(=O)N1CC[C@H]2NC(=O)c3cnn4ccc(nc34)N3OCC[C@H]3c3cc(F)cnc3O[C@H]2C1] | ¹H NMR (400 MHz, CDCl₃) δ: 9.72 (d, J = 46.4 Hz, 1 H), 8.55-8.52 (m, 1 H), 8.43-8.41 (m, 1 H), 8.09-8.02 (m, 1 H), 7.72-7.56 (m, 1 H), 6.92 (d, J = 8.0 Hz, 1 H), 6.277-6.260 (m, 1 H), 5.32-5.28 (m, 1 H), 5.05-4.90 (m, 1 H), 4.55-4.44 (m, 2 H), 4.42-4.36 (m, 1 H), 3.77-3.65 (m, 1 H), 3.36-3.08 (m, 1 H), 2.95-2.79 (m, 1 H), 2.65-2.56 (m, 2 H), 2.18-2.30 (s, 3 H), 1.35-1.25 (m, 2 H). SFC (column: Chiralpak AD-3, 3 μm, 0.46 cm id × 5 cm L; mobile phase: A (CO₂) and B (iPrOH, containing 0.05% isopropylamine); gradient: B% = 5 to 40%, 4 min; flow rate: 4.0 mL/min; wavelength: 220 nm; pressure: 100 bar, Rt = 1.99 min, chiral isomer excess 100%. | 468.1 |
| 28 | WX014B | 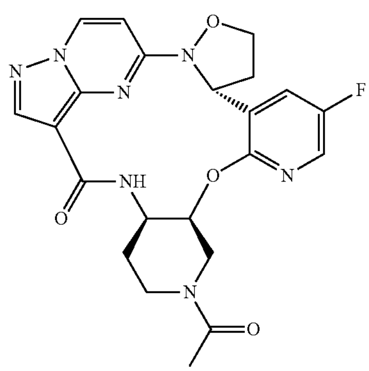 [SMILES: CC(=O)N1CC[C@H]2NC(=O)c3cnn4ccc(nc34)N3OCC[C@@H]3c3cc(F)cnc3O[C@H]2C1] | ¹H NMR (400 MHz, CDCl₃) δ: 9.78-9.71 (m, 1 H), 8.45-8.41 (m, 1 H), 8.35 (s, 1 H), 7.98-7.96 (m, 1 H), 7.64-7.59 (m, 1 H), 6.78 (d, J = 7.6 Hz, 1 H), 5.88-5.82 (m, 1 H), 5.14-5.4.99 (m, 1 H), 4.79-4.76 (m, 1 H), 4.56-4.53 (m, 1 H), 4.38-4.31 (m, 1 H), 3.96-3.90 (m, 1 H), 3.49-3.45 (m, 1 H), 3.12-2.99 (m, 1 H), 2.76-2.70 (m, 1 H), 2.55-2.47 (m, 1 H), 2.22-2.02 (m, 2 H), 1.93 (s, 3 H). SFC (column: Chiralpak AD-3, 3 μm, 0.46 cm id × 5 cm L; mobile phase: A (CO₂) and B (iPrOH, containing 0.05% isopropylamine); gradient: B% = 5 to 40%, 4 min; flow rate: 4.0 mL/min; wavelength: 220 nm; pressure: 100 bar, Rt = 2.47 min, chiral isomer excess 97.49%. | 468.1 |
| 29 | WX015A | 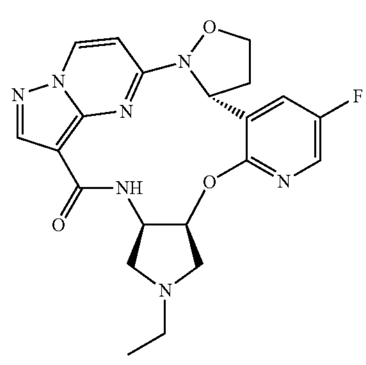 [SMILES: CCN1C[C@@H]2Oc3ncc(F)cc3[C@H]3CCON3c3ccn4ncc(c4n3)C(=O)N[C@@H]2C1] | ¹H NMR (400 MHz, CD₃OD) δ: 8.71-8.66 (m, 1H), 8.26-8.25 (m, 1H), 8.04-8.03 (m, 1H), 7.84-7.82 (m, 1H), 6.95-6.90 (m, 1H), 6.21-6.19 (m, 1H), 6.07-6.03 (m, 1H), 5.03 (s, 1H), 4.64-4.60 (m, 1H), 4.17-3.90 (m, 3H), 3.73-3.66 (m, 2H), 3.47-3.36 (m, 2H), 3.13-2.98 (m, 1H), 2.69-2.59 (m, 1H), 1.41 (t, J = 7.2 Hz, 3H). SFC (column: Chiralpak AS-3, 3 μm, 0.46 cm id × 10 cm L; mobile phase: A (CO₂) and B (MeOH, containing 0.05% isopropylamine); gradient: B% = 10 to 40%, 5 min; flow rate: 4.0 mL/min; wavelength: 220 nm; pressure: 100 bar, Rt = 2.31 min, chiral isomer excess 100%. | 440.1 |

| Example | Compound | Structure | NMR and SFC | MS m/z: [M + H]+ |
|---|---|---|---|---|
| 30 | WX015B | 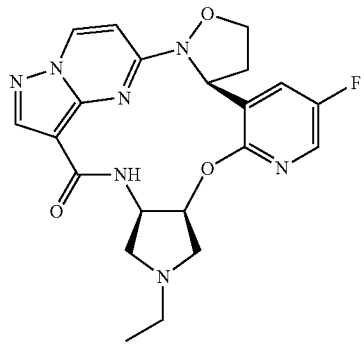 [SMILES: CCN1C[C@@H]2Oc3ncc(F)cc3[C@@H]3CCON3c3ccn4ncc(c4n3)C(=O)N[C@@H]2C1] | ¹H NMR (400 MHz, CD₃OD) δ: 8.79-8.77 (m, 1H), 8.34 (s, 1H), 8.09 (d, J = 2.8 Hz, 1H), 7.95-7.92 (m, 1H), 7.03 (d, J = 7.6 Hz, 1H), 6.10-6.06 (m, 1H), 5.69-5.64 (m, 1H), 4.81-4.80 (m, 1H), 4.61-4.55 (m, 2H), 4.13-1.05 (m, 1H), 3.92-3.80 (m, 2H), 3.55-3.50 (m, 1H), 3.42-3.35 (m, 2H), 2.99-2.92 (m, 1H), 2.73-2.63 (m, 1H), 1.35 (t, J = 7.2 Hz, 3H). SFC (column: Chiralpak AS-3, 3 μm, 0.46 cm id × 10 cm L; mobile phase: A (CO₂) and B (MeOH, containing 0.05% isopropylamine); gradient: B% = 10 to 40%, 5 min; flow rate: 4.0 mL/min; wavelength: 220 nm; pressure: 100 bar, Rt = 2.72 min, chiral isomer excess 100%. | 440.1 |
| 31 | WX016A | 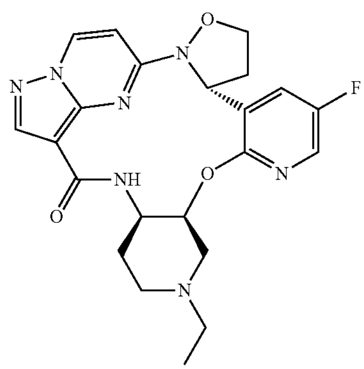 [SMILES: CCN1CC[C@H]2NC(=O)c3cnn4ccc(nc34)N3OCC[C@@H]3c3cc(F)cnc3O[C@H]2C1] | ¹H NMR (400 MHz, CDCl₃) δ: 9.76 (d, J = 8.8 Hz, 1 H), 8.41 (d, J = 7.6 Hz, 1 H), 8.37 (s, 1 H), J = 7.95 (d, J = 3.2 Hz, 1 H), 7.57-7.51 (m, 1 H), J = 6.76 (d, J = 7.6 Hz, 1 H), 5.98-5.94 (m, 1 H), 5.15 (s, 1 H), 4.52 (t, J = 6.8 Hz, 1 H), 4.25-4.14 (m, 1 H), 3.96-3.90 (m, 1 H), 3.87-3.83 (m, 1 H), 3.25-3.14 (m, 1 H), 3.07-2.99 (m, 1 H), 2.68-2.41 (m, 3 H), 2.38-2.31 (m, 1 H), 2.28-2.07 (s, 3 H), 1.16-1.08 (m, 3 H). SFC (column: Chiralpak AS-3, 3 μm, 0.46 cm id × 5 cm L; mobile phase: A (CO₂) and B (iPrOH, containing 0.05% isopropylamine); gradient: B% = 5 to 40%, 4 min; flow rate: 4.0 mL/min; wavelength: 220 nm; pressure: 100 bar, Rt = 1.77 min, chiral isomer excess 100%. | 454.1 |
| 32 | WX016B | 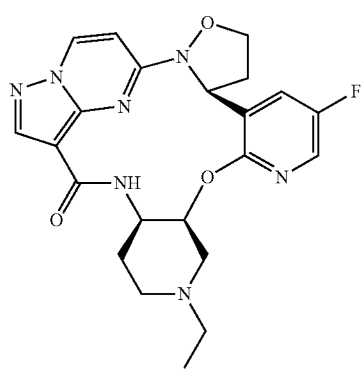 [SMILES: CCN1CC[C@H]2NC(=O)c3cnn4ccc(nc34)N3OCC[C@H]3c3cc(F)cnc3O[C@H]2C1] | ¹H NMR (400 MHz, CDCl₃) δ: 9.63 (s, 1 H), 8.52 (d, J = 7.6 Hz, 1 H), 8.44 (s, 1 H), δ = 8.01 (d, J = 3.2 Hz, 1 H), 7.57 (dd, J = 8.4, 3.2 Hz, 1 H), δ = 6.92 (d, J = 7.6 Hz, 1 H), 6.32-6.28 (m, 1 H), 5.18-5.14 (m, 1 H), 4.52 (t, J = 6.8 Hz, 1 H), 4.29-4.27 (m, 1 H), 3.75-3.69 (m, 1 H), 3.57-3.44 (m, 2 H), 2.91-2.78 (m, 2 H), 2.63-2.53 (m, 1 H), 2.41-2.35 (m, 2 H), 2.24-2.18 (m, 1 H), 2.00 (t, J = 10.4 Hz, 1 H), 1.92-1.78 (m, 1H), 1.02 (t, J = 7.2 Hz, 3 H). SFC (column: Chiralpak AS-3, 3 μm, 0.46 cm id × 5 cm L; mobile phase: A (CO₂) and B (iPrOH, containing 0.05% isopropylamine); gradient: B% = 5 to 40%, 4 min; flow rate: 4.0 mL/min; wavelength: 220 nm; pressure: 100 bar, Rt = 2.05 min, chiral isomer excess 97.62%. | 454.1 |

| Example | Compound | Structure | NMR and SFC | MS m/z: [M + H]+ |
|---|---|---|---|---|
| 33 | WX018 | 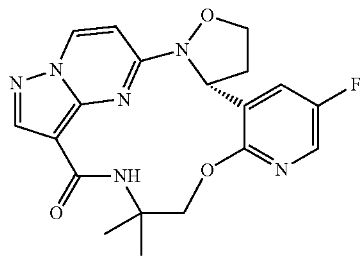 [SMILES: CC1(C)COc2ncc(F)cc2[C@H]2CCON2c2ccn3ncc(c3n2)C(=O)N1] | $^1$H NMR (400 MHz, CDCl$_3$) δ: 8.48 (d, J = 7.6 Hz, 1 H), 8.35 (s, 1 H), 7.53-7.50 (m, 1 H), 7.16 (s, 1 H), 7.02 (d, J = 7.6 Hz, 1 H), 5.95-5.92 (m, 1 H), 4.21-4.16 (m, 1 H), 4.07 (s, 2 H), 3.96-3.90 (m, 1 H), 2.81-2.77 (m, 1 H), 2.53-2.49 (m, 1 H), 1.49 (s, 3 H), 1.37 (s, 3 H). SFC (column: Chiralpak AS-3, 3 μm, 0.46 cm id × 10 cm L; mobile phase: A (CO$_2$) and B (MeOH, containing 0.05% isopropylamine); gradient: B% = 10 to 40%, 5 min; flow rate: 4 mL/min; wavelength: 220 nm; pressure: 100 bar, Rt = 1.83 min, chiral isomer excess 98.2%. | 399.2 |

By methods similar to the synthesis methods of steps 1 to 11 in Example 3, examples in the following table were synthesized.

| Example | Compound | Structure | NMR and SFC | MS m/z: [M + H]+ |
|---|---|---|---|---|
| 34 | WX017A | 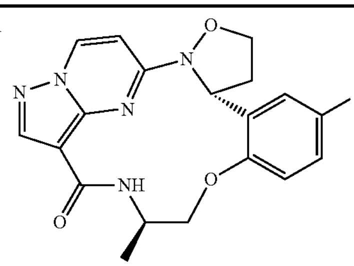 | $^1$H NMR (400 MHz, DMSO-d$_6$) δ: 9.89 (d, J = 8.0 Hz, 1H), 8.95 (d, J = 7.2 Hz, 1H), 8.26 (br s, 1H), 7.33-6.99 (m, 3H), 6.85 (d, J = 7.2 Hz, 1H), 6.20-6.10 (m, 1H), 4.60-4.50 (m, 1H), 4.47-4.40 (m, 1H), 4.29-4.20 (m 1H), 4.09-3.92 (m, 2H), 3.91-3.82 (m, 1H), 3.03-2.94 (m, 1H), 1.38 (d, J = 6.0 Hz, 3H). | 384.1 |
| 35 | WX017B | 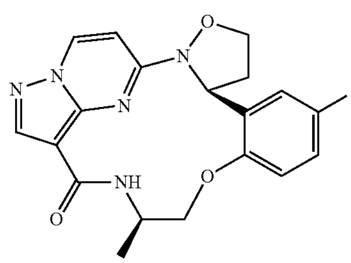 | $^1$H NMR (400 MHz, DMSO-d$_6$) δ: 9.33 (s, 1H), 8.97 (d, J = 7.6 Hz, 1H), 8.26 (s, 1H), 7.27-7.23 (m, 1H), 7.18-7.15 (m, 2H), 6.89 (d, J = 7.6 Hz, 1H), 6.15-6.08 (m, 1H), 4 55-4.39 (m, 2H), 4.10-4.03 (m, 1H), 3.89-3.70 (m, 2H), 2.96-2.87 (m, 1H), 2.44-2.36 (m, 1H), 1.48 (d, J = 6.3 Hz, 3H). | 384.1 |

Experimental Example 1: Inhibitory Activities of the Compounds on TrkA, TrkC, ALK, Ros1 and Other Kinases The inhibitory activities of the compounds on TrkA, TrkC, ALK, Ros1 and other kinases were determined by Reaction Biology Corp. To reaction buffer (20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO) were sequentially added a certain concentration of substrate, coenzyme factor, kinase and test compound (10 concentrations, 3-fold serial dilutions, DMSO at a final concentration of 2%), and the mixture was mixed evenly. The mixture was incubated at room temperature for 20 minutes. To the reaction mixture was added a certain concentration of $^{33}$P-ATP to initiate the reaction, and then the mixture was incubated at room temperature for 120 minutes. The radioactivities of the reactants were determined by the method of filter binding. The final kinase activity was expressed as the ratio of the remaining kinase activity in the test sample to the kinase activity in the DMSO control group. The dose-effect curve was fitted by GraphPad software and the IC$_{50}$ was calculated. The results are shown in Table 1:

TABLE 1

| Compound | TrkA | TrkA-G595R | TrkA-G667C | TrkC | ALK | Ros1 | Ros-G2032R |
|---|---|---|---|---|---|---|---|
| WX001 hydrochloride | 177.00 | / | / | / | / | / | / |
| WX002 | 4.37 | / | / | / | / | / | / |
| WX002A | 2.07 | 3.60 | 7.00 | 0.14 | 13.00 | 0.14 | 0.4 |
| WX002B | >1000 | / | / | / | / | / | / |
| WX003A | 2.66 | 3.59 | 3.04 | 0.06 | 28.10 | 0.15 | / |
| WX003B | >1000 | / | / | / | / | / | / |
| WX004A | 14.30 | 38.50 | 42.00 | 0.41 | 109.00 | 0.94 | / |
| WX004B | >1000 | / | / | 105.00 | / | / | / |
| WX005A | >1000 | / | / | 189.00 | >1000 | 531.00 | / |
| WX005B | 13.10 | 10.70 | 26.40 | 0.09 | 19.40 | 0.35 | 2.65 |
| WX006A | 9.84 | 4.74 | 37.50 | 0.16 | 79.20 | 0.59 | / |
| WX006B | >1000 | >1000 | / | / | / | / | / |
| WX007A | 2.80 | 5.18 | 2.85 | 0.05 | 11.60 | 0.13 | 0.73 |
| WX007B | 585.00 | >1000 | / | / | / | / | / |
| WX008A | 1.61 | 2.31 | 6.49 | 0.05 | 10.40 | 0.16 | 0.52 |
| WX008B | >1000 | >1000 | / | / | / | / | / |
| WX009A | 85.10 | / | / | / | / | / | / |
| WX009B | >1000 | / | / | / | / | / | / |
| WX010A | >1000 | / | / | / | / | / | / |
| WX010B | 3.10 | / | / | / | / | / | 0.61 |
| WX011A | 33.60 | / | / | / | / | / | / |
| WX011B | 270.00 | / | / | / | / | / | / |
| WX012A | >1000 | / | / | / | / | / | / |
| WX012B | 143.00 | / | / | / | / | / | / |
| WX013A | >1000 | / | / | / | / | / | / |
| WX013B | 57.20 | / | / | / | / | / | / |
| WX014A | 1230.00 | / | / | / | / | / | / |
| WX014B | 12.80 | / | / | / | / | / | / |
| WX015A | 182.00 | / | / | / | / | / | / |
| WX015B | >1000 | / | / | / | / | / | / |
| WX016A | 33.00 | / | / | / | / | / | / |
| WX016B | 220.00 | / | / | / | / | / | / |
| WX017A | 13.40 | 37.10 | 26.30 | 0.30 | 119.00 | 0.82 | / |
| WX017B | >1000 | / | / | / | / | / | / |
| WX018 | >1000 | / | / | / | / | / | / |
| LOXO-101 | 19.70 | >1000 | 512.00 | 1.12 | >1000 | 95.50 | / |
| LOXO-195 | 6.67 | 6.19 | 110.00 | 0.50 | 274.00 | 1.15 | 2.88 |

The half maximal inhibitory concentration IC$_{50}$ on the kinases (nM)

"/": Not detected.

The results show that the compounds of the present disclosure exhibit strong kinase inhibitory activities against a variety of kinases and their mutants, and exhibit strong inhibitory effects against gatekeeper mutation, solvent front mutation and DFG mutations of a variety of kinases.

Experimental Example 2: Inhibitory Activities of the Compounds on Cell Proliferation Adenosine Tri-Phosphate (ATP) is an energy carrier shared by various life activities in nature, and is the smallest unit of energy storage and transfer. The CellTiter-Glo™ cell viability detection kit uses luciferase as the detection substance, and luciferase requires the participation of ATP during the process of luminescence. CellTiter-Glo™ reagent is added to cell culture medium, and the luminescent intensity is measured. The luminescent signal is directly proportional to the amount of ATP in the system, and ATP is positively related to the number of living cells. Therefore, by using the CellTiter-Glo kit to detect ATP content, cell proliferation can be detected. In this assay, the cell line is Ba/F3 LMNA-NTRK1-WT stably transfected cell line, with 5000 cells/well.

IC$_{50}$ Determination Process:

1. Cell Culture and Inoculation a) the cells in the logarithmic growth phase were harvested, and counted with a platelet counter. Trypan blue exclusion method was used to detect cell viability to ensure the cell viability was no less than 90%.

b) the cell concentration was adjusted; 90 μL of cell suspension was added respectively into a 96-well plate.

c) the cells in the 96-well plates was cultured under conditions of 37° C., 5% CO$_2$ and 95% humidity overnight.

2. Drug Dilution and Administration a) 10-fold drug solutions were prepared, the highest concentration was 10 μM, 9 concentrations, 3-fold diluted (refer to Appendix I). 10 μL of each drug solution was added to each well of the 96-well plate seeded with the cells in triplicate.

b) the cells in the 96-well plate added with the drug were cultured under conditions of 37° C., 5% CO$_2$ and 95% humidity for 72 hours, and then CTG (cell proliferation) was performed.

3. Reading at End Point a) CellTiter-Glo™ reagent was thawed, and the cell plate was equilibrated at room temperature for 30 minutes.

b) CellTiter-Glo™ reagent of a same volume was added to each well;

c) the cell plate was shaken on an orbital shaker for 5 minutes to lyse the cells.

d) the cell plate was placed at room temperature for 20 minutes to stabilize the luminescent signal.

e) the luminescent intensity was read.

4. Data Processing

GraphPad Prism 5.0 software was used to analyze the data, nonlinear S-curve regression was used to fit the data to obtain dose-effect curve, and $IC_{50}$ value was calculated therefrom. The data are shown in Table 2.

TABLE 2

The half maximal inhibitory concentration $IC_{50}$ against cells (nM)

| Compound | Ba/F3 LMNA-NTRK1-WT | Ba/F3 LMNA-NTRK1-F589L | Ba/F3 LMNA-NTRK1-G595R | BaF3 ETV6-NTRK3-G623R | Ba/F3 SLC34A2-ROS1-WT | Ba/F3 SLC34A2-ROS1-G2032R |
|---|---|---|---|---|---|---|
| WX002A | 1.26 | 0.78 | 6.20 | 3.40 | 2.53 | 16.08 |
| WX003A | 4.08 | / | 27.90 | 0.90 | / | / |
| WX004A | 7.69 | / | 14.50 | 2.10 | / | / |
| WX005B | 5.73 | / | 9.10 | 5.60 | 17.92 | 258.60 |
| WX006A | 23.50 | / | 19.40 | 5.40 | / | / |
| WX007A | 5.80 | / | 12.40 | 69.13 | 10.10 | 165.17 |
| WX008A | 1.60 | 1.59 | 3.92 | 3.49 | 5.45 | 38.47 |
| WX009A | 76.80 | / | / | / | / | / |
| WX010B | 5.80 | 4.26 | 20.94 | 19.48 | 10.45 | 58.05 |
| WX011A | 39.71 | / | / | / | / | / |
| WX012B | 258.75 | / | / | / | / | / |
| WX013B | 215.55 | / | / | / | / | / |
| WX014B | 80.41 | / | / | / | / | / |
| WX015A | 65.13 | / | / | / | / | / |
| WX016A | 65.80 | / | / | / | / | / |

"/": Not detected.

The results show that the compounds of the present disclosure exhibit strong inhibitory activities on cell proliferation of Ba/F3 LMNA-NTRK1-WT stably transfected cell line. The compounds also exhibit strong inhibitory activities on cell proliferation of Ba/F3 LMNA-NTRK1-F589L, Ba/F3 LMNA-NTRK1-G595R, BaF3 ETV6-NTRK3-G623R, Ba/F3 SLC34A2-ROS1-WT and Ba/F3 SLC34A2-ROS1-G2032R stably transfected cell lines.

Experimental Example 3: In Vivo Cassette Pharmacokinetic Test of the Compounds in Mice Experimental object: male CD-1 mice aged 7-9 weeks were used as the experimental animals, the LC/MS/MS method was used to determine the drug concentrations of WX002A, TPX0005, Entrectinib (RXDX-101) and Larotrectinib (LOXO-101) in plasma and specific tissues at different time points after single intravenous (IV) and intragastric (PO) cassette administration of WX002A, TPX0005, Entrectinib (RXDX-101) and Larotrectinib (LOXO-101), in vivo pharmacokinetic behaviors of the compounds of the present disclosure in mice were studied, and pharmacokinetic characteristics thereof were evaluated.

Drug preparation: WX002A, TPX0005, Entrectinib (RXDX-101) and Larotrectinib (LOXO-101) were prepared into clear solutions with 5% DMSO+10% solutol+85% water as solvent for administration in IV (intravenous) group and PO (intragastric) group. The dose of the compounds: IV dose of 1 mg/kg, administration volume of 2 mL/kg; PO dose of 3 mg/kg, and administration volume of 3 mL/kg. The results of pharmacokinetic parameters are shown in Table 3:

TABLE 3

Results of in vivo cassette pharmacokinetic test in mice

| | Compound | LOXO-101 | RXDX-101 | TPX-0005 | WX002A |
|---|---|---|---|---|---|
| IV @ 1 mpk | Initial concentration $C_0$ (nM) | 2379 | 2808 | 2253 | 3708 |
| | Half life $T_{1/2}$ (h) | 1.21 | 1.94 | 3.69 | 0.88 |
| | Apparent volume of distribution Vd (L/kg) | 1.57 | 1.24 | 2.63 | 0.57 |
| | Apparent clearance Cl (mL/Kg/min) | 22.7 | 7.9 | 16.5 | 6.3 |
| | Area under curve $AUC_{0-inf}$ (nM · hr) | 1717 | 3767 | 2857 | 6689 |
| PO @ 3 mpk | Peak concentration $C_{max}$ (nM) | 1353 | 586 | 1540 | 4740 |
| | Time of Peak concentration $T_{max}$ (h) | 0.5 | 0.75 | 0.75 | 0.25 |
| | Area under curve $AUC_{0-inf}$ (nM · hr) | 2720 | 3256 | 5494 | 19769 |
| | Bioavailability F % | 51% | 23% | 64% | 76% |
| | drug concentration in brain at 0.5 h Brain@0.5 h (nmol/kg) | 40 | ND | 50 | 663 |
| | drug concentration in brain at 2 h Brain@2 h (nmol/kg) | 20 | 30 | 41 | 343 |

TABLE 3-continued

Results of in vivo cassette pharmacokinetic test in mice

| Compound | LOXO-101 | RXDX-101 | TPX-0005 | WX002A |
|---|---|---|---|---|
| drug concentration in cerebrospinal fluid at 0.5 hour CSF@0.5 h (nmol/kg) | 15 | ND | 8 | 63 |
| drug concentration in cerebrospinal fluid at 2 hour CSF@2 h (nmol/kg) | 3 | ND | ND | 21 |

"ND": Not detected.

The results show that: WX002A has better pharmacokinetic properties in mice. Compared with TPX0005, Entrectinib (RXDX-101) and Larotrectinib (LOXO-101), the total exposure of WX002A after oral administration, and the exposure of WX002A in brain and cerebrospinal fluid CSF at 0.5 h and 2 h respectively after administration were significantly higher than the corresponding exposure of TPX0005, Entrectinib (RXDX-101) and Larotrectinib (LOXO-101) at the same dosage.

Experimental Example 4: The In Vivo Pharmacokinetic Test of the Compounds in Mice Experimental object: male CD-1 mice aged 7-9 weeks were used as the experimental animals, the LC/MS/MS method was used to determine the drug concentrations in plasma at different time points after single intravenous (IV) and intragastric (PO) administration of the compounds, in vivo pharmacokinetic behaviors of the compounds of the present disclosure in mice were studied, and pharmacokinetic characteristics thereof were evaluated.

Drug preparation: The compounds were prepared into clear solutions with 5% DMSO+10% solutol+85% water as solvent for administration in IV (intravenous) group and PO (intragastric). The dose of the compounds: IV dose of 3 mg/kg, and PO dose of 10 mL/kg.

The results of pharmacokinetic parameters are shown in Table 4:

TABLE 4

Results of pharmacokinetic test in mice

| Compound | | LOXO-101 | LOXO-195 | WX002A | WX003A | WX004A | WX005B |
|---|---|---|---|---|---|---|---|
| Half life $T_{1/2}$ (h) | IV | 0.39 | 1.19 | 0.75 | 0.70 | 0.74 | 0.50 |
| Apparent volume of distribution Vd (L/kg) | | 0.97 | 0.50 | 0.49 | 0.81 | 0.75 | 0.44 |
| Apparent clearance Cl (mL/Kg/min) | | 37.4 | 11.8 | 7.2 | 10.8 | 10.4 | 12.4 |
| Area under the curve $AUC_{0-last}$ (nM · hr) | | 3122 | 11146 | 17502 | 12216 | 12464 | 10544 |
| Peak concentration $C_{max}$ (nM) | PO | 1548 | 12700 | 9145 | 7360 | 10520 | 17250 |
| Time of peak concentration $T_{max}$ (h) | | 0.38 | 0.38 | 0.50 | 0.38 | 0.5 | 0.38 |
| Area under the curve $AUC_{0-last}$ (nM · hr) | | 2890 | 27344 | 29787 | 27967 | 29648 | 29367 |
| Bioavailability F % | | 28% | 74% | 51% | 69% | 72% | 85% |

| Compound | | WX006A | WX007A | WX008A | WX010B | WX017A |
|---|---|---|---|---|---|---|
| Half life $T_{1/2}$ (h) | IV | 0.56 | 0.88 | 1.14 | 0.92 | 0.71 |
| Apparent volume of distribution Vd (L/kg) | | 1.01 | 0.47 | 0.62 | 0.68 | 0.74 |
| Apparent clearance Cl (mL/Kg/min) | | 19.9 | 5.50 | 6.7 | 8.4 | 17.8 |
| Area under the curve $AUC_{0-last}$ (nM · hr) | | 6104 | 22095 | 18220 | 14031 | 7337 |
| Peak concentration $C_{max}$ (nM) | PO | 8775 | 22550 | 12200 | 13000 | 10790 |
| Time of peak concentration $T_{max}$ (h) | | 0.25 | 0.38 | 0.25 | 0.5 | 0.63 |
| Area under the curve $AUC_{0-last}$ (nM · hr) | | 14448 | 54927 | 39553 | 49196 | 26657 |

TABLE 4-continued

Results of pharmacokinetic test in mice

| Bioavailability F % | 72% | 76% | 65% | 107% | 111% |

The results show that the total exposure, peak concentration, and bioavailability of multiple compounds of the present disclosure after oral administration are significantly better than Larotrectinib (LOXO-101) and LOXO-195 at the same dosage, indicating excellent pharmacokinetics characteristics.

Experimental Example 5: Test of In Vivo Efficacy of the Compounds in Mice

Experimental object: evaluation of the in vivo efficacy of test drugs such as WX002A on subcutaneous xenograft tumor of human colon cancer cell line KM12 cell in BALB/c mouse model.

Drug preparation: The compounds were all prepared into clear solutions with 5% DMSO+10% solutol+85% water as solvent for administration in the PO (intragastric) group.

Tumor measurement: the tumor diameters were measured with a vernier caliper twice a week. The calculation formula of tumor volume is: $V=0.5 \times a \times b^2$, wherein a and b represent the long diameter and short diameter of the tumor, respectively. The anti-tumor efficacy of the compounds is evaluated by TGI (%). TGI (%) reflects tumor growth inhibition rate. TGI (%)=[(1−(average tumor volume at the end of the administration in a treatment group−average tumor volume at the beginning of the administration in the treatment group))/(average tumor volume at the end of the treatment in the solvent control group−average tumor volume at the beginning of the treatment in the solvent control group)]× 100%. The results are shown in FIG. 1.

Statistical analysis: The statistical analysis was based on the relative tumor volume and tumor weight at the end of the experiment using SPSS software. One-way ANOVA was used to analyze the comparison between multiple groups. If the variance was uniform (the F values were not significantly different), the Tukey's method was used for analysis, and if the variance was not uniform (the F values were significantly different), the Games-Howell method was used for analysis. P<0.05 was considered to indicate significant difference.

Experimental results: In the nude mouse xenograft model of human colon cancer KM12, the test compound WX002A had a significant anti-tumor effect at a dose as low as 3 mg/kg, and the anti-tumor effect had dose-effect-dependent trend (p<0.05 between the high-dose group and the low-dose group). The anti-tumor effect of WX002A at a dose of 3 mg/kg (T/C=33.18%, TGI=71.23%) and the anti-tumor effect of the compound LOXO-101 in the high-dose group (60 mg/kg) (T/C=34.20%, TGI=69.73%) were equivalent (P>0.05). The anti-tumor effect of WX002A at a dose of 15 mg/kg (T/C=15.63%, TGI=88.61%) was better than that of LOXO-101 high-dose group (60 mg/kg) (T/C=34.20%, TGI=69.73%), and was equivalent to the anti-tumor effect of TPX-0005 in the high-dose group (3 mg/kg) (T/C=16.80%, TGI=87.46%) (P>0.05).

Experimental Example 6: Test of the Efficacy of the Compounds in Mice

Experimental object: evaluation of the in vivo efficacy of test drugs such as WX002A on subcutaneous xenograft tumor of human lung cancer LU-01-0414 in BALB/c mouse model.

Drug preparation: The compounds were all prepared into clear solutions with 5% DMSO+10% solutol+85% water as solvent for administration in the PO (intragastric) group.

Figure 2:
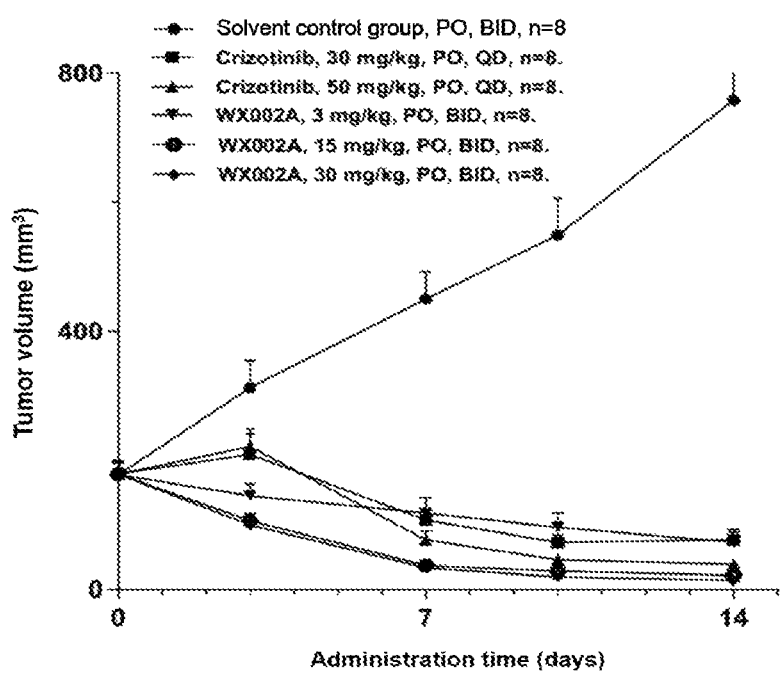
FIG. 2: subcutaneous xenograft tumor model of human lung cancer LU-01-0414.

Tumor measurement: the tumor diameters were measured with a vernier caliper twice a week. The calculation formula of tumor volume is: $V=0.5 \times a \times b^2$, wherein a and b represent the long diameter and short diameter of the tumor, respectively. The anti-tumor efficacy of the compounds was evaluated by TGI (%). TGI (%) reflects tumor growth inhibition rate. TGI (%)=[(1−(average tumor volume at the end of the administration in a treatment group−average tumor volume at the beginning of the administration in the treatment group))/(average tumor volume at the end of the treatment in the solvent control group−average tumor volume at the beginning of the treatment in the solvent control group)]× 100%. The results are shown in FIG. 2.

Statistical analysis: the statistical analysis was based on the relative tumor volume and tumor weight at the end of the experiment using SPSS software. One-way ANOVA was used to analyze the comparison between multiple groups. If the variance was uniform (the F values were not significantly different), the Tukey's method was used for analysis, and if the variance was not uniform (the F values were significantly different), the Games-Howell method was used for analysis. P<0.05 was considered to indicate significant difference.

Experimental results: at the 14$^{th}$ day after administration in subcutaneous xenograft tumor of human lung cancer LU-01-0414, WX002A exhibits a significant inhibitory effect on tumor growth when administered at a dosage of 3, 15 and 30 mg/kg BID, with T/C of 9.57%, 3.07%, and 1.87% respectively, and TGI of 118.02%, 126.88%, and 128.36% respectively, and all WX002A groups show P<0.0001 compared with the solvent control group. Crizotinib administered at a dosage of 30 and 50 mg/kg QD exhibits T/C of 10.32% and 4.89% respectively, and TGI of 117.67% and 124.09% respectively, and all crizotinib groups show P<0.0001 compared with the solvent control group, indicating significant anti-tumor effect. The above results suggest that in the xenograft tumor model of human lung cancer LU-01-0414 in nude mice, WX002A has a significant anti-tumor effect at a dose as low as 3 mg/kg, and the anti-tumor effects of WX002A at a dose of 3 mg/kg and crizotinib at a dose of 30 mg/kg were equivalent (p>0.05).

What is claimed is:

1. A compound represented by formula (II), an isomer thereof or a pharmaceutically acceptable salt thereof,

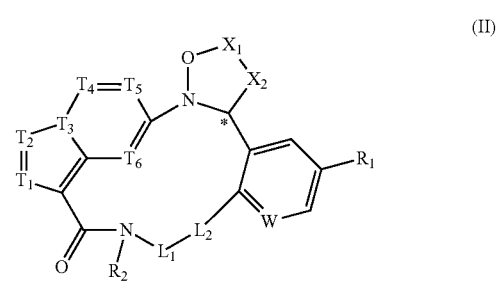
(II)

wherein, $T_1$, $T_2$, $T_3$, $T_4$, $T_5$, and $T_6$ are each independently selected from the group consisting of $CR_3$ and N;

W is selected from the group consisting of $CR_4$ and N;

$X_1$ and $X_2$ are each independently $CR_5R_6$;

$R_1$ is selected from the group consisting of H, F, Cl, Br, I, OH, $NH_2$, CN and $C_{1-6}$ alkyl, wherein the $C_{1-6}$ alkyl is optionally substituted by 1, 2 or 3 $R_a$;

$R_2$ is selected from the group consisting of H and $C_{1-6}$ alkyl, wherein the $C_{1-6}$ alkyl is optionally substituted by 1, 2 or 3 $R_b$;

$R_3$ and $R_4$ are each independently selected from the group consisting of H, F, Cl, Br, I, OH and $NH_2$;

$R_5$ and $R_6$ are each independently selected from the group consisting of H, F, Cl, Br, I, OH, $NH_2$ and $C_{1-6}$ alkyl;

$L_1$ is selected from the group consisting of —$C_{1-3}$ alkyl—, —$C_{3-6}$ cycloalkyl— and -4-to 6-membered heterocycloalkyl—, wherein the —$C_{1-3}$ alkyl—, —$C_{3-6}$ cycloalkyl— and -4- to 6-membered heterocycloalkyl— are optionally substituted by 1, 2 or 3 $R_c$;

$L_2$ is selected from the group consisting of —$C_{1-3}$ alkyl—, —$C_{1-3}$ alkyl—O—, —N(Rd)—, —$C_{1-3}$ alkyl—N(Rd)— and —O—;

$R_a$ is independently selected from the group consisting of H, F, Cl, Br, I, OH and $NH_2$;

$R_b$ is selected from the group consisting of H, F, Cl, Br, I, OH and $NH_2$;

$R_c$ is selected from the group consisting of H, F, Cl, Br, I, OH, $NH_2$, CN, $C_{1-3}$ alkyl and $C_{1-3}$ alkyl—C=O—, wherein the $C_{1-3}$ alkyl and $C_{1-3}$ alkyl—C=O— are optionally substituted by 1, 2 or 3 R;

$R_d$ is selected from the group consisting of H and $C_{1-3}$ alkyl;

R is independently selected from the group consisting of F, Cl, Br, I, OH and $NH_2$;

the carbon atom marked with "*" is a chiral carbon atom present in a single enantiomer form of (R) or (S) or in a form enriched in one enantiomer;

the 4- to 6-membered heterocycloalkyl independently comprises 1, 2, 3 or 4 heteroatoms or heteroatomic groups independently selected from the group consisting of —NH—, —O—, —S—and N.

2. The compound, isomer thereof or pharmaceutically acceptable salt thereof as defined in claim 1, wherein $R_1$ is independently selected from the group consisting of H, F, Cl, Br, I, OH, $NH_2$, CN and $CH_3$.

3. The compound, isomer thereof or pharmaceutically acceptable salt thereof as defined in claim 1, wherein $R_2$ is selected from the group consisting of H and $CH_3$.

4. The compound, isomer thereof or pharmaceutically acceptable salt thereof as defined in claim 1, wherein $R_5$ and $R_6$ are each independently selected from the group consisting of H, F, Cl, Br, I, OH, $NH_2$ and $CH_3$.

5. The compound, isomer thereof or pharmaceutically acceptable salt thereof as defined in claim 1, wherein $R_c$ is selected from the group consisting of H, F, Cl, Br, I, OH, $NH_2$, CN, $CH_3$, $CH_3$ $CH_2$ and $CH_3$ C(=O), wherein the $CH_3$, $CH_3$ $CH_2$ and $CH_3$ C(=O) are optionally substituted by 1, 2 or 3 R.

6. The compound, isomer thereof or pharmaceutically acceptable salt thereof as defined in claim 5, wherein $R_c$ is selected from the group consisting of H, F, Cl, Br, I, OH, $NH_2$, CN, $CH_3$, $CH_2F$, $CHF_2$, $CF_3$, $CH_3$ $CH_2$ and $CH_3$ C(=O).

7. The compound, isomer thereof or pharmaceutically acceptable salt thereof as defined in claim 1, wherein $L_1$ is selected from the group consisting of —$CH_2$—, —$CH_2CH_2$—, —cyclopropyl—, —cyclobutyl—, —cyclopentyl—, —oxetanyl—, —tetrahydrofuranyl—, —tetrahydropyranyl—, —pyrrolidinyl— and —piperidinyl—, wherein the —$CH_2$—,—$CH_2CH_2$—, —cyclopropyl—, —cyclobutyl—, —cyclopentyl—, —oxetanyl—, — tetrahydrofuranyl—, —tetrahydropyranyl—, —pyrrolidinyl— and —piperidinyl— are optionally substituted by 1, 2 or 3 $R_c$.

8. The compound, isomer thereof or pharmaceutically acceptable salt thereof as defined in claim 7, wherein $L_1$ is selected from the group consisting of —$CH_2$—, —CH($CH_3$)—, —C($CH_3$)$_2$—, —$CH_2CH_2$—,

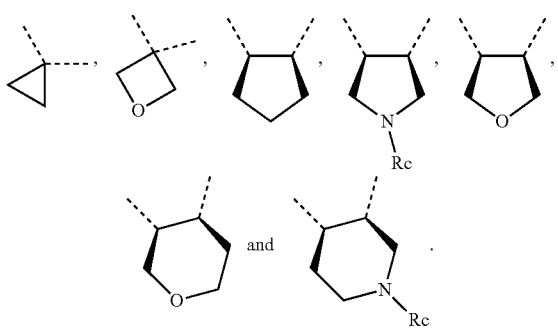

9. The compound, isomer thereof or pharmaceutically acceptable salt thereof as defined in claim 8, wherein $L_1$ is selected from the group consisting of —$CH_2$—, —$CH_2CH_2$—, —CH($CH_3$)—, —C($CH_3$)$_2$—,

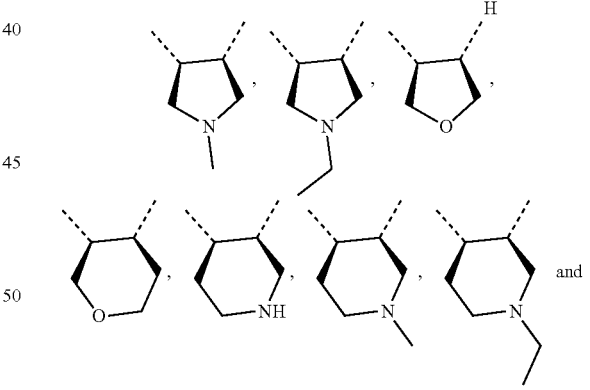

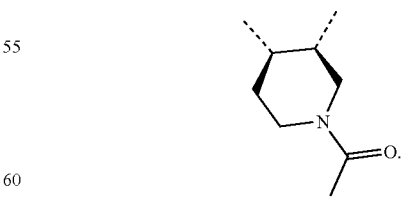

10. The compound, isomer thereof or pharmaceutically acceptable salt thereof as defined in claim 1, wherein $L_2$ is selected from the group consisting of —$CH_2$—, —$CH_2CH_2$—, —$CH_2CH_2O$—, —CH($CH_3$)O—, —O—, —NH—, —$CH_2NH$— and —$CH_2O$—.

11. The compound, isomer thereof or pharmaceutically acceptable salt thereof as defined in claim 1, wherein the moiety

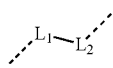

is selected from the group consisting of

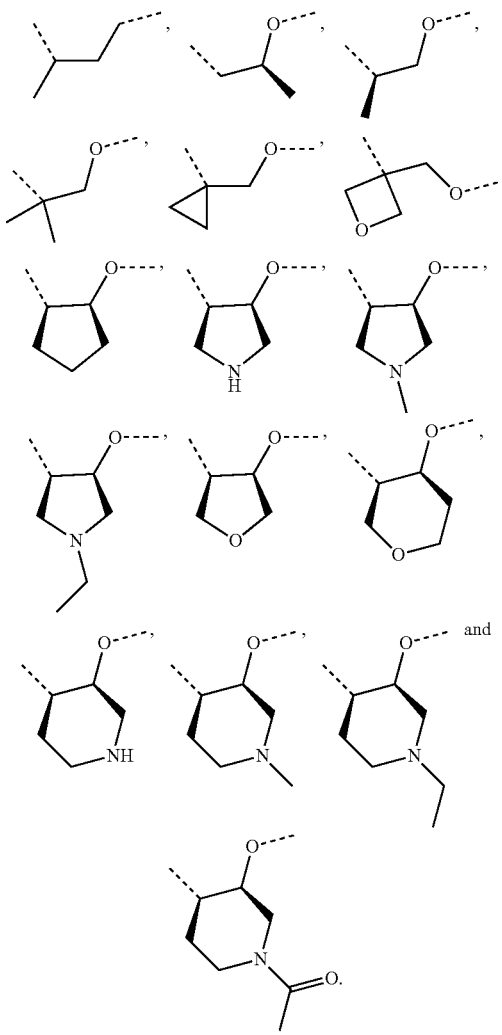

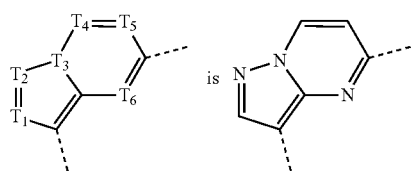

12. The compound, isomer thereof or pharmaceutically acceptable salt thereof as defined in claim 1, wherein the moiety

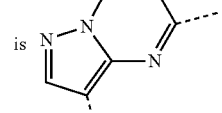

is 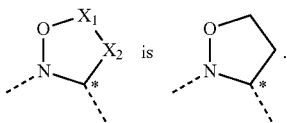

13. The compound, isomer thereof or pharmaceutically acceptable salt thereof as defined in claim 1, wherein the moiety

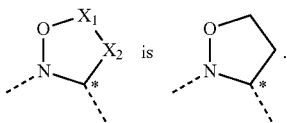 is 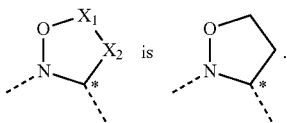.

14. The compound, isomer thereof or pharmaceutically acceptable salt thereof as defined in claim 1, wherein the compound is selected from:

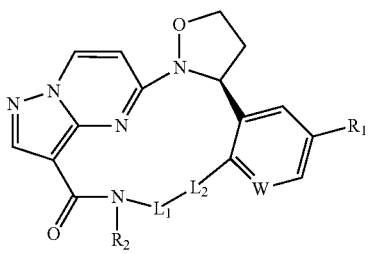

(II-1)

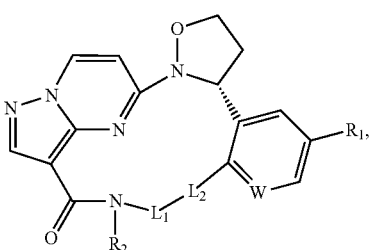

(II-2)

wherein,
W, $R_1$, $R_2$, $L_1$ and $L_2$ are as defined in claim 1.

15. The compound, isomer thereof or pharmaceutically acceptable salt thereof as defined in claim 14, wherein the compound is selected from:

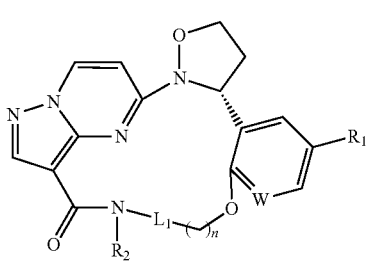

(II-3)

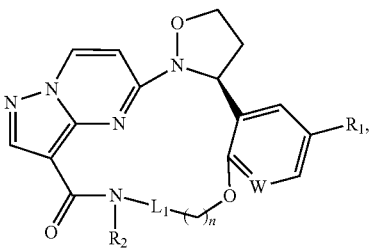

(II-4)

wherein,
n is selected from the group consisting of 0 and 1.

16. A compound, an isomer thereof or a pharmaceutically acceptable salt thereof, wherein the compound is selected from:

71
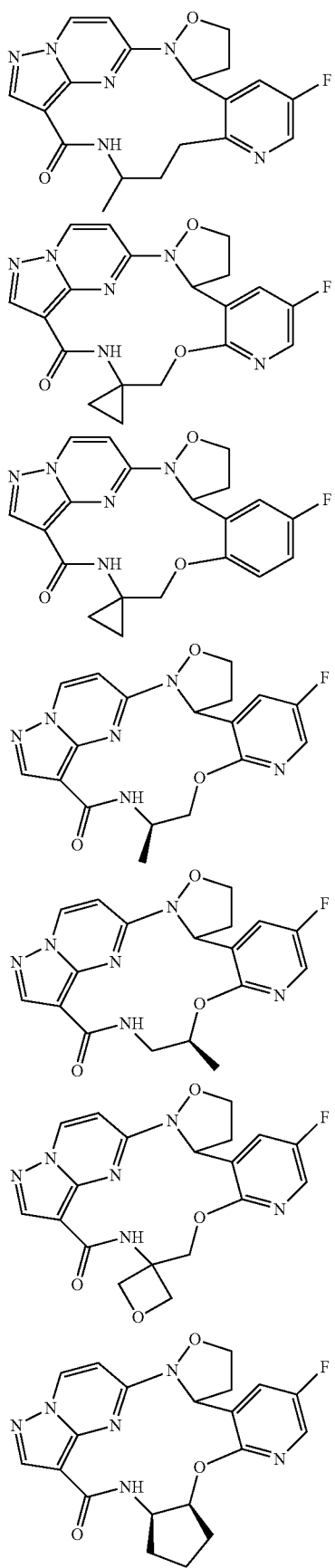
72
-continued
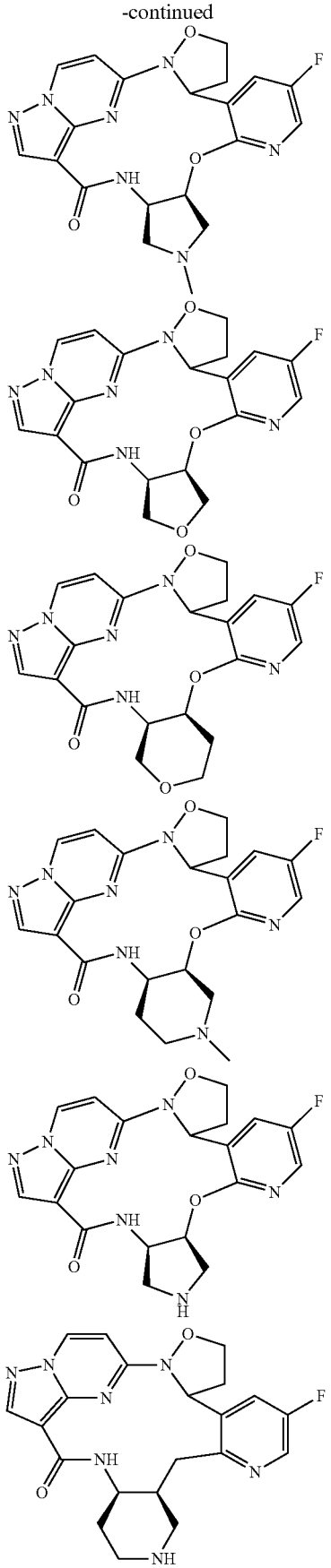

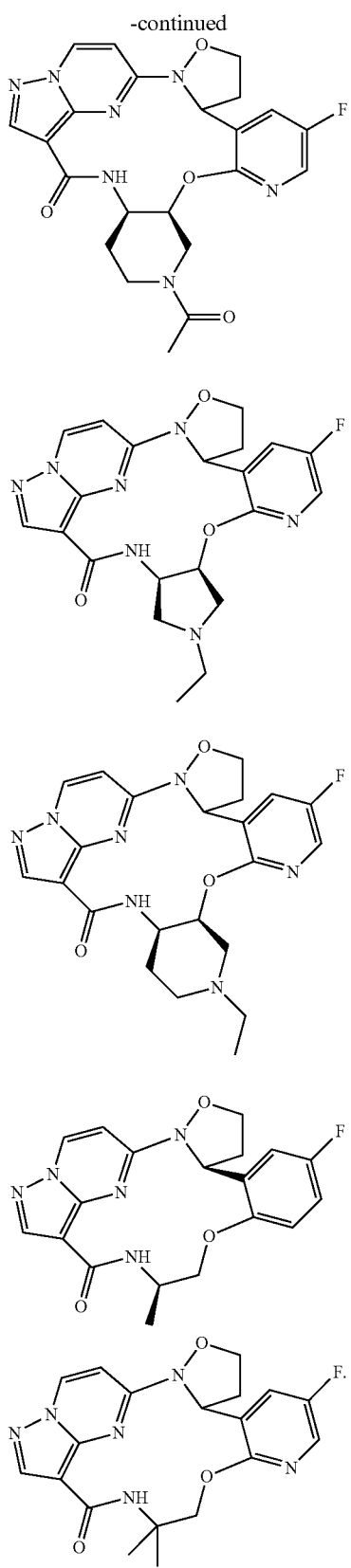
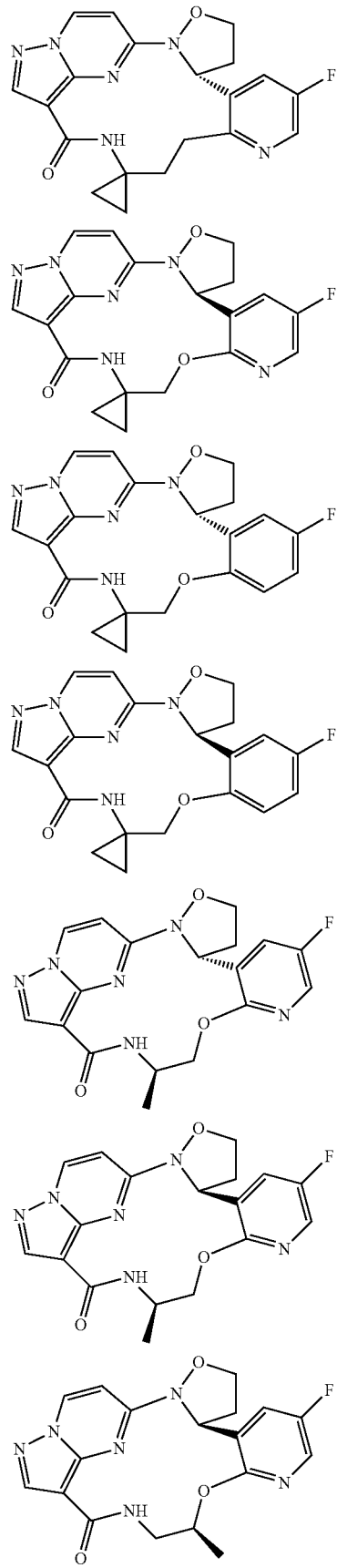
17. The compound, isomer thereof or pharmaceutically acceptable salt thereof as defined in claim 16, wherein the compound is selected from

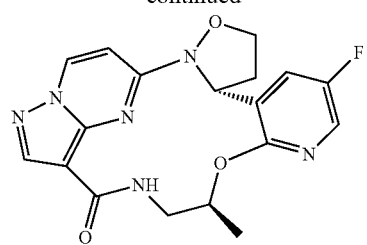
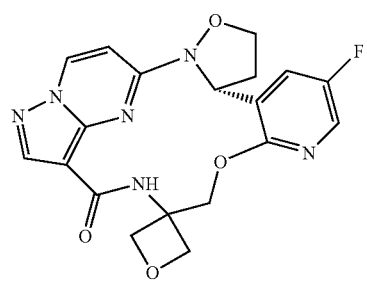
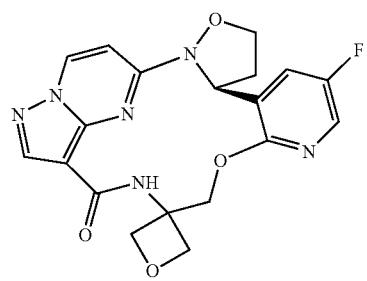
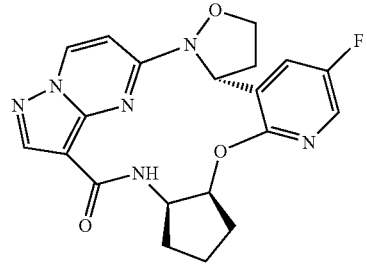
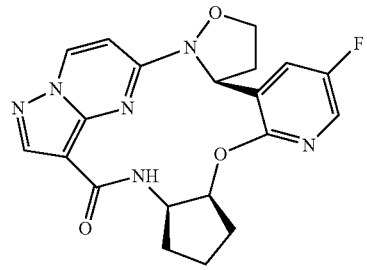
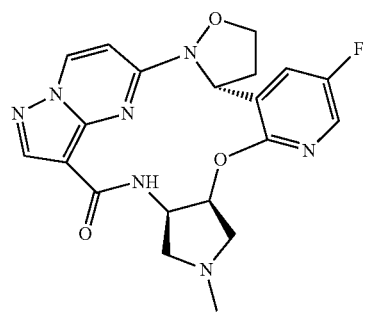
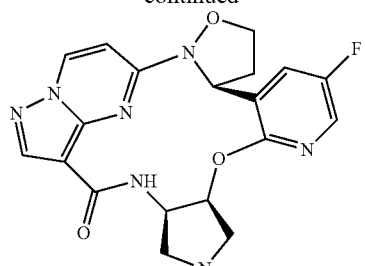
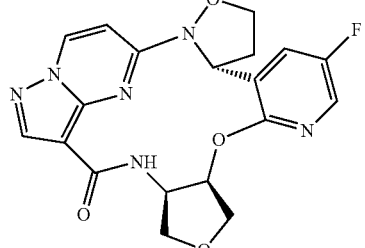
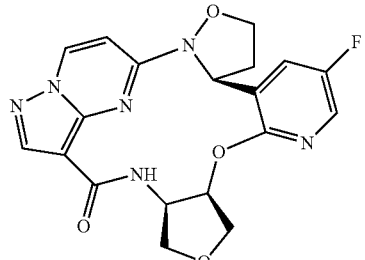
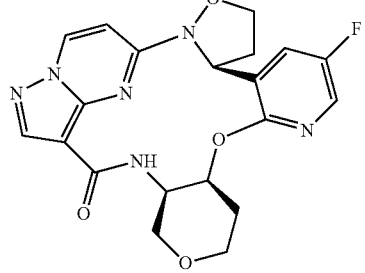
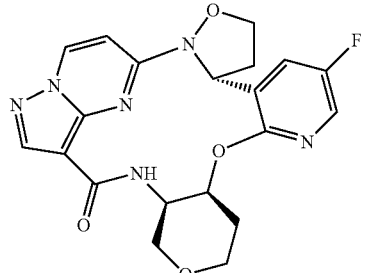
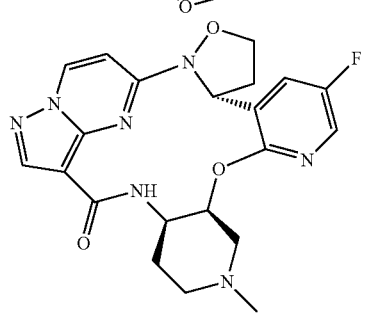

77
-continued
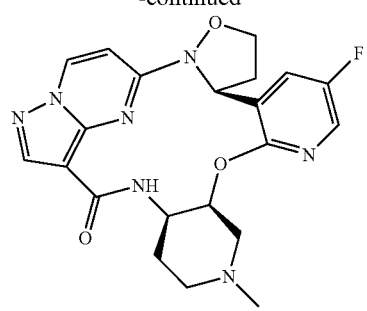
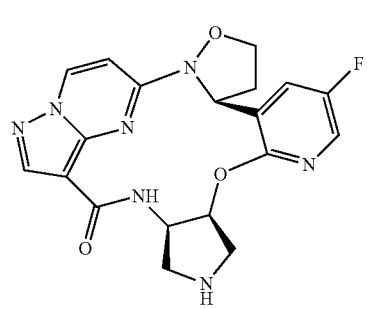
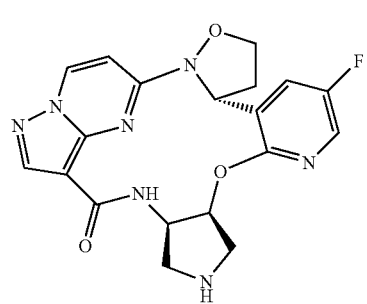
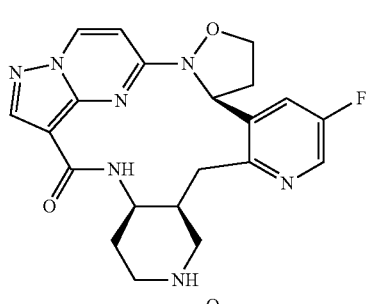
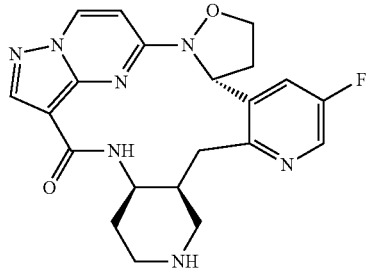
78
-continued
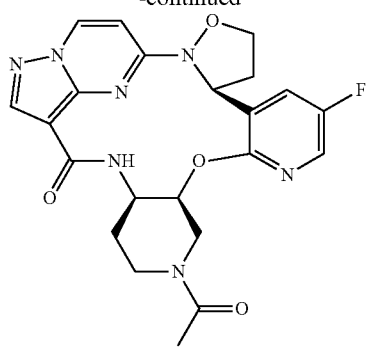
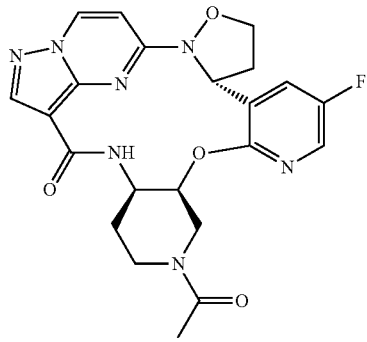
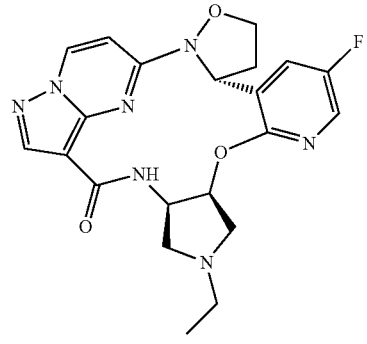
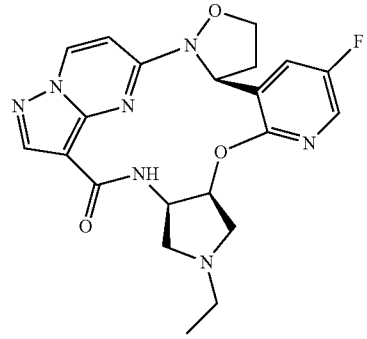
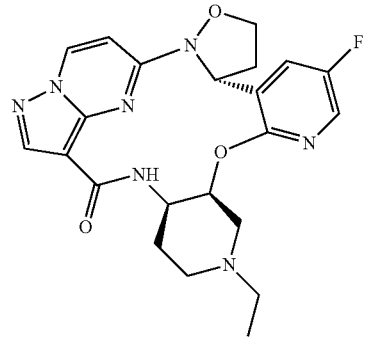

-continued

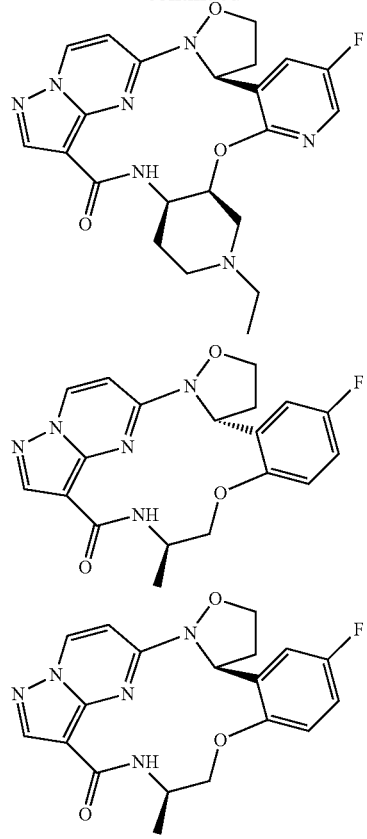

-continued

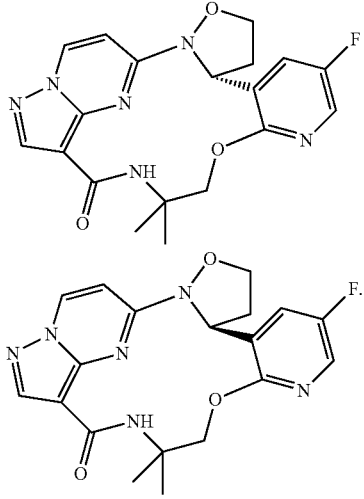

18. A pharmaceutical composition comprising a therapeutically effective amount of the compound or pharmaceutically acceptable salt thereof as defined in claim 1 as active ingredient and a pharmaceutically acceptable carrier.

19. A method for treating a disease related to Trk, ALK and Ros1 kinase in a subject in need thereof, comprising: administering an effective amount of the compound or pharmaceutically acceptable salt thereof as defined in claim 1 to the subject, the disease related to Trk, ALK and Ros1 kinase is a colon cancer or a lung cancer.

* * * * *